United States Patent [19]

Nomura et al.

[11] Patent Number: 5,025,005
[45] Date of Patent: * Jun. 18, 1991

[54] LIPID DERIVATIVES, THEIR PRODUCTION AND USE

[75] Inventors: Hiroaki Nomura, Takatsuki; Kohei Nishikawa, Kyoto; Susumu Tsushima, Suita, all of Japan

[73] Assignee: Takeda Chemical Industries, Ltd., Osaka, Japan

[*] Notice: The portion of the term of this patent subsequent to Apr. 12, 2005 has been disclaimed.

[21] Appl. No.: 556,280

[22] Filed: Jul. 23, 1990

Related U.S. Application Data

[60] Continuation of Ser. No. 141,276, Jan. 6, 1988, abandoned, which is a division of Ser. No. 906,310, Sep. 12, 1986, Pat. No. 4,737,518, which is a continuation-in-part of Ser. No. 719,579, Apr. 3, 1985, abandoned.

[30] Foreign Application Priority Data

Apr. 3, 1984 [WO] PCT Int'l Appl. ... PCT/JP84/00163
Oct. 11, 1984 [WO] PCT Int'l Appl. ... PCT/JP84/00476
Feb. 15, 1985 [WO] PCT Int'l Appl. ... PCT/JP85/00062
Oct. 1, 1985 [JP] Japan ............... 60-219874

[51] Int. Cl.$^5$ ............................................. A61K 31/33
[52] U.S. Cl. ..................... 514/183; 514/210; 514/211; 514/212; 514/222.2; 514/237.5; 514/255; 514/256; 514/326; 514/341; 514/342; 514/348; 514/357; 514/417; 514/418; 540/544; 540/553; 540/608; 544/59; 544/158; 544/159; 544/160; 544/161; 544/168; 544/171; 544/310; 544/312; 544/336; 544/389; 544/400; 546/226; 546/244; 546/247; 546/272; 546/276; 546/278; 546/332; 546/334; 546/335; 548/181; 548/309; 548/341; 548/312; 548/465; 548/477; 548/538; 548/567; 548/953; 548/966
[58] Field of Search ............... 514/183, 210, 211, 212, 514/222, 228, 234, 235, 255, 256, 326, 341, 342, 348, 357, 417, 418; 540/544, 553, 608; 544/59, 158, 159, 160, 161, 168, 171, 310, 312, 336, 389, 400; 546/226, 244, 247, 272, 335; 548/181, 264, 309, 312, 465, 477, 538, 567, 953, 966

[56] References Cited

U.S. PATENT DOCUMENTS

4,408,052 10/1983 Hozumi et al. .................. 546/22
4,426,525 1/1984 Hozumi et al. .................. 546/22
4,582,824 4/1986 Nishikawa et al. ............... 514/77
4,731,373 3/1988 Barner ........................... 514/365

FOREIGN PATENT DOCUMENTS

94856 9/1983 European Pat. Off. .
109255 5/1984 European Pat. Off. .
59-31728 2/1984 Japan .

OTHER PUBLICATIONS

Central Patents Index Basic Abstracts Journal Section B: Week K14 (1 Jun. 83) 33708 K/14 J58035-116.

*Primary Examiner*—Michael L. Shippen
*Attorney, Agent, or Firm*—Wegner, Cantor, Mueller & Player

[57] ABSTRACT

Novel lipid derivatives of the formula

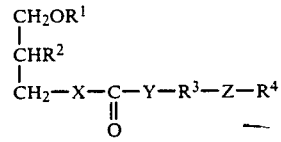

[wherein $R^1$ is alkyl or alkylcarbamoyl; $R^2$ is hydrogen, hydroxy which may be substituted, amino which may be substituted or cyclic amino; $R^3$ is a chemical binding or alkylene which may be substituted; $R^4$ is hydrogen, alkyl or aralkyl; X and Y are independently O, S or an imino group which may be substituted, and when Y is an imino group, Y, together with the imino group represented by X or $R^4$, may form a ring; and Z is imino or a nitrogen-containing heterocyclic ring which may be substituted] and salts thereof have inhibiting activity on platelet activating factor and are useful as a preventive or therapeutic agent for a variety of circulatory diseases and allergic disorders and also as an antineoplastic agent.

41 Claims, No Drawings

LIPID DERIVATIVES, THEIR PRODUCTION AND USE

This application is a continuation of U.S. application Ser. No. 07/141,276, filed Jan. 6, 1988, now abandoned, which is a divisional of U.S. application Ser. No. 06/906,310, filed Sept. 12, 1986, now U.S. Pat. No. 4,737,518, which is a continuation-in-part of U.S. application Ser. No. 06/719,579, filed Apr. 3, 1985, abandoned.

TECHNICAL FIELD

The present invention relates to novel lipid derivatives which are of value as pharmaceuticals.

BACKGROUND ART

PAF "Platelet Activating Factor" possesses the structure of a phospholipid and is a chemical transmitter which exists in living organisms. It has been clarified that PAF, as its in-vivo function, is closely involved in allergy, anaphylaxis and inflammation as well as platelet aggregation, and furthermore, PAF is known to exhibit potent hypotensive activity.

When PAF is given to animals, on the other hand, complication of these activities causes the animals to produce symptoms of shock, occasionally leading to death. The shock produced by PAF resembles symptoms of shock due to endotoxin, and PAF is suspected to be involved in the endotoxin shock.

With reference to the metastasis of cancer, it is thought that platelet aggregation is implicated in the stage of implantation of cancer cells, and lipid derivatives having the ether and carbomoyl bonds, because enzymes capable of breaking such bonds are deficient particularly in cancer cells, further tend to accumulate in cancer cells and exhibit the action to bring about change in the lipid metabolism within the cancer cell, eventually resulting in death of cancer cells.

The present inventors, after intensive search into lipid derivatives having the PAF inhibitory activity which are valuable as a preventive and therapeutic agent for a variety of circulatory disturbances and diseases and allergic disorders and also as an antineoplastic agent, succeeded in the production of lipid derivatives exhibiting excellent activities and have come to complete the present invention.

DISCLOSURE OF THE INVENTION

The present invention relates to lipid derivatives of the formula:

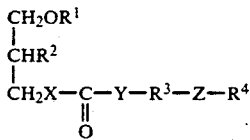

(I)

[wherein $R^1$ is alkyl or alkylcarbamoyl; $R^2$ is hydrogen, hydroxy which may be substituted, amino which may be substituted or cyclic amino; $R^3$ is a chemical binding (in other words, a chemical bond) or alkylene which may be substituted; $R^4$ is hydrogen, alkyl or aralkyl; X and Y are independently O (oxygen atom), S (sulfur atom) or an imino group which may be substituted, and when Y is an imino group, Y, taken together with the imino group represented by X or $R^4$, may form a ring; Z is imino or a nitrogen-containing heterocyclic ring which may be substituted] and to salts thereof.

With reference to the above formula (I), the alkyl group represented by $R^1$ may be straight-chain or branched-chain ones, and includes alkyl groups having about 10 to 30 carbon atoms, such as decyl, undecyl, tridecyl, tetradecyl, pentadecyl, hexadecyl, heptadecyl, octadecyl, nonadecyl, eicosanyl, heneicosanyl, docosanyl, tricosanyl, tetracosanyl, pentacosanyl, hexacosanyl, heptacosanyl, octacosanyl, nonacosanyl, triacontanyl, farnesyl and dihydrophytyl; among others, alkyl groups of 14 to 20 carbon atoms are preferable, with alkyl groups of 14 to 18 carbon atoms being more preferable, with alkyl groups of 15 to 18 carbon atoms being still more preferable, with alkyl groups of 16 to 18 carbon atoms being most preferable. In cases in which $R^1$ is an alkylcarbamoyl group, $R^1$ can be expressed as the formula:

$$R^5NHCO- \qquad (II)$$

wherein $R^5$ includes alkyl groups having about 10 to 30 carbon atoms as is the case with the alkyl groups represented by $R^1$ as mentioned above; among others, preferred are those having an alkyl group having 14 to 20 carbon atoms as the alkyl group in the alkylcarbamoyl group, and those having an alkyl group of 14 to 18 carbon atoms are more preferred, and those having an alkyl group of 15 to 18 carbon atoms are further more preferred and those having an alkyl group of 16 to 18 carbon atoms are most preferred.

As the optionally substituted hydroxyl group represented by $R^2$, there may be mentioned, for example, hydroxy, alkoxy, aralkyloxy, acyloxy or groups of the formula:

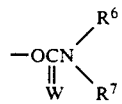

(III)

[wherein W is an oxygen or sulfur atom; $R^6$ and $R^7$ are independently hydrogen or alkyl, or both, taken together with the adjacent nitrogen atom, form a ring].

As the alkoxy group represented by $R^2$, there may be mentioned lower alkoxy groups having about 1 to 5 carbon atom, such as methoxy, ethoxy, propoxy, isopropoxy, butoxy, isobutoxy and pentoxy.

As the aralkyloxy group represented by $R^2$, there may be mentioned phenyl-lower($C_{1-5}$)alkoxy, such as benzyloxy, phenethyloxy, α-methylbenzyloxy, α-methylphenethyloxy and β-methylphenethyloxy.

As the acyloxy group represented by $R^2$, there may be mentioned lower alkanoyloxy having about 1 to 5 carbon atoms, such as formyloxy, acetyloxy, propionyloxy, butyryloxy, isobutyryloxy, valeryloxy and isovaleryloxy, and acyloxy groups, such as benzoyloxy, phenoxycarbonyloxy and lower($C_{1-5}$)alkoxycarbonyloxy (e.g., methoxycarbonyloxy, ethoxycarbonyloxy, propoxycarbonyloxy, butoxycarbonyloxy, etc.).

Referring to the formula (III), the alkyl group represented by $R^6$ or $R^7$ includes lower alkyl groups having about 1 to 5 carbon atoms, such as methyl, ethyl, propyl, isopropyl, butyl, isobutyl and pentyl. The ring which $R^6$ and $R^7$, taken together with the adjacent nitrogen atom, forms includes 3- to 7-membered heterocyclic rings which may have hetero atoms, such as nitrogen, oxygen and sulfur atoms, in addition to the said nitrogen atom, such as 1-aziridinyl, 1-azetidinyl, 1-pyrrolidinyl, piperidino, 1-perhydroazepinyl, 1-piperazinyl, morpholino, thiomorpholino, 1-perhydrodiazepinyl, 4-perhydrooxazepinyl and 4-perhydrothiazepinyl.

The optionally substituted amino represented by $R^2$ includes, for example, amino and acylamino.

As the acylamino group represented by $R^2$, there may be mentioned lower alkanoylamino having about 1 to 5 carbon atoms, such as formamido, acetamido, propionamido, butanamido, isobutanamido, valeramido and isovaleramido, and acylamino groups, such as benzoylamino.

As the cyclic amino represented by $R^2$, there may be mentioned 3- to 7-membered hetero-mono-cyclic rings, such as 1-aziridinyl, 1-azetidinyl, 1-pyrrolidinyl, piperidino, 1-perhydroazepinyl, 1-piperazinyl, morpholino, thiomorpholino, 1-perhydrodiazepinyl, 4-perhydrooxazepinyl and 4-perhydrothiazepinyl, and condensed rings having about 8 to 9 carbon atoms, such as 2-isoindolinyl. The said heterocyclic and condensed rings may be substituted by, for example, one or two oxo groups, at their positions susceptible to substitution, and the substituted hetero-mono-cyclic and condensed rings include, for example, 2,5-dioxopyrrolidinyl and 1,3-dioxoisoindolinyl.

The compounds having alkoxy as $R^2$ are more preferable.

The alkylene chain represented by $R^3$ includes straight-chain or branched-chain alkylene chains having about 1 to 8 carbon atoms, and there may be mentioned, for example, methylene, ethylene, trimethylene, tetramethylene, pentamethylene, hexamethylene, heptamethylene, and octamethylene. The said alkylene chains may be substituted by, for example, lower($C_{1-4}$)alkoxycarbonyl [e.g. methoxycarbonyl, ethoxycarbonyl] or carboxylato, and the case that said substituent is bound to the position adjacent to the carbon atom of the group $R^3$ being bound to the group Z is preferable. As $R^3$, among others methylene, ethylene and trimethylene are preferably, and methylene or ethylene is more preferably.

The alkyl group represented by $R^4$ includes lower alkyl groups having about 1 to 6 carbon atoms, such as methyl, ethyl, propyl, isopropyl, butyl, isobutyl, secbutyl, tert-butyl, pentyl and hexyl, and said lower alkyl group may have an unsaturated bond. The unsaturated lower alkyl group includes lower alkenyl groups having about 2 to 6 carbon atoms, such as vinyl, allyl, 2-butenyl and 3-butenyl.

The aralkyl group represented by $R^4$ includes phenyl-lower($C_{1-6}$)alkyl groups, such as benzyl, phenethyl, phenylpropyl, phenylbutyl, α-methylphenethyl and β-methylphenethyl.

In cases in which X is an optionally substituted imino group, X includes, for example, groups represented by the formula:

(IV)

[wherein $R^8$ is hydrogen, optionally substituted alkyl, acyl or optionally substituted carbamoyl]. In the above formula (IV), the alkyl group represented by $R^8$ includes lower alkyl groups having about 1 to 5 carbon atoms, such as methyl, ethyl, propyl, butyl and pentyl, wherein the said alkyl groups may be substituted, for example, by carboxyl and lower($C_{1-5}$)alkoxycarbonyl (e.g., methoxycarbonyl, ethoxycarbonyl, propoxycarbonyl, butoxycarbonyl, pentoxycarbonyl, etc.)

The acyl group represented by $R^8$ includes, for example, lower alkanoyl having about 1 to 5 carbon atoms (e.g., formyl, acetyl, propionyl, butyryl, isobutyryl, valeryl, isovarelyl, etc.), benzoyl, phenoxycarbonyl, lower($C_{1-5}$)alkoxycarbonyl (e.g., methoxycarbonyl, ethoxycarbonyl, propoxycarbonyl, butoxycarbonyl, pentoxycarbonyl, etc.).

The optionally substituted carbamoyl group represented by $R^8$ includes, for example, carbamoyl, lower($C_{1-5}$)alkylcarbamoyl (e.g., methylcarbamoyl, ethylcarbamoyl, propylcarbamoyl, butylcarbamoyl, etc.), di-lower($C_{1-5}$)alkylcarbamoyl (e.g., dimethylcarbamoyl, methylethylcarbamoyl, diethylcarbamoyl, methylpropylcarbamoyl, etc.), 3- to 7-membered cyclic amino carbonyl [e.g., (aziridin-1-yl)carbonyl, (azetidin-1-yl)carbonyl, (pyrrolidin-1-yl)carbonyl, piperidinocarbonyl, (perhydroazepin-1-yl)carbonyl, (piperazin-1-yl)carbonyl, morpholinocarbonyl, thiomorpholinocarbonyl, etc.], and the like.

In cases in which Y is an optionally substituted imino group, Y includes, for example, groups represented by the formula:

In the formula (V), the group represented by $R^9$ includes groups like those exemplified for $R^8$.

In cases in which X and Y both are an imino group, $R^8$ and $R^9$ may be the same or different, and $R^8$ and $R^9$ may combine with each other to form alkenylene, alkylene, etc.

The alkenylene and alkylene bridges which $R^8$ and $R^9$ combine with each other to form includes lower alkenylene and alkylene bridges having about 1 to 4 carbon atoms, such methylene, ethylene, trimethylene, tetramethylene, vinylene and propenylene, and may be substituted by, for example, one or two oxo groups at their positions susceptible to substitution. The substituted alkylene and alkenylene include, for example, 1-oxoethylene, 3-oxopropenylene and 1,2-dioxoethylene. Specifically, the group represented by the formula:

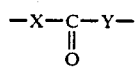

includes;

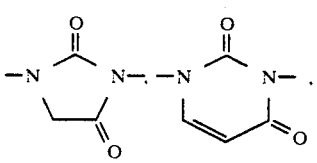

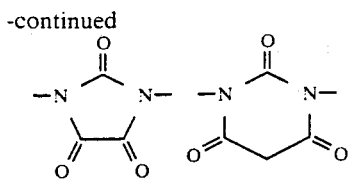

and the like.

In cases in which Y is an imino group, $R^9$ and $R^4$ may combine with each other to form alkenylene and alkylene, whereby the alkenylene and alkylene bridges which $R^9$ and $R^4$ combine with each other to form include lower alkenylene and alkylene bridges having about 1 to 4 carbon atoms, such as methylene, ethylene, trimethylene, tetramethylene, vinylene and propenylene, and these groups may be substituted by, for example, one or two oxo groups at their positions susceptible to substitution. The substituted alkylene and alkenylene groups include, for example, 1-oxoethylene, 3-oxopropenylene and 1,2-dioxoethylene. Specifically, the group represented by the formula:

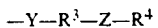

includes:

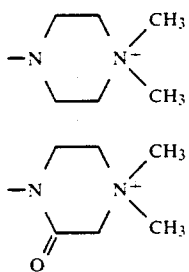

and the like.

As X, is preferable O.

Y includes preferably an imino group which may be substituted, more preferably a substituted imino group, further more preferably an imino group substituted by lower alkanoyl.

The optionally substituted imino group represented by Z includes imino groups substituted by a lower alkyl group having about 1 to 6 carbon atoms which may be substituted by lower($C_{1-4}$)alkoxycarbonyl (e.g., methylimino, ethylimino, propylimino, isopropylimino, butylimino, isobutylimino, sec-butylimino, tert-butylimino, pentylimino, hexylimino, ethoxycarbonylmethylimino, etc.), and imino groups substituted by aralkyl groups such as phenyl-lower($C_{1-6}$)alkyl (e.g., benzylimino, phenethylimino, phenylpropylimino, phenylbutylimino, ($\alpha$-methylphenethyl)imino, ($\beta$-methylphenethyl)imino, etc.).

The group Z—$R^4$ which $R^4$ and an optionally substituted imino group represented by Z form includes, for example, amino, N-[lower($C_{1-6}$)alkyl]amino, N,N-[di-lower($C_{1-6}$)alkyl]-amino, N-[lower($C_{1-6}$)alkyl]-N-aralkylamino, N-aralkylamino, N,N-[di-lower($C_{1-6}$)alkyl]amino and the like. The above-mentioned aralkyl group includes phenyl-lower($C_{1-6}$)alkyl groups like those exemplified for $R^4$. The above-mentioned lower alkyl group may be substituted by, for example, lower($C_{1-4}$)alkoxycarbonyl, and may have an unsaturated bond [e.g., lower($C_{2-6}$)alkenyl]. Also, the imino group represented by Z may be converted into quaternary salt to form the imino group, and the said iminio group may be substituted by optionally lower($C_{1-4}$)alkoxycarbonyl or carboxylato substituted lower alkyl having about 1 to 6 carbon atoms or aralkyl (e.g., phenyl-lower($C_{1-6}$)alkyl, etc.). The said substituted iminio group includes, for example, dimethyliminio, methylethyliminio, methylpropyliminio, methylbutyliminio, methylpentyliminio, methylhexyliminio, diethyliminio, ethylpropyliminio, ethylbutyliminio, ethylpentyliminio, ethylhexyliminio, dipropyliminio, propylbutyliminio, propylpentyliminio, propylhexyliminio, dibutyliminio, butylpentyliminio, butylhexyliminio, dipentyliminio, pentylhexyliminio, dihexyliminio, benzylmethyliminio, dibenzyliminio, phenethylmethyliminio, diphenethyliminio, N-ethoxycarbonylmethyl-N-methyliminio and N-carboxylatomethyl-N-methyliminio.

The group Z—$R^4$ which $R^4$ and a substituted iminio group represented by Z form includes, for example, N,N,N-[tri-lower($C_{1-6}$)alkyl]ammonio, N,N-[di-lower($C_{1-6}$)alkyl]-N-aralkylammonio, N-[lower($C_{1-6}$)alkyl]-N,N-di-aralkylammonio, N,N,N-tri-aralkylammonio and the like. The above-mentioned aralkyl group includes phenyl($C_{1-6}$)alkyl groups like those exemplified for $R^4$. The above-mentioned lower alkyl group may be substituted by, for example lower($C_{1-4}$)alkoxycarbonyl or carboxylato, and may have an unsaturated bond [e.g. lower($C_{2-6}$)alkenyl]. Among others, the compounds wherein Z is dimethyliminio and $R^4$ is methyl, i.e. those wherein Z—$R^4$ is trimethylammonio are preferable.

The nitrogen-containing heterocyclic ring represented by Z includes heterocyclic rings containing at least one nitrogen atom, such as monocyclic or bicyclic heterocyclic rings which may contain, as ring forming atom, a nitrogen, oxygen or sulfur atom in addition to the said nitrogen atom. The said heterocyclic rings may be saturated, partially saturated or minimally hydrogenated such as heteroaromatic rings, and their examples include azetidinyl, pyrrolidinyl, piperidinyl, perhydroazepinyl, pyrrolinyl, pyrazolinyl, pyrrolyl, pyridyl, oxazolyl, thiazolyl, pyridazinyl, pyrimidyl, pyrazinyl, imidazolyl, morpholinyl, thiomorpholinyl, piperazinyl, pyrazolidinyl, indolyl, isoindolyl, 1H-indazolyl, purinyl, quinolinyl, isoquinolinyl, 1,2,3,4-tetrahydroquinolinyl, perhydroindolyl and perhydroisoquinolinyl; in the case of monocyclic heterocyclic rings, among others, the 4- to 7-membered rings are preferable, and 5- to 6-membered rings are more preferable and thiazolyl or pyridyl is most preferable. These groups may be substituted at their positions susceptible to substitution by, for example, lower($C_{1-4}$)alkyl (e.g., methyl, ethyl, propyl, butyl, etc.), hydroxyl, amino(imino), mono- or di-lower($C_{1-4}$)alkylamino (e.g., methylamino, dimethylamino, etc.), carbamoyl, ureido, hydroxy- or amino-substituted lower($C_{1-4}$)alkyl (e.g., hydroxyethyl, aminoethyl, etc.), carboxyl, carboxylato and lower($C_{1-4}$)alkoxycarbonyl (e.g. methoxycarbonyl), and their examples include N-methylmorpholinyl, N-methylpiperidinyl, N-methylpiperazinyl, N-methylpyrrolidinyl, N-ethylpyrrolidinyl and the like.

The nitrogen atom in the said nitrogen-containing heterocyclic ring may be converted into a quaternary salt with $R^4$, and there may be mentioned, for example, groups, such as N,N-dimethylpyrrolidinio, N-methylpyridinio, N-ethylpyridinio, N-propylpyridinio, N-butylpyridinio, N-methyl-N-ethylpyrrolidinio, 3-methylthiazolio, 3-ethylthiazolio, 3-propylthiazolio, 3-butylthiazolio, N-allylpyridinio, N-ethoxycarbonylmethylpyridinio. Also, the said nitrogen atom may be converted into a quaternary salt by combining with $R^3$, and the heterocyclic ring containing the said nitrogen atom converted into a quaternary salt includes such groups as pyridinio-1-yl, oxazolio-3-yl, thiazolio-3-yl, pyridazinio-1-yl, pyrimidinio-1-yl, pyradinio-1-yl, quinolinio-1-yl, isoquinolinio-2-yl, 4-methylmorpholinio-4-yl, 1-methylpiperidinio-1-yl, 1-methylpiperazinio-1-yl, 1-methylpyrrolidinio-1-yl, 1-ethylpyrrolidinio-1-yl, 1-methylimidazolio-yl, 3-carboxylatopyridinio-1-yl, 3-methoxycarbonylpyridinio-1-yl and 4-dimethylaminopyridinio-1-yl.

In case that $R^4$ is lower($C_{1-6}$)alkyl, lower($C_{1-4}$)alkoxycarbonyl-lower($C_{1-6}$)alkyl, carboxylato-lower($C_{1-6}$)alkyl or aralkyl, the position in the nitrogen-containing heterocyclic ring represented by Z to which $R^4$ is bound may be any positions if they are the positions susceptible to such binding, but the case the position in said heterocyclic ring to which $R^4$ is bound is the nitrogen atom is preferable in case that the position in the said heterocyclic ring to which $R^3$ is bound is other than said nitrogen atom. In case that the position in said heterocyclic ring to which $R^3$ is bound is the nitrogen atom, the position in said heterocyclic ring to which $R^4$ is bound may be any positions if they are the positions susceptible to such binding.

The group represented by Z—$R^4$ includes, for example, optionally lower($C_{1-6}$)alkyl ($C_{2-6}$alkenyl), lower($C_{1-4}$)alkoxycarbonyl-lower($C_{1-6}$)alkyl ($C_{2-6}$)alkenyl), carboxylato-lower($C_{1-6}$)alkyl ($C_{2-6}$alkenyl) or aralkyl substituted azetidinyl, pyrrolidinyl, piperidinyl, perhydroazepinyl, pyrrolinyl, pyrazolinyl, pyrrolyl, pyridyl, oxazolyl, thiazolyl, pyridazinyl, pyrimidyl, pyradinyl, imidazolyl, morpholinyl, thiomorpholinyl, piperazinyl, pyrazolidinyl, indolyl, isoindolyl, 1H-indazolyl, purinyl, quinolinyl, isoquinolinyl, perhydroindolyl, perhydroisoquinolinyl, imidazolio, pyridinio, oxazolio, thiazolio, pyridazinio, pyrimidinio, pyradinio, quinolinio, isoquinolinio, morpholinio, piperidinio, piperazinio and pyrrolidinio groups. These groups may be further substituted by, for example, optionally hydroxy or amino substituted lower($C_{1-6}$)alkyl, hydroxy, amino(imino), mono- or di-lower($C_{1-4}$)alkylamino, carbamoyl, ureido, carboxy, carboxylato or lower($C_{1-4}$)alkoxycarbonyl.

With reference to the example of $R^4$ combining with the imino group represented by Y, specifically, the group as represented by the formula:

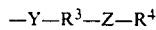

includes;

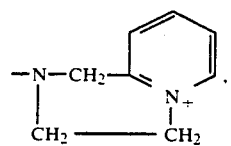

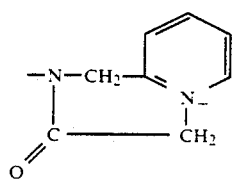

and the like.

As the nitrogen-containing heterocyclic ring represented by Z, the heterocyclic rings containing the quaternary nitrogen atom are more preferable.

The position in the heterocyclic ring to which $R^3$ is bound may be any positions, only if they are the positions susceptible to such binding [e.g. 2-pyridyl, thiazol-2-yl, thiazol-4-yl, N-methylpyridinio-2-yl, N-methylpyridinio-3-yl, N-ethylpyridinio-2-yl, N-butylpyridinio-2-yl, N-methoxycarbonylmethylpyridinio-2-yl, N-ethylpyrrolidin-2-yl, N-methyl-N-ethylpyrrolidinio-2-yl, N-ethylpiperidin-3-yl, N-methyl-N-ethylpyperidinio-3-yl, 3-methylthiazolio-2-yl, 3-ethylthiazolio-2-yl, 3-propylthiazolio-2-yl, 3-butylthiazolio-2-yl, 3-methylthiazolio-4-yl, 3-ethylthiazolio-4-yl, 3,4-dimethylthiazolio-5-yl, N-allylpyridinio-2-yl], but the nitrogen atom or its adjacent positions (the positions adjacent to the nitrogen atom) are more preferable.

The salt of the compound (I) includes pharmaceutically acceptable salts, such as hydrochlorides, hydrobromides, hydroiodides, sulfates, nitrates and phosphates, and among others, the acid additions salts are preferable. In cases in which Z has the quaternary nitrogen atom, the compound (I) may form salts with pharmaceutically acceptable anions such as acid anions (e.g. chlorine ion, bromine ion, iodine ion, sulfate ion, nitrate ion, phosphate ion and acetate ion) and hydroxyl ion, and may also form intramolecular salts.

The said salts with pharmaceutically acceptable anions and intramolecular salts fall within the scope of the pharmaceutically acceptable salt.

The compound (I), in some instances, may have an asymmetric carbon in the molecule, depending upon the type of the substituent represented by $R^2$, and when the compound exists in two kinds of the stereoisomers with the R- and S-configurations, their individual isomers and mixture thereof both fall within the scope of the present invention.

The compound (I) and its salt exhibit excellent PAF inhibitory activity, and are useful as a prophylactic and therapeutic agent against circulatory disturbances and diseases caused by PAF, such as thrombosis, cerebral apoplexy (e.g., cerebral hemorrhage, cerebral thrombosis, etc.), myocardial infarction, angina pectoris, thrombophlebitis, glomerulonephritis and shock (e.g., endotoxin shock, endotoxin-associated intravascular hemagglutination syndrome, anaphylactic shock, hemorrhagic shock, etc.) and disorders (e.g., bronchial asthma, etc.) associated with allergy as well as an antineoplastic agent.

The compound (I) and its salt are so hydrophilic and lipophilic and so low toxic, and can therefore be safely administered orally or parenterally, as it is in a form of powder or as a pharmaceutical composition in the suitable dosage form, to mammals. The dosage varies depending upon the subject to be administered, disease to be treated, conditions thereof and route of administration, and when the compound (I) or its salt is to be administered through intravenous injection for the prophylaxis or treatment of shock in a human adult, for example, it can be advantageously administered usually in a single dose in the range of about 0.01 to 20 mg/kg body weight, preferably in the range of about 0.1 to 10 mg/kg body weight, more preferably in the range of 0.1 to 2 mg/kg body weight, about once to 5 times a day, preferably about once to 3 times a day. In addition, the compound (I) or its salt can be administered through drip infusion in a single dose in the range of about 0.01 to 1.0 mg/kg body weight/min. over a period of about 1 hour, about once to 5 times a day, preferably about once to 3 times a day. The dosages for other non-oral routes as well as the oral dosage may be selected referring to the above-mentioned dose-levels. When shock symptoms are very serious, dosage increases may be made according to the severity of the symptoms.

When the compound (I) or its salt is administered orally for the prophylaxis and treatment of thrombosis in an human adult, for example, it can be advantageously administered usually in a single dose in the range of about 0.1 to 20 mg/kg body weight, about once to 5 times a day, preferably about once to 3 times. More particularly, it is preferable to administer it in a single dose in the range of about 0.5 to 4 mg/kg body weight for the purpose of prophylaxis of thrombosis and in a single dose in the range of about 4 to 10 mg/kg body weight for the purpose of treatment of thrombosis, respectively, about once to 3 times a day. The dosages for other non-oral routes may be selected referring to the above-mentioned dose-levels.

The compound (I) and its salts show a strong effect in inducing cell differentiation of cultured cancerous cells, and are useful as an antineoplastic agent. Cancerous cell differentiating agents are expected as antineoplastic agents of a new type, but no compounds satisfactory as antineoplastic agents have been found.

The compound (I) and salts thereof are so hydrophilic and lipophilic and of such low toxicity that they can be safely administered orally or parenterally as such in a form of powder or as a pharmaceutical composition in a suitable dosage form, to warm-blooded animals. The dosage varies depending upon the subject to be administered, disease to be treated, conditions thereof and route of administration, and when the compound (I) or a salt thereof is to be administered to, for example, tumor-carrying warm-blooded animals, it can be advantageously administered usually in a single dose in the range of about 0.01 to 20 mg/Kg body weight, preferably in the range of about 0.1 to 10 mg/kg body weight, more preferably in the range of 0.1 to 2 mg/kg body weight, about once to five times a day, preferably about once to three times a day. In addition, the compound (I) or a salt thereof can be administered through drip infusion in a single dose in the range of about 0.01 to 1.0 mg/kg body weight/min. over a period of about one hour, about once to five times a day, preferably about once to three times a day. The dosages for other non-oral routes as well as the oral dosages may be selected referring to the above-mentioned dose-levels.

The pharmaceutical composition to be used for the above administration comprises an effective amount of the compound (I) or its salt and a pharmaceutically acceptable carrier or excipient, and the said composition is provided in a dosage form suitable for oral or non-oral administration.

The composition for oral administration includes, for example, solid or liquid dosage forms, and as their specific examples, there may be mentioned tablets (inclusive of sugar-coated tablets and film-coating tablets), pills, granules, powders, capsules (inclusive of soft capsules), syrups, emulsions, suspensions, etc. Such compositions can be manufactured by the per se known procedures and comprise carriers and excipients commonly used in the pharmaceutical industry. Examples of the carriers and excipients for the preparation of tablets include lactose, starch, sugar and magnesium stearate, etc.

The compositions for non-oral administration include for example, injections and suppositories, and as examples of the injection, there may be mentioned dosage forms, such as injectable solutions for intravenous injection, for subcutaneous injection, for intracutaneous injection, for intramuscular injection and for drip injection. Such injectable solutions are prepared by the per se known procedure, for example, by dissolving, suspending or emulsifying the compound (I) or its salt in a sterile aqueous or oily solution usually used for injectable solutions. The aqueous solution for injection includes, for example, physiological saline solution, isotonic solution containing glucose and other adjuvants, and may be employed in combination with a suitable solubilizer, such as alcohols (e.g., ethanol, etc.), polyalcohols (e.g., propylene glycol, polyethylene glycol, etc.), and nonionic surface active agents [e.g., polysorbate 80, HCO-50 (polyoxyethylene (50 mol) adduct of hydrogenated castor oil), etc.]. The oily solution for injection includes, for example, sesame oil and soybean oil, and may be used in combination with such a solubilizer as benzyl benzoate and benzyl alcohol. The injectable solution prepared is usually filled into suitable ampoules to be supplied as an injection. The suppositories for rectal administration are produced by the per se known procedure, for example, by incorporating the compound (I) or its salt into a usual suppository base, followed by compression into a shape.

Each of the above-mentioned compositions may contain other active ingredients, unless they bring about unfavorable interactions with the compound (I) or its salt.

The compound (I) or its salt can be produced, for example, by the following methods.

(A) (in cases in which the atom in Z bound to $R^3$ is a nitrogen atom):

A compound of the formula:

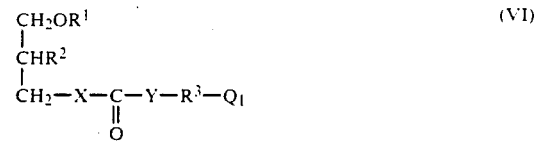

(VI)

[wherein $Q_1$ is a group (e.g., halogen, such as chlorine, bromine, and iodine, O-tosyl and O-mesyl groups, etc.) which is ready to undergo substitution with nitrogen; other symbols are as defined hereinbefore] is reacted with an optionally substituted amine (VII) or a nitrogen-containing cyclic compound (VIII) to give the compound (I). The reaction between the compounds (VI) and (VII) or (VIII) can be carried out by adding an equivalent or a large excess of the compound (VII) or (VIII) to the compound (VI) at 0° to +200° C. in the presence or absence of a solvent. The solvent includes, for example, toluene, benzene, ether, dioxane and tetrahydrofuran, and the compound (VII) or (VIII) itself can be used as a solvent. In the case of reaction under heating, the reaction may be carried out in a sealed tube.

A compound of the formula:

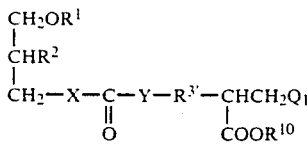  (VIa)

[wherein $R^{10}$ is lower($C_{1-4}$)alkyl, $R^{3'}$ is a chemical binding or $C_{1-6}$alkylene and other symbols are as defined hereinbefore] is converted with per se known method to a compound of the formula (VIb)

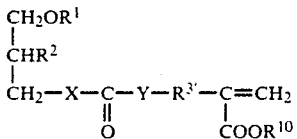  (VIb)

[wherein all symbols are as defined hereinbefore], and the compound (VIb) is reacted with the compound (VII) or (VIII) under the reaction conditions similar to those of the compounds (VI) and (VII) or (VIII), to give a compound of the formula:

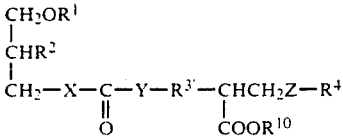  (Ia)

[wherein all symbols are as defined hereinbefore].

(B) A compound of the formula:

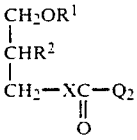  (IX)

[wherein $Q_2$ is a carbonyl-activating group (e.g., halogen (e.g., chlorine, etc.), phenoxy, etc.); other symbols are as defined hereinbefore] is reacted with a compound of the formula:

$$HY-R^3-Z-R^4 \quad (X)$$

[wherein each of the symbols is as defined hereinbefore] to give the compound (I). The reaction between (IX) and (X) can be carried out in the presence or absence of a solvent at $-10°$ to $+150°$ C. As the solvent, there can be used, for example, toluene, benzene, ether, dioxane, tetrahydrofuran and chloroform, and in order to accelerate the reaction, a base such as triethylamine and pyridine may be added. Also, (X) may be reacted with sodium hydride, n-butyllithium, etc. in the above mentioned solvent to convert into a metal salt, and reacted with the compound (IX).

(C) A compound of the formula:

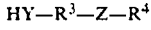  (XI)

[wherein $R^1$, $R^2$ and X are as defined hereinbefore] is reacted with a compound of the formula:

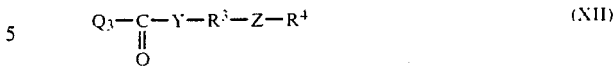  (XII)

[wherein $Q_3$ is a carbonyl-activating group (e.g., halogen (e.g., chlorine, etc.), phenoxy, etc.); other symbols are as defined hereinbefore] to give the compound (I). The reaction between the compounds (XI) and (XII) can be conducted in a manner similar to that of the reaction between the compounds (IX) and (X) in the above B.

(D) A compound of the formula:

  (XIII)

[wherein $R^1$ and $R^2$ are as defined hereinbefore] is reacted with the compound represented by the formula (X) to give (I) (X=NH). The reaction can be carried out in a manner similar to that of the reaction between (IX) and (X).

(E) A compound of the formula:

  (XIV)

[wherein the symbols are as defined hereinbefore] is reacted with a compound represented by the formula (XI) to give (I) (Y=NH). The reaction can be conducted in a manner similar to that of the reaction between (XI) and (XII).

The compound (XIV) can be readily synthesized, for example, by reacting a compound represented by the formula $H_2N-R^3-Z-R^4$ (XV) [wherein each of the symbols is as defined hereinbefore] with diphosgene at $-20°$ to $+120°$ C. in the presence or absence of an inert solvent, such as methylene chloride, chloroform, benzene, tetrahydrofuran and toluene or by reacting a compound represented by the formula $HOOC-R^3-Z-R^4$ (XVI) [wherein each of the symbols is as defined hereinbefore] with DPPA at $0°$ to $+150°$ C. in a solvent such as chloroform, toluene, benzene, dichloromethane and tetrahydrofuran in the presence of a tertiary amine, such as triethylamine and tributylamine, and further reacting those at $0°$ to $150°$ C. in the presence of a tertiary amine, such as pyridine.

The compound of the formula (I) where X and/or Y is an unsubstituted imino group can be reacted, for example, with an acid anhydride, acid halide, alkyl halide or alkyl isocyanate corresponding to $R^8$ or $R^9$ to give the compound of the formula (I) wherein X and/or Y is a substituted imino group. The reaction is generally allowed to proceed by maintaining the reaction temperature within the range of $-10°$ C. to $+150°$ C. in a solvent (e.g., benzene, toluene, chloroform, dichloromethane, ether, tetrahydrofuran, dimethylsulfoxide, dimethylformamide, etc.). In such a case, a base (e.g., triethylamine, pyridine, dimethylaminopyridine, sodium hydroxide, sodium hydride, etc.) can be allowed to coexist in the reaction for the purpose of accelerating the reaction rate.

The compound of the formula (I) wherein the nitrogen atom contained in a group represent by Z is a primary, secondary or tertiary amino can also be reacted, for example, with an alkyl halide to give the compound of the formula (I) wherein the nitrogen atom contained in a group represented by Z is a secondary, tertiary or quaternary amino. This reaction is allowed to proceed by maintaining the reaction mixture at a temperature of 0° to +150° C. in a solvent, such as ether, chloroform, tetrahydrofuran, benzene and toluene, in the presence of an equal amount or large excess of an alkyl halide or aralkyl halide.

A compound of the formula (I) wherein $R^1$ is hydrogen is reacted with an alkyl isocyanate to give a compound of the formula (I) wherein $R^1$ is alkylcarbamoyl. This reaction can be conducted in a manner similar to that of the reaction between (IX) and (X).

When a group readily susceptible to elimination is contained in the formula (I), such a group can be allowed to undergo elimination, followed by a subsequent reaction to introduce other substituents. When $R^2$ in the formula (I) is a benzyloxy group, for example, catalytic reduction is conducted to convert $R^2$ into a hydroxy group, and then acylation or carbamoylation can be carried out.

The starting compound (VI) can be produced, for example, in accordance with the following reaction schema.

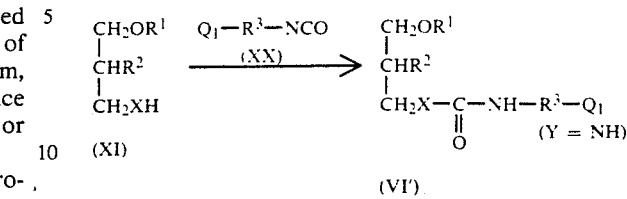

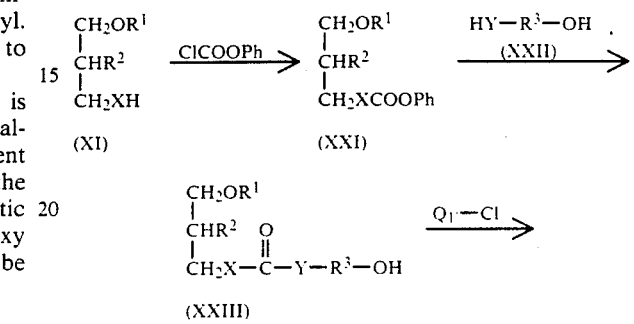

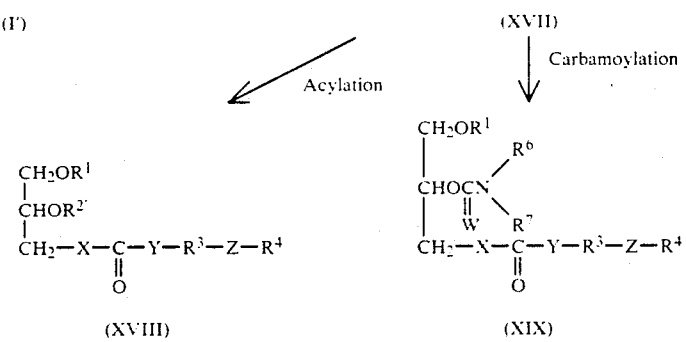

$R^{2'}$ is an acyl group.

In this reaction, when X and/or Y is an unsubstituted imino group, X and/or Y can also be acylated or carbamoylated simultaneously with the above acylation or carbamoylation. The catalytic reduction reaction in this reaction can be carried out by maintaining the reaction mixture at a temperature of room temperature to +100° C. in a solvent, such as alcohol, tetrahydrofuran, water and acetic acid, with use of a catalyst such as platinum oxide, palladium-carbon and Raney nickel. The acylation reaction of (XVII) can be carried out by maintaining a mixture of (XVII) and an active derivative of carboxylic acid (e.g., acid anhydrides, acid halides, etc.) at a temperature of −10° to +150° C. in an inert solvent (e.g., ether, chloroform, benzene, toluene, dichloromethane, tetrahydrofuran, dimethylformamide, etc.). In such a case, a tertiary amine (e.g., triethylamine, pyridine, dimethylaminopyridine, etc.) and the like may be added for the purpose of accelerating the reaction. The reaction of carbamoylating (XVII) to convert into (XIX) can be conducted by a procedure similar to that of the carbamoylation reaction [the method of producing the compound (XLIV)] of the starting compound to be described hereinafter.

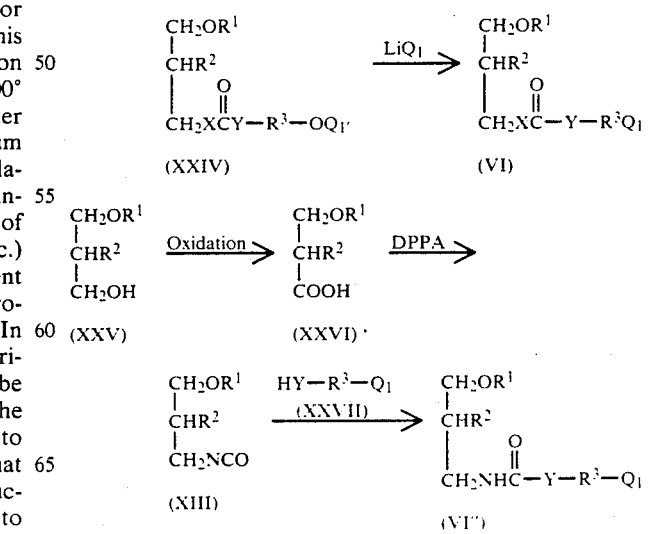

-continued

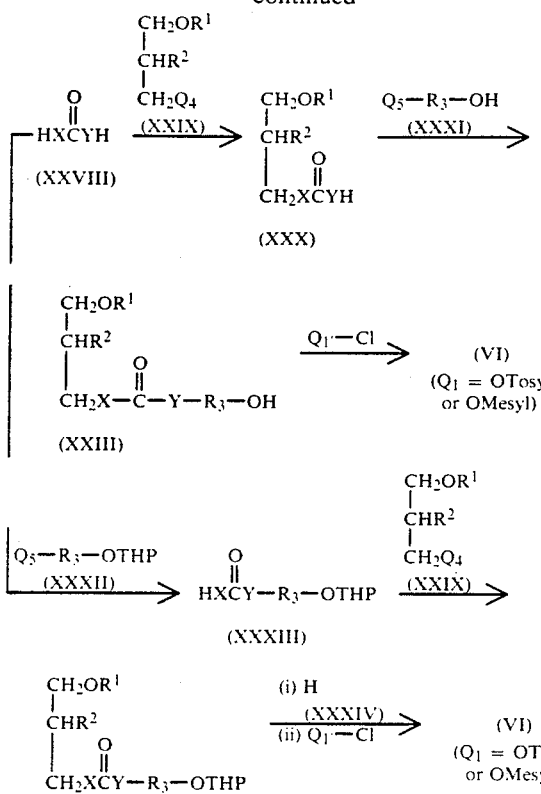

In the above formulae, $Q_1$, is tosyl or mesyl; THP is tetrahydropyran-2-yl; $Q_4$ and $Q_5$ are halogen (e.g., chlorine, bromine, iodine), OTosyl or OMesyl; other symbols are as defined hereinbefore.

This method is favorably employed in cases in which the compound represented by the formula

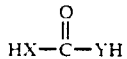

is a five-membered or six-membered ring compound (e.g., hydantoin, ura il, barbituric acid, etc.).

(IX) and (XII) can be synthesized, for example, by reacting (XI) and (X) respectively with phenyl chlorocarbonate, phosgene or diphosgene.

The compound (XI), which is used as a starting material in the above reaction, can be synthesized for example by the following method.

(Descriptions will be given below with regard to the individual cases in which X is O, S and NH, respectively.)

The compound of the formula:

[wherein $R^{2a}$ is an acyloxy group; $R^1$ is as defined hereinbefore] can be produced, for example, by the following reaction schema:

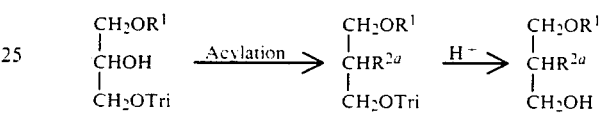

The compound of the formula:

[wherein $R^{2b}$ is an acylamino group; $R^1$ is as defined hereinbefore] can be produced, for example, by the following reaction schema:

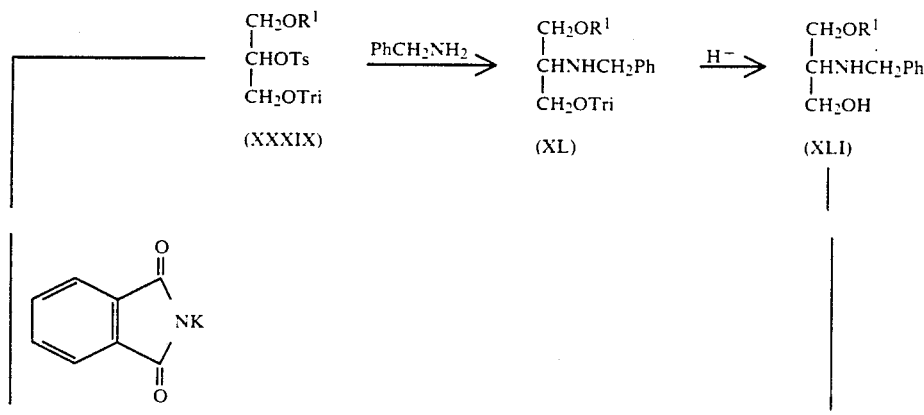

-continued

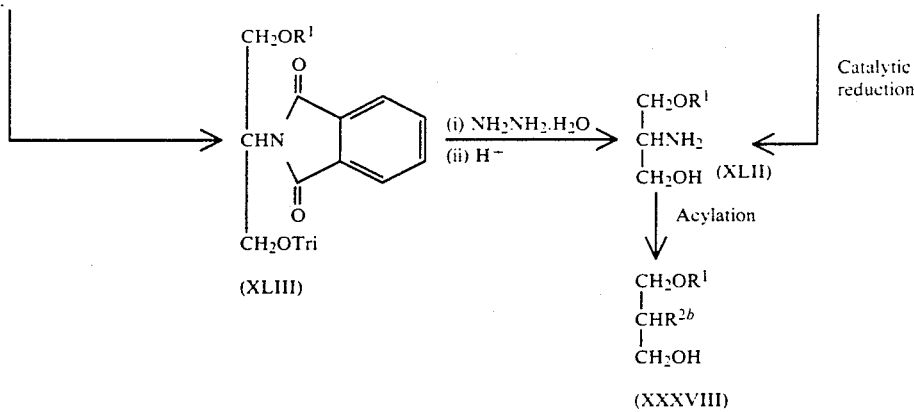

The compound of the formula:

(XLIV)

[wherein $R^{2c}$ is a group represented by the formula (III); $R^1$ is as defined hereinbefore] can be produced, for example, by the following reaction scheme.

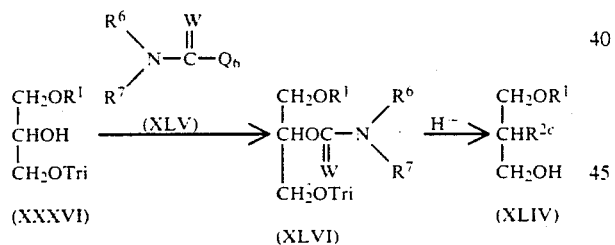

[wherein $Q_6$ is a halogen atom; other symbols are as defined hereinbefore].

The reaction (XXXVI)→(XLVI) can be preferably conducted without a solvent or in an inert solvent (e.g. toluene, benzene, chloroform, dichloromethane, tetrahydrofuran) at 0° to 150° C., preferably in the presence of a tertiary amine, such as pyridine, triethylamine, dimethyllaminopyridine. The reaction (XLVI)→(XLIV) can be allowed to proceed generally in water or an alcohol at +10° to +110° C. in the presence of an acid (e.g. hydrochloric acid, acetic acid).

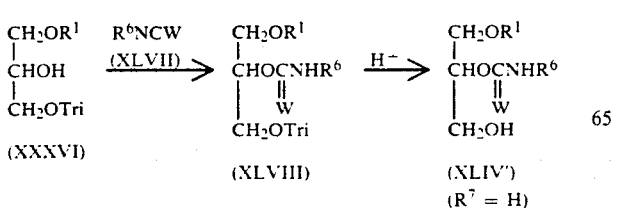

-continued

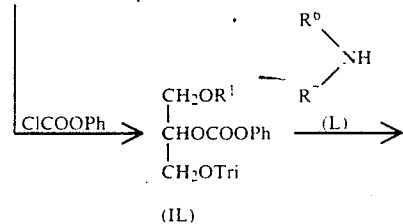

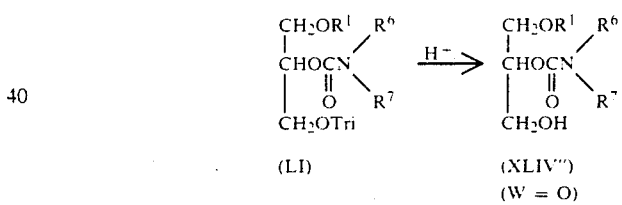

The reaction (XXXVI)→(XLVII) can be preferably conducted without a solvent or in an inert solvent, such as benzene, toluene, chloroform, dichloromethane and tetrahydrofuran at 0° to +150° C., preferably in the presence of a tertiary amine such as pyridine, and the reaction (XXXVI)→(LI) can be preferably conducted by reacting, without a solvent or in an inert solvent such as benzene, toluene, chloroform, dichloromethane and tetrahydrofuran at 0° to +150° C., the compound (L) with the compound (IL) as provided by reacting (XXXVI) and phenyl chlorocarbonate in an inert solvent (e.g., chloroform, dichloromethane, benzene, toluene, diethyl ether) at 0° to +100° C.

The compound of the formula:

(LII)

[wherein $R^{2d}$ is alkoxy or aralkyloxy; $R^1$ is as defined hereinbefore] can be produced, for example, by the following reaction schema.

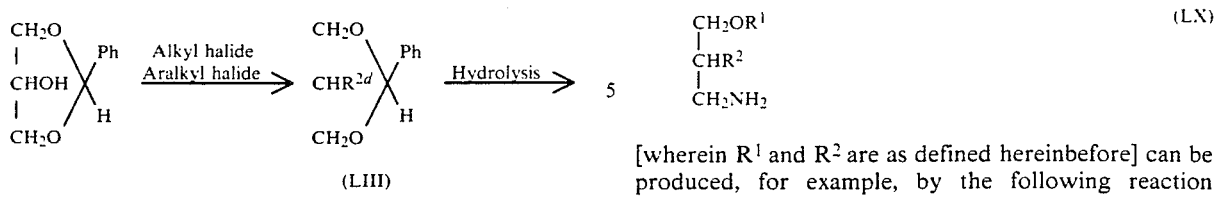

(LIII)

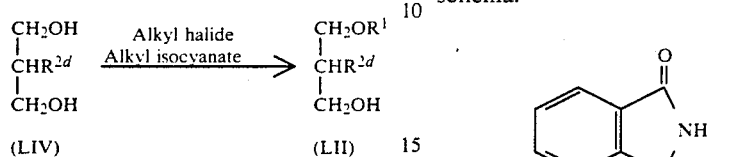

(LIV) (LII)

The compound of the formula:

(LV)

[wherein R¹ and R² are as defined hereinbefore] can be produced, for example, by the following reaction schema.

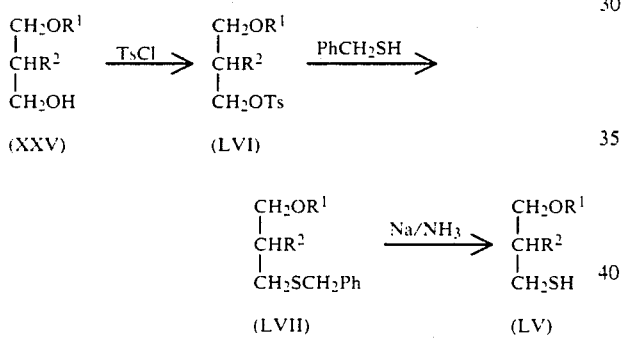

(XXV) (LVI)

(LVII) (LV)

The compound of the formula:

$$\begin{array}{l} CH_2OR^1 \\ | \\ CHR^{2e} \\ | \\ CH_2OH \end{array}$$ (LVIII)

[wherein R¹ is as defined hereinbefore, R²ᵉ is cyclic amino] can be produced, for example, by the following reaction schema.

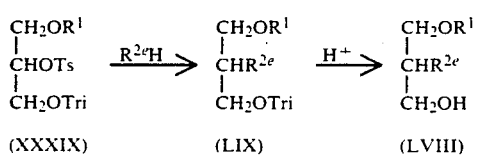

(XXXIX) (LIX) (LVIII)

In the above reaction schema, R²ᵉ is cyclic amino, and the symbols Ts and Tri are tosyl and trityl, respectively.

The compound of the formula:

$$\begin{array}{l} CH_2OR^1 \\ | \\ CHR^2 \\ | \\ CH_2NH_2 \end{array}$$ (LX)

[wherein R¹ and R² are as defined hereinbefore] can be produced, for example, by the following reaction schema.

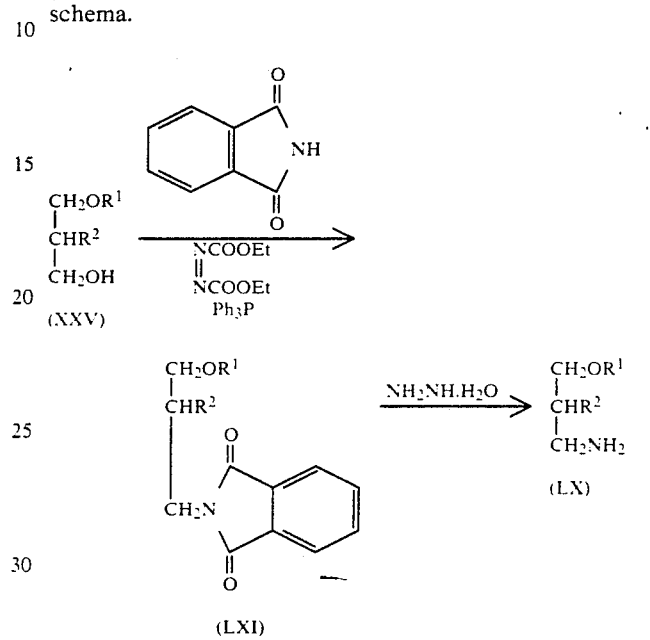

In each of the above reaction schema, the symbols Ph, Ts, Tri and DPPA are phenyl, tosyl, trityl and diphenylphosphorylazide, respectively.

With reference to the compounds to be used in each of the reactions, any compound having a group liable to affect adversely the reaction can be subjected to the reaction after having the said group protected with the per se known protective group (e.g., benzyl, tosyl, trityl, phthalimide, succinimide, benzyloxycarbonyl, tert-butoxycarbonyl, etc.), and thereafter subjected to the per se known deprotection reaction to give the objective compound.

The salt of the compound (I), in some instances, can be obtained for example by the above-mentioned processes for producing the compound (I) themselves, but can also be produced by adding an acid or base to the compound (I), if desired, and the form of a salt can be converted into another one with ion-exchange resin.

The invention will be further illustrated in more detail by the following Examples, Experiment Examples and Preparation Examples, which, however, are by no means of the present invention.

EXAMPLE 1

2-O-Benzyl-3-O-(2'-dimethylaminoethyl)carbamoyl-1-O-octadecylglycerol

In dichloromethane (12 ml) were dissolved 1.88 g (4.325 mmole) of 2-O-benzyl-1-O-octadecylglycerol and 0.684 g (8.65 mmole) of pyridine, and 0.745 g (4.756 mmole) of phenyl chlorocarbonate was added dropwise to the solution under ice-cooling, followed by stirring at room temperature for 1.5 hours. The reaction solution was washed with 1% sodium hydrogencarbonate solution, and the organic layer was dried over magnesium sulfate and the solvent was distilled off under reduced pressure. 457 mg (5.19 mmole) of asym.-dimethylethylenediamine was added to the resulting carbonate without being purified, and the mixture was heated at 70° C. for 5 hours and cooled. Purification was performed by silica gel column chromatography with chloroform-methanol (19:1) used as an eluent to give 2.37 g (yield of 99.8%) of the objective compound (colorless solid).

TLC [Silica gel, chloroform-methanol (14:1)] Rf=0.15.

NMR [90 MHz, CDCl$_3$] δ:0.83(3H), 1.28(32H), 2.20(6H), 2.37(2H), 3.23(2H), 3.42(2H), 3.53(2H), 3.76(1H), 4.20(2H), 4.68(2H), 5.27(1H), 7.32(5H).

IR [film] cm$^{-1}$: 3330, 2920, 2850, 2815, 1725, 1500, 1468, 1255, 1120, 1060.

EXAMPLE 2

2-O-Acetyl-3-O-[N-acetyl-N-(2'-dimethylaminoethyl)]carbamoyl-1-O-octadecylglycerol To a mixture of ethanol (5 ml) and 90% aqueous acetic acid solution (50 ml) were added 1.097 g (2 mmole) of the benzyl ether derivative as produced in Example 1 and 250 mg of 10% palladium carbon, and catalytic reduction was conducted at room temperature for 2 hours. After the completion of the reaction, the catalyst was filtered off, and the filtrate was concentrated under reduced pressure to give 958 mg of the crude alcohol derivative. After chloroform (10 ml), triethylamine (20 ml) and acetic anhydride (3 ml) were added to the alcohol derivative, the reaction solution was allowed to stand at room temperature for 13 hours and concentrated under reduced pressure. The residue was purified by silica gel column chromatography with ethyl acetate-acetone (5:1) used as an eluent to give 406 mg (yield of 37.4%) of the objective compound (colorless oil).

TLC [silica gel, chloroform-methanol (5:1)]: Rf=0.66.

NMR [90 MHz, CDCl$_3$] δ:0.88(3H), 1.27(32H), 2.10(3H), 2.23 (6H), 2.40(2H), 2.50(3H), 3.46(2H), 3.58(2H), 3.85(2H), 4.42(2H), 5.29(1H).

IR [film] cm$^{-1}$: 2924, 2850, 1745, 1710, 1460, 1372, 1234, 1180.

EXAMPLE 3

2-O-Acetyl-3-O-[N-acetyl-N-(2'-trimethylammonioethyl)]carbamoyl-1-O-octadecylglycerol iodide In 15 ml of ether were dissolved 355 mg (0.709 mmole) of the dimethylamino derivative as produced in Example 2 and 201 mg (1.418 mmole) of methyl iodide, and the solution was stirred at room temperature for 22 hours. The precipitate, which separated out under ice-cooling, was collected by filtration to give 424 mg (yield of 87.3%) of the objective compound (colorless powder).

TLC [silica gel, ethyl acetate-acetic acid-water (3:1:1)]: Rf=0.39.

NMR [90 MHz, CDCl$_3$] δ:0.89(3H), 1.27(32H), 2.12(3H), 2.52(3H), 3.47(2H), 3.48-3.71(11H), 3.80(2H), 4.22(2H), 4.51(2H), 5.42(1H).

IR [KBr] cm$^{-1}$: 3450, 2920, 2840, 1740, 1680, 1465, 1371, 1232, 1200.

EXAMPLE 4

2-O-Benzyl-1-O-octadecyl-3-O-(2'-trimethylammonioethyl)carbamoylglycerol iodide

In ether (20 ml) were dissolved 906 mg (1.651 mmole) of the dimethylamino derivative as produced in Example 1 and 469 mg (3.302 mmole) of methyl iodide, and the solution was stirred at room temperature for 2 days. The precipitate, which separated out, was collected by filtration to give 1.024 g (yield of 89.8%) of the objective compound (colorless powder).

TLC [silica gel, ethyl acetate-acetic acid-water (3:1:1)]: Rf=0.43.

NMR [90 MHz, CDCl$_3$+CD$_3$OD] δ:0.89(3H), 1.25(32H), 3.27(9H), 3.43(2H), 3.53(2H), 3.60-3.91(5H), 4.23(2H), 4.68(2H), 6.71(1H), 7.36(5H).

IR [KBr] cm$^{-1}$: 3355, 2927, 2850, 1730, 1539, 1473, 1255, 1130, 1044, 759, 703.

EXAMPLE 5

2-O-Benzyl-3-O-(2'-hydroxyethyl)carbamoyl-1-O-octadecylglycerol

In chloroform (10 ml) was dissolved the carbonate obtained from 1.739 g (4 mmole) of 2-O-benzyl-1-O-octadecylglycerol, 632 mg (8 mmole) of pyridine, 689 mg (4.4 mmole) of phenyl chlorocarbonate and dichloromethane (10 ml) by the same procedure as described in Example 1, and 293 mg (4.8 mmole) of ethanolamine was added to the solution, followed by refluxing for 21 hours. The reaction solution was concentrated under reduced pressure, and the residue was purified by silica gel column chromatography with hexane-ethyl acetate (1:1) used as an eluent to give 1.941 g (yield of 93.0%) of the objective compound (colorless solid).

TLC [silica gel, hexane-ethyl acetate (1:1)]: Rf=0.18

NMR [90 MHz, CDCl$_3$] δ:0.87(3H), 1.27(32H), 2.82(1H), 3.15-3.91(9H), 4.22(2H), 4.68(2H), 5.37(1H), 7.33(5H).

IR [KBr] cm$^{-1}$: 3335, 2920, 2850, 1700, 1530, 1465, 1259, 1119.

Elemental analysis, for C$_{31}$H$_{55}$NO$_5$: Calcd.: C, 71.36; H, 10.62; N, 2.68. Found: C, 71.65; H, 10.62; N, 2.40.

EXAMPLE 6

2-O-Benzyl-1-O-octadecyl-3-O-(2'-p-toluenesulfonyloxyethyl)carbamoylglycerol

In triethylamine (10 ml) was dissolved 1.841 g (3.528 mmole) of the alcohol derivative as produced in Example 5, and 0.875 g (4.587 mmole) of p-toluenesulfonyl chloride was added to the solution under ice-cooling, followed by stirring at room temperature for 12 hours. 5% aqueous hydrochloric acid solution was added to the reaction solution under ice-cooling, followed by extraction with chloroform. The organic layer was dried over magnesium sulfate, and the solvent was distilled off under reduced pressure. The residue was purified by silica gel column chromatography with hexane-ethyl acetate (2.5:1) used as an eluent to give 2.36 g (yield of 99.0%) of the objective compound (colorless oily material).

TLC [silica gel, hexane-ethyl acetate (2:1)]: Rf=0.29.

NMR [90 MHz, CDCl$_3$] δ:0.88(3H), 1.23(32H), 2.41(3H), 3.28-3.58(6H), 3.72(1H), 3.97-4.37(4H), 4.64(2H), 5.02(1H), 7.42-7.22(7H), 7.79(2H).

IR [film] cm$^{-1}$: 3330, 2930, 2850, 1728, 1600, 1525, 1465, 1365, 1255, 1190, 1180, 1120, 1100, 760.

EXAMPLE 7

2-O-Benzyl-3-O-(2'-bromoethyl)carbamoyl-1-O-octadecylglycerol

To dimethylformamide (22 ml) were added 2.360 g (3.491 mmole) of the tosyl derivative as produced in Example 6 and 0.732 g (6.983 mmole) of lithium bromide (LiBr.H$_2$O), and the mixture was heated at 60° C. for 2 hours. After cooling, water was added to the reaction solution, followed by extraction with ether. The organic layer was dried over magnesium sulfate, and the solvent was distilled off under reduced pressure. The residue was purified by silica gel column chromatography with hexane-ethyl acetate (4:1) used as an eluent to give 1.855 g (yield of 90.9%) of the objective compound (colorless solid).

TLC [silica gel, hexane-ethyl acetate (2:1)]: Rf=0.51.

NMR [90 MHz, CDCl$_3$] δ:0.87(3H), 1.26(32H), 3.29-3.92(9H), 4.22(2H), 4.66(2H), 5.06(1H), 7.30(5H).

IR [KBr] cm$^{-1}$: 3330, 2920, 2850, 1720, 1538, 1470, 1250, 1215, 1135, 1125.

Elemental analysis, for C$_{31}$H$_{54}$NO$_4$Br: Calcd.: C, 63.68; H, 9.31; N, 2.40. Found: C, 63.98; H, 9.37; N, 2.22.

EXAMPLE 8

2-O-Benzyl-1-O-octadecyl-3-O-(2'-thiazolioethyl)carbamoylglycerol bromide

To 511 mg (6.0 mmole) of thiazole was added 877 mg (1.5 mmole) of the bromo derivative as produced in Example 7, and the mixture was heated at 110° C. for 12 hours. The reaction solution was concentrated to dryness, and the residue was purified by silica gel column chromatography with chloroformmethanol (3:1) used as an eluent to give 781 mg (yield of 77.7%) of the objective compound (colorless powder).

TLC [silica gel, ethyl acetate-acetic acid-water (3:1:1)]: Rf=0.41.

NMR [90 MHz, CDCl$_3$] δ:0.88(3H), 1.26(32H), 3.42(2H), 3.50(2H), 3.60-4.38(5H), 4.67(2H), 4.92(2H), 6.85(1H), 7.35(5H), 8.04(1H), 8.43(1H), 10.62(1H).

IR [KBr] cm$^{-1}$: 3380, 2920, 2850, 1701, 1525, 1262, 1250, 1153, 1120, 1105, 753, 700.

EXAMPLE 9

3-O-(2'-Dimethylaminoethyl)carbamoyl-2-O-methyl-1-O-octadecylcarbamoylglycerol A 445 mg (4.8 mmole) portion of asym.-dimethylethylenediamine was added to the carbonate obtained from 1.607 g (4 mmole) of 2-O-methyl-1-O-octadecylcarbamoylglycerol, 632 mg (8 mmole) of pyridine, 689 mg (4.4 mmole) of phenyl chlorocarbonate and dichloromethane (10 ml) by the same procedure as described in Examples 1 and 5, and the mixture was heated at 70° C. for 5 hours. After cooling, the crude product was purified by silica gel column chromatography with chloroform-methanol (10:1) used as an eluent to give 1.895 g (yield of 91.9%) of the objective compound (colorless solid).

TLC [silica gel, chloroform-methanol (5:1)] Rf=0.31.

NMR [90 MHz, CDCl$_3$] δ:0.88(3H), 1.27(32H), 2.20(6H), 2.39(2H), 3.02-3.34(4H), 3.43(3H), 3.58(1H), 4.16(4H), 5.00(1H), 5.45(1H).

IR [KBr] cm$^{-1}$: 3300, 2925, 2850, 1695, 1535, 1470, 1280, 1260, 1115, 1075

EXAMPLE 10

2-O-Methyl-1-O-octadecylcarbamoyl-3-O-(2'-trimethylammonioethyl)carbamoylglycerol iodide In ether (20 ml) were dissolved 947 mg (1.836 mmole) of the dimethylamino derivative as produced in Example 9 and 339 mg (2.387 mmole) of methyl iodide, and the solution was stirred at room temperature for 2 days. The precipirate, which separated out, was collected by filtration, and purified by silica gel column chromatography with chloroform-methanol-water (65:25:1) used as an eluent to give 897 mg (yield of 74.3%) of the objective compound (colorless powder).

TLC [silica gel, chloroform-methanol-water (65:25:4)]: Rf=0.41.

NMR [90 MHz, CDCl$_3$] δ:0.89(3H), 1.27(32H), 3.13(2H), 3.50(12H), 3.62-4.52(9H), 5.50(1H), 6.81(1H).

IR [KBr] cm$^{-1}$: 3498, 2920, 2850, 1708, 1530, 1470, 1260.

EXAMPLE 11

3-O-(2'-Hydroxyethyl)carbamoyl-2-O-methyl-1-O-octadecylcarbamoylglycerol

In chloroform (16 ml) was dissolved the carbonate obtained from 3.213 g (8 mmole) of 2-O-methyl-1-O-octadecylcarbamoylglycerol, 1.266 g (16 mmole) of pyridine, 1.378 g (8.8 mmole) of phenyl chlorocarbonate and dichloromethane (20 ml) by the same procedure as described in Example 9, and 586 mg (9.6 mmole) of ethanolamine was added to the solution, followed by refluxing for 15 hours. The reaction solution was concentrated to dryness, and the residue was purified by silica gel column chromatography with hexane-ethyl acetate (1:4) used as an eluent to give 3.689 g (yield of 94.4%) of the objective compound (colorless solid).

TLC [silica gel, hexane-ethyl acetate (1:4)]: Rf=0.19.

NMR [90 MHz, CDCl$_3$] δ:0.88(3H), 1.28(32H), 3.00-3.80(10H), 4.18(4H), 5.13(1H), 5.69(1H).

IR [KBr] cm$^{-1}$: 3324, 2920, 2850, 1695, 1545, 1275.

Elemental analysis, for C$_{26}$H$_{52}$N$_2$O$_6$: Calcd.: C, 63.90; H, 10.72; N, 5.73. Found: C, 63.57; H, 10.73; N, 5.84.

EXAMPLE 12

2-O-Methyl-1-O-octadecylcarbamoyl-3-O-(2'-p-toluenesulfonyloxyethyl)carbamoylglycerol In triethylamine (22 ml) was dissolved 3.539 g (7.242 mmole) of the alcohol derivative as produced in Example 11, and 1.793 g (9.406 mmole) of p-toluenesulfonyl chloride was added to the solution under ice-cooling, followed by stirring at room temperature for 8 hours. The reaction solution was treated in the same manner as described in Example 6, and the resulting crude product was purified by silica gel column chromatography with hexane-ethyl acetate (1:1) used as an eluent to give 4.039 g (yield of 86.8%) of the objective compound (colorless solid).

TLC [silica gel, hexane-ethyl acetate (1:1)] Rf=0.21.

NMR [90 MHz, CDCl$_3$] δ:0.88(3H), 1.25(32H), 2.43(3H), 3.16(2H), 3.30-3.70(6H), 4.13(6H), 4.86(1H), 5.25(1H), 7.32(2H), 7.80(2H).

IR [KBr] cm$^{-1}$: 3380, 2920, 2850, 1695, 1540, 1468, 1365, 1260, 1180.

EXAMPLE 13

3-O-(2'-Bromoethyl)carbamoyl-2-O-methyl-1-O-octadecylcarbamoylglycerol

In dimethylformamide (37 ml) were dissolved 3.886 g (6.045 mmole) of the tosyl derivative as produced in Example 12 and 1.267 g (12.089 mmole) of lithium bromide (LiBr.H$_2$O), and the solution was heated at 60° C. for 42 hours. The reaction solution was treated in the same manner as described in Example 7, and the resulting crude product was purified by silica gel column chromatography with hexane-ethyl acetate (3:2) used as an eluent to give 3.10 g (yield of 93%) of the objective compound (colorless solid).

TLC [silica gel, hexane-ethyl acetate (1:1)] Rf=0.45

NMR [90 MHz, CDCl$_3$] δ:0.88(3H), 1.27(32H), 3.17(2H), 3.34–3.73(8H), 4.18(4H), 4.90(1H), 5.40(1H).

IR [KBr] cm$^{-1}$: 3330, 2920, 2850, 1695, 1540, 1470, 1310, 1275, 1152, 1120.

Elemental analysis, for C$_{26}$H$_{51}$N$_2$O$_5$Br: Calcd.: C, 56.61; H, 9.32; N, 5.08. Found: C, 56.38; H, 9.28; N, 4.95.

EXAMPLE 14

2-O-Methyl-1-O-octadecylcarbamoyl-3-O-(2'-thiazolioethyl)carbamoylglycerol bromide To 1.103 g (2 mmole) of the bromo derivative as produced in Example 13 was added 681 mg (8 mmole) of thiazole, and the mixture was heated at 110° C. for 12 hours. The reaction solution was concentrated to dryness, and the residue was purified by silica gel column chromatography with chloroform-methanol-water (65:25:1) used as an eluent to give 847 mg (yield of 66.5%) of the objective compound (pale brown powder).

TLC [silica gel, ethyl acetate-acetic acid-water (3:1:1)] Rf=0.34.

NMR [90 MHz, CDCl$_3$] δ:0.88(3H), 1.25(32H), 3.12(2H), 3.40(3H), 3.68(1H), 3.82(2H), 4.15(4H), 5.06(2H), 5.48(1H), 7.06(1H), 8.38(1H), 8.68(1H), 10.74(1H).

IR [KBr] cm$^{-1}$: 3370, 2920, 2850, 1702, 1534, 1470, 1255.

EXAMPLE 15

2-O-Benzyl-1-O-(2'-trimethylammonioethyl)carbamoyl-3-O-octadecylglycerol chloride In dichloromethane (6 ml) were dissolved 2.67 g (6.14 mmole) of 2-O-benzyl-3-O-octadecylglycerol and 0.84 g (8 mmole) of 2-chloroethyl isocyanate, and the solution was stirred at room temperature overnight. The reaction solution was concentrated to dryness under reduced pressure, and the residue was purified by silica gel column chromatography with chloroform used as an eluent. The resulting chloro derivative was further dissolved in 20% trimethylamine-toluene (20 ml), and the solution was heated in a sealed tube at 160° C. for 24 hours. The reaction solution was concentrated to dryness under reduced pressure, and acetone (10 ml) was added to the residue, followed by washing to give 2.0 g (yield of 85.0%) of a colorless powder.

TLC [silica gel, n-BuOH-AcOH-water (4:1:1)] Rf=0.36.

IR [KBr] cm$^{-1}$: 3350, 2930, 2850, 1725, 1465, 1250, 1120, 1060.

EXAMPLE 16

1-O-(2'-Trimethylammonioethyl)carbamoyl-3-O-octadecylglycerol chloride

In 70% acetic acid (30 ml) was dissolved 2.0 g (3.34 mmile) of the benzyl derivative as produced in Example 15, and 200 mg of 10% palladium carbon was added to the solution, followed by vigorous stirring under a hydrogen stream for 4 hours. The insoluble material was filtered off, and the filtrate was concentrated to dryness under reduced pressure. The residue was recrystallized when hot from chloroform-acetone (1:1) (10 ml) to give 1.7 g (yield of 100%) of a colorless crystalline powder.

TLC [silica gel, n-BuOH-AcOH-water (4:1:1)]: Rf=0.21.

IR [KBr] cm$^{-1}$: 3400, 2935, 2850, 1710, 1530, 1480, 1270, 1130, 960.

EXAMPLE 17

2-O-Methylcarbamoyl-1-O-(2'-trimethylamminoethyl)-carbamoyl-3-O-octadecylglycerol chloride In a mixture of pyridine (2 ml) and chloroform (1 ml) was dissolved 200 mg (0.39 mmole) of the hydroxy derivative as obtained in Example 16, and 600 mg of methyl isocyanate was added to the solution, followed by stirring at 50° C. overnight. The reaction solution was concentrated to dryness under reduced pressure, and the residue was recrystallized when hot from a mixture of chloroform (0.5 ml) and acetone (5 ml) to give 198 mg of the objective compound (colorless powder).

TLC [silica gel, n-BuOH-AcOH-water (4:1:1)]: Rf=0.21

IR [KBr] cm$^{-1}$: 3400, 2920, 2850, 1720, 1540, 1470, 1270, 1155, 1125, 770.

NMR [60 MHz, CDCl$_3$] δ:0.88(3H), 1.25(32H), 2.78(3H), 3.10–4.00(15H), 4.28(4H), 4.07(1H), 5.72(2H).

Elemental analysis, for C$_{29}$H$_{60}$N$_3$O$_5$Cl.3H$_2$O: Calcd.: C, 56.15; H, 10.72; N, 6.77. Found: C, 56.25; H, 10.40; N, 6.99.

EXAMPLE 18

1-Octadecyloxy-2-acetamido-3-(2'-dimethylaminoethyl)carbamoyloxypropane (i) 3-Octadecyloxy-2-aminopropane-1-ol Benzylamine (12 ml) was added to 8.67 g (11.7 mmole) of 1-O-octadecyl-2-O-tosyl-3-O-tritylglycerol, and after the mixture was heated at 120° C. for 8 hours, the excessive benzylamine was distilled off under reduced pressure. n-Hexane was added to the residue, and the insoluble material was filtered off, followed by concentrating the filtrate to dryness. 70% acetic acid (50 ml) was added to the residue, and the mixture was stirred under heating for 2 hours. After cooling, the crystals which separated out were filtered off, and palladium-carbon was added to the filtrate to conduct catalytic reduction, followed by filtration and concentration to dryness. The residue was dissolved in chloroform, and the solution was washed with aqueous sodium hydrogencarbonate solution, dried and concentrated to dryness, followed by purification by silica gel chromatography (eluent; chloroform-methanol (10:1)) to give 3.13 g (yield of 78%) of the objective compound (colorless powder).

R [KBr] cm$^{-1}$: 3330, 2925, 2850, 1580, 1470, 1370, 1120, 1070, 1040, 722.

NMR [90 MHz, CDCl₃] δ:0.87(3H,t), 1.25(32H,m), 3.05(1H,m), 3.41(2H,d), 3.42(2H,t), 3.5–3.7(2H,m).

(ii) 3-Octadecyloxy-2-acetamidopropan-1-ol

In chloroform (35 ml) were dissolved 857.5 mg (2.5 mmole) of the above-mentioned aminoalcohol derivative, 197 mg (2.5 mmole) of acetyl chloride and 305 mg (2.5 mmole) of 4-dimethylaminopyridine, and the solution was stirred at room temperature for 28 hours. The reaction solution was concentrated to dryness under reduced pressure, and the residue was purified by silica gel chromatography (eluent; chloroform-methanol, 20:1) to give 868 mg (yield of 90%) of the objective compound (colorless powder).

NMR [90 MHz, CDCl₃] δ:0.87(3H,t), 1.25(32H,m), 2.01(3H,s), 2.9(1H), 3.43(2H,t), 3.60(2H,d), 3.77(2H,m), 4.05(1H,m), 6.1(1H,br,NH).

(iii) 1-Octadecyloxy-2-acetamido-3-(2'-dimethylaminoethyl)carbamoyloxypropane

In dichloromethane (10 ml) were dissolved 385 mg (1 mmole) of the above-mentioned alcohol derivative and 158 mg (2 mmole) of pyridine, and 156 mg (1 mmole) of phenyl chlorocarbonate was added to the solution under ice-cooling. After stirring at room temperature for 1 hour, chloroform and water were added to the reaction solution, and the organic layer was separated, washed with dilute hydrochloric acid and aqueous sodium hydrogencarbonate solution successively, dried and concentrated to give the phenyl carbonate derivative. The carbonate was dissolved in asym.-dimethylethylenediamine (1.5 ml), and the solution was heated at 70° C. for 4 hours. The reaction solution was subjected to silica gel chromatography (eluent; chloroform-methanol, 5:1) and purified to give 360 mg (yield of 72%) of the objective compound (colorless powder).

IR [KBr] cm⁻¹: 3330, 3280, 2920, 2850, 1695, 1655, 1462, 1378, 1310, 1278, 1130.

NMR [90 MHz, CDCl₃] δ:0.87(3H,t), 1.25(32H,m), 1.97(3H,s), 2.20(6H,s,NMe₂), 2.38(2H,t), 3.1–3.5(4H,m), 3.40(2H,t), 4.0(1H,m), 4.17(2H,m), 5.2, 6.0(NH).

TLC [silica gel, CHCl₃-MeOH, 5:1]: Rf=0.20.

EXAMPLE 19

1-Octadecyloxy-2-acetamido-3-(2'-trimethylammonioethyl)carbamoyloxypropane iodide In a mixture of ether (30 ml) and chloroform (3 ml) was dissolved 300 mg (0.6 mmole) of the dimethylamino derivative as obtained in Example 18, and 420 mg (3 mmole) of methyl iodide was added to the solution, followed by stirring at room temperature for 1 day. The powder, which separated out, was collected by filtration and washed with a mixture of ether-chloroform to give 258 mg (yield of 67%) of the objective compound (colorless powder).

IR [KBr] cm⁻¹: 3470, 3620, 2920, 2850, 1715, 1665, 1645, 1530, 1470, 1380, 1260, 1120, 970, 920, 720.

NMR [90 MHz, CDCl₃] δ:0.87(3H,t), 1.25(32H,m), 2.00(3H,s,NHAc), 3.43(9H,s,N⁺Me₃), 3.40(2H,t,CH₂O), 3.65–4.0(4H,m), 4.0–4.35(3H,m,>CHN,CH₂OCO).

EXAMPLE 20

1-Octadecyloxy-2-acetamido-3-[N-acetyl-N-(2'-trimethylammonioethyl)]carbamoyloxypropane iodide (i) 1-Octadecyloxy-2-phthalimido-3-phenoxycarbonyloxypropane In dichloromethane (20 ml) was dissolved 950 mg (2 mmole) of 3-octadecyloxy-2-phthalimidopropan-1-ol, and 316 mg (4 mmole) of pyridine and 313 mg (2 mmole) of phenyl chlorocarbonate were added to the solution under ice-cooling. After stirring under ice-cooling for 15 minutes and at room temperature for 45 minutes, chloroform (40 ml) was added to the reaction solution, and the mixture was washed with dilute hydrochloric acid and aqueous sodium hydrogencarbonate solution successively, dried and concentrated to give the objective carbonate derivative.

3-Octadecyloxy-2-phthalimidopropan-1-ol used as the starting material was synthesized by reacting 3-octadecyloxy-2-aminopropane-1-ol as produced in Example 18-(i) with carboethoxyphthalimide.

(ii) 1-Octadecyloxy-2-amino-3-(2'-N,N-dimethylaminoethyl)carbamoyloxypropane

The above-mentioned carbonate derivative was dissolved in asym.-dimethylethylenediamine (2 ml), and the solution was stirred at 70° C. for 4 hours. n-Hexane was added to the reaction solution, and the insoluble material was filtered off. The filtrate was purified by silica gel chromatography eluent; chloroform-methanol-water, (65:25:4) to give 466 mg of the objective compound (colorless solid).

TLC [silica gel, CHCl₃-MeOH-water, 65:25:4]: Rf=0.2.

IR [KBr] cm⁻¹: 3330, 2920, 2850, 1690, 1550, 1465, 1278, 1130, 1030.

(iii) 1-Octadecyloxy-2-acetamido-3-[N-acetyl-N-(2'-dimethylaminoethyl)]carbamoyloxypropane In chloroform (3 ml) was dissolved 175 mg of the 2-amino derivative as obtained by the above-mentioned procedure, and triethylamine (1 ml) and acetic anhydride (0.3 ml) were added to the solution, followed by stirring at room temperature overnight. The reaction solution was concentrated, and the residue was purified by silica gel chromatography (eluent chloroform-methanol, 10:1) to give 148 mg of the objective compound (colorless solid).

IR [KBr] cm⁻¹: 3280, 2920, 2850, 1740, 1715, 1655, 1550, 1470, 1370, 1300, 1250, 1185, 1130, 980.

NMR [90 MHz, CDCl₃] δ:0.87(3H,t), 1.25(32H,m), 2.00(3H,s), 2.45(6H,s), 2.50(3H,s), 2.68(2H,t), 3.3–3.6(4H,m), 3.98(2H,t), 4.15–4.60(3H,m).

(iv) 1-Octadecyloxy-2-acetamido-3-[N-acetyl-N-(2'-trimethylammonioethyl)]carbamoyloxypropane iodide In ether (5 ml) was dissolved 138 mg of the above-mentioned compound, and 109 mg of methyl iodide was added to the solution, followed by stirring at room temperature overnight. The solid, which separated out upon cooling, was collected by filtration to give 141 mg of the objective compound (colorless powder).

IR [KBr] cm⁻¹: 3450, 2920, 2850, 1755, 1670, 1540, 1470, 1375, 1260, 1205, 1165.

NMR [90 MHz, CDCl₃] δ:0.87(3H,t), 1.25(32H,m), 2.03(3H,s), 2.52(3H,s), 3.45(9H,s), 3.3–3.7(4H,m), 3.7–4.0(2H,m), 4.07–4.3(2H,m), 4.4–4.6(3H,m).

EXAMPLE 21

2-O-Dimethylcarbamoyl-1-O-octadecyl-3-O-(N-2'-trimethylammonioethyl)carbamoylglycerol bromide (i) 3-O-(2'-Bromoethyl)carbamoyl-1-O-octadecylglycerol A 40 ml portion of 90% aqueous acetic acid solution was added to 949 mg (1.623 mmole) of 2-benzyl-3-O-(2'-bromoethyl)carbamoyl-1-octadecylglycerol (as synthesized in Example 7) and 250 mg of 10% Pd/C, and hydrogenolysis was carried out at room temperature for 2 hours. After the catalyst was filtered out, the filtrate was concentrated under reduced pressure, and a mixture of n-hexane-ethyl acetate (2:1) was added to the residue. The precipitate was collected by filtration to give 785 mg (97.8 g.) of the alcohol derivative (colorless powder).

TLC [silica gel, n-hexane-ethyl acetate (1:1)]: Rf=0.43.

NMR [90 MHz, CDCl$_3$] δ:0.88(3H,t), 1.24(32H,s), 2.85(1H,br.d.), 3.31–3.72(8H,m), 4.00(1H,m), 4.17(2H,m), 5.33(1H,br.).

IR [KBr] cm$^{-1}$: 3415, 3305, 2920, 2850, 1698, 1562, 1465, 1285.

(ii) 3-O-(2'-Bromoethyl)carbamoyl-2-O-dimethylcarbamoyl-1-O-octadecylglycerol

In 3 ml of methylene chloride were dissolved 495 mg (1 mmole) of the alcohol derivative as obtained in (i) and 158 mg (2 mmole) of pyridine, and a CH$_2$Cl$_2$ solution (1 ml) of 172 mg (1.1 mmole) of phenyl chloroformate was added to the solution under ice-cooling, followed by stirring at room temperature for 2.5 hours. Treatment by the conventional method was conducted to yield 811 mg of the crude carbonate.

1ml of 20% dimethylamine/toluene solution was added to a toluene solution (4 ml) of the crude carbonate, and the mixture was allowed to stand at room temperature for 2 hours. The reaction solution was concentrated under reduced pressure, and the resulting crude product was purified by column chromatography [silica gel: 25 g; eluent: n-hexane-ethyl acetate (2:1)] to give 473 mg (83.6%) of the dimethylcarbamoyl derivative (colorless solid).

TLC [silica gel; n-hexane-ethyl acetate (2:1)]: Rf=0.22.

NMR [90 MHz, CDCl$_3$] δ:0.88(3H,t), 1.24(32H,s), 2.90(6H,s), 3.33–3.72(8H,m), 4.30(2H,m), 5.05(1H,quint), 5.22(1H,br.).

IR [KBr] cm$^{-1}$: 3325, 2920, 2850, 1710, 1545, 1470, 1262, 1200, 1123.

(iii) 2-O-Dimethylcarbamoyl-1-O-octadecyl-3-O-(2'-trimethylammonioethyl)carbamoylglycerol bromide In 5 ml of 20% trimethylamine/toluene solution was dissolved 175 mg (0.309 mmole) of the dimethylcarbamoyl derivative as obtained in (ii), and the solution was allowed to stand at room temperature for 4 days. The precipitate, which separated out, was collected by filtration to give 167 mg (83.8%) of the objective compound (colorless powder).

TLC [silica gel; ethyl acetate-acetic acid-water (3:1:1)] Rf=0.47.

NMR [90 MHz, CDCl$_3$] δ:0.88(3H,t), 1.23(32H,s), 2.89(6H,s), 3.30–3.63(13H,m), 3.80(4H,br.), 4.28(2H,m), 5.03(1H,br.), 6.79(1H,br.).

IR [KBr] cm$^{-1}$: 3275, 2920, 2850, 1719, 1693, 1555, 1472, 1405, 1275, 1200.

EXAMPLE 22

2-O-Dimethylcarbamoyl-1-O-octadecyl-3-O-(2'-thiazolioethyl)carbamoylglycerol bromide A 2 ml portion of thiazole was added to 235 mg (0.415 mmole) of the dimethylcarbamoyl derivative as obtained in Example 21-(ii), and the mixture was heated under a nitrogen atmosphere at 110° C. for 7 hours. The reaction solution was concentrated under reduced pressure, and the crude product was purified by column chromatography [silica gel: 13 g; an eluent: chloroform-methanol-water (65:25:1)] to give 212 mg (78.5%) of the objective compound (colorless powder).

TLC [silica gel; ethyl acetate-acetic acid-water (3:1:1): Rf=0.52.

NMR [90 MHz, CDCl$_3$] δ:0.87(3H,t), 1.23(32H,s), 2.90(6H,s), 3.30–3.60(4H,m), 3.64–4.40(4H,m), 5.02(3H,br.), 6.80(1H,br.t), 8.29(1H,br.), 8.72(1H,br.), 10.77(1H,br.).

IR [KBr] cm$^{-1}$: 3400, 2920, 2850, 1703, 1530, 1470, 1400, 1260, 1200.

EXAMPLE 23

2-O-Acetyl-1-O-octadecyl-3-O-(2'-trimethylammonioethyl)carbamoylglycerol bromide (i) 2-O-Acetyl-3-O-(2'-bromoethyl)carbamoyl-1-O-octadecylglycerol.

In 3 ml of CHCl$_3$ was dissolved 124 mg (0.25 mmole) of the alcohol derivative as synthesized in Example 21-(i), and after 2.5 ml of pyridine and 0.4 ml of acetic anhydride were added to the solution, the mixture was allowed to stand at room temperature for 13 hours. Ethyl ether was added to the reaction solution, and the mixture was washed with 5% aqueous NaHCO$_3$ solution and 5% aqueous hydrochloric acid solution successively. The organic layer was dried over magnesium sulfate, and the solvent was distilled off under reduced pressure. The resulting crude product was purified by column chromatography [silica gel: 4 g: an eluent; n-hexane; ethyl acetate (4:1)] to give 117 mg (87.2%) of the acetyl derivative (colorless syrup).

TLC [silica gel; n-hexane-ethyl acetate (2:1)]: Rf=0.44.

NMR [90 MHz, CDCl$_3$] δ:0.89(3H,t), 1.27(32H,s), 2.08(3H,s), 3.35–3.73(8H,m), 4.28(2H,m), 5.04–5.41(2H,m).

IR [film] cm$^{-1}$: 3325, 2910, 2840, 1735, 1700, 1530, 1465, 1368, 1125.

(ii) 2-O-Acetyl-1-O-octadecyl-3-O-(2'-trimethylammonioethyl)carbamoylglycerol bromide.

In 2 ml of toluene was dissolved 115 mg (0.214 mmole) of the acetyl derivative as synthesized in (i), and after 4 ml of 20% trimethylamine/toluene solution was added to the solution, the mixture was allowed to stand at room temperature for 2 days. The solvent was distilled off under reduced pressure, and the residue was reprecipitated from chloroform-ethyl ether to give 120 mg (94.1%) of the objective compound (colorless powder).

TLC [silica gel; ethyl acetate-acetic acid-water (3:1:1)]: Rf=0.62.

NMR [90 MHz, CDCl$_3$] δ:0.87(3H,t), 1.25(32H,s), 2.08(3H,s), 3.32–3.97(17H,m), 4.30(2H,m), 5.20(1H,m), 6.82(1H,m).

IR [KBr] cm$^{-1}$: 3450, 2920, 2850, 1730, 1538, 1470, 1265, 1240, 1128.

EXAMPLE 24

3-O-[N-Acetyl-N-(2'-dimethylaminoethyl)]carbamoyl-2-O-methyl-1-O-octadecylcarbamoylglycerol hydrochloride In 15 ml of CHCl$_3$ was dissolved 202 mg (0.392 mmole) of 3-O-(2'-dimethylaminoethyl)carbamoyl-2-O-methyl-1-O-octadecylcarbamoylglycerol (as synthesized in Example 9), and after 4 ml of triethylamine and 0.4 ml of acetic anhydride were added to the solution, the mixture was allowed to stand at room temperature for 4 days. The reaction solution was concentrated under reduced pressure, and 1% aqueous NaHCO$_3$ solution was added to the residue, followed by extraction with CHCl$_3$. The organic layer was dried over potassium carbonate, and the solvent was distilled off under reduced pressure. The resulting crude product was purified by column chromatography [silica gel; 7 g; an eluent acetate-acetone (1:1)] to give 206 mg (94.2%) of a colorless oily material. 11.5 mg of this "Free Base" was dissolved in ethyl ether, and the solution was treated with hydrogen chloride gas under ice-cooling to give 13 mg of the objective compound (colorless solid).

"Free Base"

TLC [silica gel; chloroform-methanol (5:1)]: Rf=0.62.

NMR [90 MHz, CDCl$_3$] δ:0.89(3H,t), 1.25(32H,s), 2.25(6H,s), 2.43(2H,t), 2.48(3H,s), 3.13(2H,q), 3.43(3H,s), 3.62(1H,quint), 3.86(2H,t), 4.20(2H,d), 4.30(2H,d.d.), 5.61(1H,br.).

IR [film] cm$^{-1}$: 3350, 2925, 2850, 1738, 1710, 1690, 1535, 1465, 1370, 1245, 1180.

EXAMPLE 25

3-O-[N-Acetyl-N-(2'-trimethylammonioethyl)]carbamoyl-2-O-methyl-1-O-octadecylcarbamoylglycerol iodide In 9 ml of ethyl ether was dissolved 206 mg (0.369 mmole) of the compound as synthesized in Example 24, and after 157 mg (1.108 mmole) of methyl iodide was added to the solution, the mixture was stirred at room temperature for 3 days under shielding from light. The precipitate, which separated out, was collected by filtration to give 231 mg (89.5%) of the objective compound (colorless powder).

TLC [silica gel; ethyl acetate-acetic acid-water (3:1:1)]: Rf=0.36.

NMR [90 MHz, CDCl$_3$] δ:0.88(3H,t), 1.25(32H,s), 2.53(3H,s), 3.14(2H,q), 3.48(3H,s), 3.56(9H,s), 3.67–3.92(3H,m), 4.22(4H,m), 4.40(2H,m), 5.03(1H,br.).

IR [KBr] cm$^{-1}$: 3420, 2930, 2855, 1742, 1700, 1538, 1475, 1380, 1260, 1205, 1170, 1143.

EXAMPLE 26

3-O-(2'-Dimethylaminoethyl)carbamoyl-2-O-dimethylcarbamoyl-1-O-octadecylglycerol hydrochloride In 5 ml of methylene chloride were dissolved 306 mg (0.736 mmole) of 2-O-dimethylcarbamoyl-1-O-octadecylglycerol and 116 mg (1.472 mmole) of pyridine, and after 127 mg (0.810 mmole) of phenyl chloroformate was added to the solution, the mixture was stirred at room temperature for 40 minutes. After treatment by the conventional procedure, the resulting crude carbonate, together with 162 μl (1.472 mmole) of asym.-dimethylethylenediamine, was heated at 70° C. for 14 hours. After cooling, the curde product was purified by column chromatography [silica gel: 20 g; an eluent: n-hexane-ethyl acetate (1:4) and chloroform-methanol (10:1)] to give 374 mg (95.9%) of the objective compound "Free Base" (colorless oil). 38 mg of this "Free Base" was dissolved in ethyl ether, and the solution was treated with hydrogen chloride gas under ice-cooling to give 41 mg of the hydrochloride (colorless powder).

"Free Base"

TLC [Silica gel; chloroform-methanol (5:1)]:Rf=0.30.

NMR [90 MHz, CDCl$_3$] δ:0.88(3H,t), 1.23(32H,s), 2.22(6H,s), 2.40(2H,t), 2.90(6H,s), 3.42(2H,t), 3.57(2H,d), 4.28(2H,m), 5.05(1H,quint.), 5.18(1H,br.).

IR [film] cm$^{-1}$: 3330, 2930, 2850, 1710, 1465, 1400, 1259, 1193.

EXAMPLE 27

3-O-[N-Acetyl-N-(2'-dimethylaminoethyl)]carbamoyl-2-O-dimethylcarbamoyl-1-O-octadecylglycerol hydrochloride In 20 ml of chloroform was dissolved 374 mg (0.706 mmole) of the dimethylamino derivative as synthesized in Example 26 and after 8 ml of triethylamine and 1.5 ml of acetic anhydride were added to the solution, the mixture was allowed to stand at room temperature for 19 hours. The reaction solution was concentrated under reduced pressure, followed by treatment by the same procedure as described in Example 24, and the resulting crude product was purified by column chromatography [silica gel: 13 g; an eluent: ethyl acetate-acetone (1:1)] to give 360 mg (89.2%) of the objective compound "Free Base" (colorless oil). 19 mg of this Free Base was dissolved in ethyl ether, and the solution was treated with hydrogen chloride gas under ice-cooling to give 21 mg of the objective compound (colorless powder).

"Free Base"

TLC [silica gel; chloroform-methanol (5:1)]: Rf=0.62.

NMR [90 MHz, CDCl$_3$] δ:0.88(3H,t), 1.22(32H,s), 2.22(6H,s), 2.39(2H,t), 2.47(3H,s), 2.90(6H,s), 3.42(2H,t), 3.58(2H,d), 3.82(2H,t), 4.44(2H,m), 5.13(1H,quint.).

IR [film] cm$^{-1}$: 2925, 2850, 2815, 2752, 1740, 1706, 1460, 1395, 1370, 1242, 1190, 1175, 1155, 1120, 1095.

EXAMPLE 28

3-O-[N-Acetyl-N-(2'-trimethylammonioethyl)]carbamoyl-2-O-dimethylcarbamoyl-1-O-octadecylglycerol iodide In 12 ml of ethyl ether was dissolved 337 mg (0.589 mmole) of the dimethylamino derivative as synthesized in Example 27, and after 251 mg (1.768 mmole) of methyl iodide was added to the solution, the mixture was stirred at room temperature for 3 days under shielding from light. The reaction solution was concentrated under reduced pressure to give 361 mg (85.9%) of the objective compound (colorless powder).

TLC [silica gel; ethyl acetate-acetic acid-water (3:1:1)]: Rf=0.31.

NMR [90 MHz, CDCl$_3$] δ:0.88(3H,t), 1.25(32H,s), 2.50(3H,s), 2.90(6H,s), 3.44(2H,t), 3.53(9H,s) and (2H,d), 3.80(2H,br.t), 4.23(2H,br.t), 4.47(2H,m), 5.24(1H,m).

IR [KBr] cm$^{-1}$: 2925, 2850, 1750, 1705, 1475, 1405, 1379, 1270, 1210.

EXAMPLE 29

2-O-Acetyl-3-O-[N-acetyl-N-(2'-benzylmethylammonioethyl)]carbamoyl-1-O-octadecylglycerol chloride To 200 mg (0.368 mmole) of 2-O-acetyl-3-O-[N-acetyl-N-(2'-dimethylaminoethyl)]carbamoyl-1-O-octadecylglycerol (as synthesized in Example 2) was added 127 μl (1.105 mmole) of benzyl chloride, followed by heating at 70° C. for 2 hours. After cooling, the reaction product was washed with n-pentane to give 247 mg (100%) of the objective compound (colorless powder).

TLC [silica gel; chloroform-methanol (5:1)]: Rf=0.26.

NMR [90 MHz, CDCl₃] δ:0.87(3H,t), 1.23(32H,s), 2.05(3H,s), 2.46(3H,s), 3.28-3.83(12H,m), 4.10-4.58(4H,m), 5.08(2H,s), 5.32(1H,m), 7.47, 7.73(5H,m).

IR [KBr] cm⁻¹: 3430, 2925, 2850, 1745, 1690, 1475, 1378, 1250.

EXAMPLE 30

2-O-Methyl-3-O-[N-methyl-N-(2'-dimethylaminoethyl)]carbamoyl-1-O-octadecylcarbamoylglycerol hydrochloride A 158 μl (1.179 mmole) of N,N,N'-trimethylethylenediamine was added to 568 mg of the crude carbonate synthesized from 377 mg (0.938 mmole) of 2-O-methyl-1-O-octadecylcarbamoylglycerol, 162 mg (1.032 mmole) of phenyl chloroformate, 148 mg (1.876 mmole) of pyridine and 3 ml of methylene chloride by the conventional method, followed by heating at 72° C. for 3 hours. After cooling, the crude product was purified by column chromatography [silica gel: 23 g; an eluent: n-hexane-ethyl acetate (1:4) and chloroform-methanol (8:1)] to give 520 mg (98.2%) of the objective compound (Free Base) (colorless oil). 20 mg of this "Free Base" was dissolved in ethyl ether, and the solution was treated with hydrogen chloride gas under ice-cooling to give 21 mg of the hydrochloride (colorless syrup).

"Free Base"

TLC [silica gel; chloroform-methanol (7:1)]: Rf=0.45.

NMR [90 MHz, CDCl₃] δ:0.87(3H,t), 1.26(32H,s), 2.25(6H,s), 2.42(2H,t), 2.92(3H,s), 3.16(2H,q), 3.37(2H,t), 3.45(3H,s), 3.60(1H,quint.), 4.18(4H,d), 5.00(1H,br.).

IR [film] cm⁻¹: 3345, 2920, 2850, 2770, 1706, 1535, 1466, 1405, 1255, 1195, 1135.

EXAMPLE 31

2-O-Methyl-3-O-[N-methyl-N-(2'-trimethylammonioethyl)]carbamoyl-1-O-octadecylcarbamoylglycerol iodide In 20 ml of ethyl ether was dissolved 540 mg (1.019 mmole) of the dimethylamino derivative as synthesized in Example 30, and 434 mg (3.058 mmole) of methyl iodide was added to the solution, followed by stirring at room temperature for 3 days. The reaction solution was concentrated under reduced pressure, and the residue was reprecipitated from a mixture of acetone/ether to give 607 mg (90.4%) of the objective compound (colorless powder).

TLC [silica gel; chloroform-methanol (5:1)]: Rf=0.08.

NMR [90 MHz, CDCl₃] δ:0.88(3H,t), 1.25(32H,s), 3.10(3H,s) and (2H,m), 3.42(3H,s), 3.60(9H,s), 3.62-4,33(9H,m), 4.87(1H,br.).

IR [KBr] cm⁻¹: 3450, 2925, 2852, 1702.

EXAMPLE 32

2-O-Methyl-1-O-octadecylcarbamoyl-3-O-(2'-pyrolidinoethyl)carbamoylglycerol hydrochloride A 154 μl (1.2 mmole) of N-(2-aminoethyl)pyrrolidine was added to 578 mg of the crude carbonate synthesized from 402 mg (1 mmole) of 2-O-methyl-1-O-octadecylcarbamoylglycerol, 172 mg (1.1 mmole) of phenyl chloroformate, 158 mg (2 mmole) of pyridine and 3 ml of methylene chloride by the conventional method, followed by heating at 72° C. for 8 hours. After cooling, the curde product was purified by column chromatography [silica gel: 23 g; an eluent: n-hexane-ethyl acetate (1:4) and chloroform-methanol (8:1)] to give 503 mg (92.8%) of the objective compound (Free Base) (colorless solid). 20 mg of this Free Base was dissolved in ethyl ether under ice-cooling, and the solution was treated with hydrogen chloride gas to give 21 mg of the hydrochloride (colorless powder).

"Free Base"

TLC [Silica gel; chloroform-methanol (7:1)] Rf=0.23.

NMR [90 MHz, CDCl₃] δ:0.88(3H,t), 1.24(32H,s), 1.77(4H,m), 2.40-2.70(6H,m), 3.03-3.38(4H,m), 3.43(3H,s), 3.58(1H,quint.), 4.16(4H,d), 4.98(1H,br.), 5.53(1H,br.).

IR [KBr] cm⁻¹: 3320, 2920, 2850, 1695, 1535, 1469, 1275.

EXAMPLE 33

3-O-[N-Acetyl-N-(2'-pyrrolidinoethyl)]carbamoyl-2-O-methyl-1-O-octadecylcarbamoylglycerol hydrochloride In 10 ml of chloroform was dissolved 370 mg (0.683 mmole) of the compound as synthesized in Example 32, and after 8 ml of triethylamine and 1.5 ml of acetic anhydride were added to the solution, the mixture was allowed to stand at room temperature for 3 days. The reaction solution was concentrated under reduced pressure, and after the residue was treated in the same manner as described in Example 24, the resulting crude product was purified by column chromatography [silica gel: 14 g; an eluent: ethyl acetate-acetone (1:2)] to give 398 mg (99.8%) of the objective compound (Free Base) (colorless syrup). 20 mg of this Free Base was dissolved in ethyl ether, and the solution was treated with hydrogen chloride gas under ice-cooling to give 21 mg of the hydrochloride (colorless syrup).

"Free Base"

TLC [silica gel; ethyl acetate-acetone (1:3)] Rf=0.17.

NMR [90 MHz, CDCl₃] δ:0.87(3H,t), 1.26(32H,s), 1.64-1.89(4H,m), 2.49(3H,s), 2.59(6H,m), 3.12(2H,q), 3.44(3H,s), 3.62(1H,quint.), 3.89(2H,t), 4.21(2H,d), 4.30(2H,d.d.), 5.52(1H,br.).

IR [film] cm⁻¹: 3340, 2925, 2852, 1738, 1710, 1535, 1470, 1375, 1356, 1255, 1225, 1198, 1163.

EXAMPLE 34

3-O-[N-Acetyl-N-(2'-N-methylpyrrolidinioethyl)]carbamoyl-2-O-methyl-1-O-octadecylcarbamoylglycerol iodide In 13 ml of ethyl ether was dissolved 378 mg (0.647 mmole) of the compound (Free Base) as synthesized in Example 33, and after 276 mg (1.942 mmole) of methyl iodide was added to the solution, the mixture was stirred at room temperature for 4 days under shielding from light. The solvent is distilled off under reduced pressure to give 428 mg (91.1%) of the objective compound (colorless powder).

TLC [silica gel; chloroform-methanol (5:1)] Rf=0.12.

NMR [90 MHz, CDCl$_3$] δ:0.88(3H,t), 1.26(32H,s), 2.32(4H,m), 2.52(3H,s), 3.12(2H,q), 3.39(3H,s), 3.47(3H,s), 3.68–4.06(7H,m), 4.22(4H,m), 4.42(2H,m), 5.17(1H,br.).

IR [KBr] cm$^{-1}$: 3415, 2920, 2850, 1738, 1700, 1532, 1468, 1372, 1220, 1179.

EXAMPLE 35

3-O-[N-Acetyl-N-(2'-N-methylpyrrolidinioethyl)]carbamoyl-2-O-octadecylcarbamoylglycerol hydrochloride In a mixture of methanol-water (7:3) was dissolved 2.694 g of the compound as synthesized in Example 34, and the solution was treated with 120 ml of IRA-410 [Cl$^-$] to give 2.341 g of the objective compound (colorless powder).

TLC [silica gel; ethyl acetate-acetic acid-water (3:1:1)]: Rf=0.75.

NMR [90 MHz, CDCl$_3$] δ:0.88(3H,t), 1.26(32H,s), 2.29(4H,m), 2.50(3H,s), 3.12(2H,q), 3.40(3H,s), 3.45(3H,s), 3.62–4.08(7H,m), 4.22(4H,m), 4.41(2H,m), 5.04(1H,br.).

IR [KBr] cm$^{-1}$: 3420, 2920, 2850, 1738, 1700, 1538, 1472, 1380, 1220, 1180.

EXAMPLE 36

2-O-Methyl-3-O-[2'(N-methylpyrrolidinio)ethyl]carbamoyl-1-O-octadecylcarbamoylglycerol iodide In 4 ml of ethyl ether was dissolved 95 mg (0.175 mmole) of the compound (Free Base) as synthesized in Example 32, and after methyl iodide (0.562 mmole) was added to the solution, the mixture was allowed to stand at room temperature for 3 days under shielding from light. The reaction solution was concentrated under reduced pressure, and the resulting product was reprecipitated from a mixture of ethyl ether/pentane to give 115 mg (96.1%) of the objective compound (colorless powder).

TLC [silica gel; chloroform-methanol (5:1)] Rf=0.08.

NMR [90 MHz, CDCl$_3$] δ:0.88(3H,t), 1.26(32H,s), 2.28(4H,m), 3.12(2H,q), 3.36(3H,br.s), 3.42(3H,s), 3.49–4.01(9H,m), 4.03–4.32(4H,m), 5.18(1H,br.), 6.60(1H,br.).

IR [KBr] cm$^{-1}$: 3400, 2915, 2850, 1705, 1530, 1468, 1265.

EXAMPLE 37

2-O-methyl-1-O-octadecylcarbamoyl-3-O-(2'-piperidinoethyl)carbamoylglycerol hydrochloride To 578 mg of the crude carbonate as synthesized in the same manner as described in Example 32 was added 175 μl (1.2 mmole) of N-(2-aminoethyl)piperidine, followed by heating at 72° C. for 10 hours. After cooling, the crude product was purified by column chromatography [silica gel; 25 g; an elument; n-hexane-ethyl acetate (1:4) and chloroform-methanol (8:1)] to give 555 mg (100%) of the objective compound (Free Base) (colorless solid). 21 mg of this Free Base was dissolved in ethyl ether, and the solution was treated with hydrogen chloride gas under ice-cooling to give 22 mg of the hydrochloride.

"Free Base"

TLC [silica gel; chloroform-methanol (7:1)]: Rf=0.39.

NMR [90 MHz, CDCl$_3$] δ:0.86(3H,t), 1.24(32H,s), 1.41–1.73(6H,m), 2.27–2.53(6H,m), 3.01–3.37(4H,m), 3.43(3H,s), 3.58(1H,quint.), 4.18(4H,d), 4.82(1H,br.), 5.38(1H,br.).

IR [KBr] cm$^{-1}$: 3330, 2920, 2850, 1692, 1540, 1370, 1273.

EXAMPLE 38

3-O-[N-Acetyl-N-(2'-pipieridinoethyl)]carbamoyl-2-O-methyl-1-O-octadecylcarbamoylglycerol hydrochloride.

In 15 ml of chloroform was dissolved 565 mg (1.017 mmole) of the compound (Free Base) as synthesized in Example 37, and after 12 ml of triethylamine and 2.3 ml of acetic anhydride were added to the solution, the mixture was allowed to stand at room temperature for 4 days, followed by heating under reflux for 24 hours. After cooling, the reaction was concentrated under reduced pressure, and after the residue was treated in the same manner as described in Example 24, the resulting crude product was purified by column chromatography [silica gel: 21 g; an eluent; ethyl acetate-acetone (2:1)] to give 456 mg (75.0%) of the objective compound (Free Base). 35 mg of this Free Base was dissolved in ethyl ether, and the solution was treated with hydrogen chloride gas under ice-cooling to give 37 mg of the hydrochloride.

"Free Base"

TLC [silica gel; ethyl acetate-acetate (1:1)] Rf=0.27.

NMR [90 MHz, CDCl$_3$] δ:0.88(3H,t), 1.26(32H,s), 1.46(6H,m), 2.41(6H,m), 2.47(3H,s), 3.15(2H,q), 3.45(3H,s), 3.62(1H,quint.). 3.88(2H,t), 4.21(2H,d), 4.30(2H,dd), 5.20(1H,br.).

IR [film] cm$^{-1}$: 3360, 2930, 2853, 1740, 1710, 1530, 1473, 1375, 1250, 1195, 1130.

EXAMPLE 39

3-O-[N-Acetyl-N-methylpiperidinioethyl)]carbamoyl-2-O-methyl-O-octadecylcarbamoylglycerol iodide.

In 8 ml of ethyl ether was dissolved 421 mg (0.704 mmole) of the compound (Free Base) as synthesized in Example 38, and after 300 mg (2.113 mmole) of methyl iodide was added to the solution, the mixture was stirred at room temperature for 2 days, under shielding from light. The reaction solution was concentrated under reduced pressure to give 467 mg (89.7%) of the objective compound (colorless powder).

TLC (silica gel; chloroform-methanol (5:1)]: Rf=0.14.

NMR [90 MHz, CDCl$_3$] δ:0.88(3H,t), 1.24(32H,s), 1.89(6H,m), 2.55(3H,s), 3.12(2H,q), 3.42(3H,s), 3.48(3H,s), 3.59–3.99(7H,m), 4.22(4H,m), 4.42(2H,m), 5.17(1H,br.).

IR [KBr] cm$^{-1}$: 3450, 2925, 2852, 1740, 1705, 1530, 1475, 1180, 1252, 1223.

EXAMPLE 40

2-O-Methyl-3-O-[2'-(N-methylpiperidinio)ethyl]carbamoyl-1-O-octadecylcarbamoylglycerol iodide In 1.5 ml of ethyl ether was dissolved 23 mg (0.041 mmole) of the compound (Free Base) as synthesized in Example 37, and after 18 mg (0.124 mmole) of methyl iodide was added to the solution, the mixture was allowed to stand at room temperature for 3 days under shielding from light. The reaction solution was cooled with ice, and the precipitate which separated out was collected by filtration to give 27 mg (94.3%) of the objective compound (colorless powder).

TLC[silica gel: ethyl acetate-acetic acid-water (3:1:1)]: Rf=0.31.

NMR [90 MHz, CDCl$_3$] δ:0.87(3H,t), 1.25(32H,s), 1.88(6H,m), 3.12(2H,q), 3.40(3H,s), 3.43(3H,s), 3.50-3.93(9H,m), 4.13(4H,m), 4.98(1H,br.), 6.53(1H,br.).

IR [KBr] cm$^{-1}$: 3380, 2920, 2848, 1710, 1530, 1465, 1250.

EXAMPLE 41

2-O-Methyl-3-O-(2'-morpholinoethyl)carbamoyl-1-O-octadecylcarbamoylglycerol hydrochloride A 162 μl (1.2 mmole) portion of N-(2-aminoethyl)-morpholine was added to 578 mg of the crude carbonate as synthesized in the same manner as described in Example 32, followed by stirring at 72° C. for 10 hours. After cooling, the crude produce was purified by column chormatography [silica gel: 30 g; an eluent n-hexane-ethyl acetate (1:4) and chloroform-methanol (16:1)] to give 538 mg (96.5%) of the objective compound (Free Base) (colorless solid). 19 mg of this Free Base was dissolved in ethyl ether, and the solution was treated with hydrogen chloride gas under ice-cooling to give 20 mg of the hydrochloride.

"Free Base"

TLC [silica gel; chloroform-methanol (7:1)] Rf=0.59.

NMR [90 MHz, CDCl$_3$] δ:0.88(3H,t), 1.25(32H,s), 2.38-2.58(6H,m), 3.03-3.38(4H,m), 3.45(3H,s), 3.49-3.80(5H,m), 4.19(4H,d), 4.81(1H,br.), 5.28(1H,br.).

IR [KBr] cm$^{-1}$: 3325, 2920, 2850, 1692, 1548, 1468, 1272, 1120.

EXAMPLE 42

2-O-Methyl-3-O-[2'-(N-methylmorpholinio)ethyl]carbamoyl-1-O-octadecylcarbamoylglycerol iodide.

In 1.5 ml of ethyl ether was dissolved 22 mg (0.039 mmole) of the compound (Free Base) as synthesized in Example 41, and after 17 mg (0.118 mmole) of methyl iodide was added to the solution, the mixture was allowed to stand at room temperature for 14 days under shielding from light. The reaction solution was concentrated under reduced pressure to give 27 mg (98.9%) of the objective compound (colorless powder).

TLC [silica gel; ethyl acetate-acetic acid-water (3:1:1)]: Rf=0.32.

NMR [90 MHz, CDCl$_3$] δ:0.88(3H,t), 1.26(32H,s), 3.12(2H,q), 3.42(3H,s), 3.59(3H,s), 3.66-4.33(13H,m), 5.05(1H,br.), 6.60(1H,br.).

IR [KBr] cm$^{-1}$: 3410, 2925, 2855, 1713, 1530, 1475, 1260.

EXAMPLE 43

3-O-[N-Methoxycarbonyl-N-(2'-N-methylpyrrolidinioethyl)]carbamoyl-2-O-methyl-1-O-octadecylcarbamoylglycerol iodide (i) 3-O-[N-Methoxycarbonyl-N-(2'-pyrrolidinoethyl)-]carbamoyl-2-O-methyl-1-O-octadecylcarbamoylglycerol.

In 10 ml of methylene chloride were dissolved 813 mg (1.5 mmole) of the compound (Free Base) as synthesized in Example 32 and 202 mg (2 mmole) of triethylamine, and 155 μl (2 mmole) of methyl chloroformate was added to the solution under ice-cooling, followed by stirring at room temperature for 3 hours. 1% Aqueous NaHCO$_3$ solution was added to the reaction solution, followed by extraction with chloroform, and the organic layer was dried over magnesium sulfate. The solvent was distilled off under reduced pressure, and the resulting crude product was purified by column chromatography [silica gel: 30 g; an eluent: ethyl acetate-acetone (1:2)] to give 734 mg (81.6%) of the objective compound (colorless oil).

TLC [silica gel; chloroform-methanol (5:1)] Rf=0.41.

NMR [90 MHz, CDCl$_3$] δ:0.85(3H,t), 1.26(32H,s), 1.72(4H,m), 2.38-2.78(6H,m), 3.14(2H,q), 3.43(3H,s), 3.62(1H,quint.), 3.80(3H,s), 3.83(2H,t), 4.08-4.45(4H,m), 5.08(1H,br.).

IR [film] cm$^{-1}$: 3370, 2930, 2860, 1800, 1760, 1735, 1705, 1540, 1475, 1455, 1362, 1298, 1255, 1225, 1200, 1150.

(ii) 3-O-[N-Methoxycarbonyl-N-(2'-N-methylpyrrolidinioethyl)]carbamoyl-2-O-methyl-1-O-octadecylcarbamoylglycerol iodide In 20 ml of ethyl ether was dissolved 694 mg (1.567 mmole) of the compound as synthesized in (i), and after 493 mg (3.471 mmole) of methyl iodide was added to the solution, the mixture was allowed to stand at room temperature for 4 days under shielding from light. The precipitate was collected by filtration to give 757 mg (65.1%) of the objective compound [colorless powder].

TLC [silica gel; chloroform-methanol (5:1)] Rf=0.16.

NMR [90 MHz, CDCl$_3$] δ:0.88(3H,t), 1.28(32H,s), 2.32(4H,m), 3.12(2H,q), 3.40(3H,s), 3.46(3H,s), 3.70-4.03(10H,m), 4.20(4H,m), 4.38(2H,m), 5.07(1H,br.).

IR [KBr] cm$^{-1}$: 3430, 2925, 2850, 1795, 1750, 1721, 1700, 1535, 1470, 1380, 1250, 1115.

EXAMPLE 44

3-O-[N-Acetyl-N-(1'-ethylpyrrolidin-2'-yl)methyl]carbamoyl-2-O-methyl-1-O-octadecylcarbamoylglycerol hydrochloride (i) 3-O-[N-(1'-Ethylpyrrolidin-2'-yl)methyl]carbamoyl-2-O-methyl-1-O-octadecylcarbamoylglycerol A 347 μl (2.4 mmole) portion of 2-(aminomethyl)-1-ethylpyrrolidine was added to the crude carbonate as synthesized in the same manner as described in Example 32 from 803 mg (2 mmole) of 2-O-methyl-1-O-octadecylcarbamoylglycerol, 345 mg (2.2 mmole) of phenyl chloroformate, 317 mg (4 mmole) of pyridine and 5 ml of methylene chloride, followed by heating under a nitrogen atmosphere at 80° C. for 16 hours. After cooling, the crude product was purified by column chromatography [silica gel: 50 g; an eluent: n-hexane-ethyl acetate (1:4) and chloroform-methanol (10:1)] to give 1.066 g (95.9%) of the objective compound (colorless solid).

TLC [silica gel; chloroform-methanol (10:1)] Rf=0.22.

NMR [90 MHz, CDCl$_3$] δ:0.88(3H,t), 1.10(3H,t), 1.28(32H,s), 1.75(4H,m), 2.10-2.98(5H,m), 3.19(4H,m), 3.46(3H,s), 3.60(1H,quint.), 4.18(4H,d), 4.98(1H,br.t), 5.42(1H,br.).

IR [KBr] cm$^{-1}$: 3330, 2925, 2855, 1695, 1540, 1472, 1260.

(ii) 3-[N-Acetyl-N-(1'-ethylpyrrolidin-2'-yl)methyl]-carbamoyl-2-O-methyl-1-O-octadecylcarbamoylglycerol hydrochloride In 20 ml of chloroform was dissolved 921 mg (1.657 mmole) of the compound as synthesized in (i), and 4 ml of acetic anhydride and 20 ml of triethylamine were added to the solution, followed by heating under reflux at 80° to 100° C. for 24 hours. After cooling, the reaction solution was concentrated under reduced pressure, and 1% aqueous $NaHCO_3$ solution was added to the residue, followed by extraction with chloroform. The organic layer was dried over magnesium sulfate, and the solvent was distilled off under reduced pressure. The resulting crude product was purified by column chromatography [silica gel: 50 g; an elument: ethyl acetate-acetone (1:1)] to give 948 mg (95.7%) of the objective compound (Free Base) (colorless oil). 50 mg of this Free Base was dissolved in ethyl ether, and the solution was treated with hydrogen chloride gas under ice-cooling to give 53 mg of the hydrochloride.

"Free Base"

TLC [silica gel; chloroform-methanol (5:1)]: $Rf=0.56$.

NMR [90 MHz, $CDCl_3$] δ:0.88(3H,t), 1.10(3H,t), 1.26(32H,s), 1.72(4H,m), 2.16–2.98(5H,m), 2.50(3H,s), 3.15(2H,q), 3.45(3H, s), 3.64(1H,m), 3.80(2H,d), 4.08–4.40(4H,m), 4.92(1H,br.).

IR [film] $cm^{-1}$: 3330, 2930, 2850, 1740, 1710, 1535, 1470, 1375, 1250, 1220, 1175, 1140.

EXAMPLE 45

3-O-[N-Acetyl-N-(1'-ethyl-1'-methylpyrrolidinio-2'-yl)methyl]carbamoyl-2-O-methyl-1-O-octadecylcarbamoylglycerol iodide In 12 ml of ethyl ether was dissolved 607 mg (1.015 mmole) of the compound (Free Base) as synthesized in Example 44-ii), and after 432 mg (3.046 mmole) of methyl iodide was added to the solution, the mixture was allowed to stand at room temperature for 5 days under shielding from light. Petroleum ether was added to reaction solution, and the precipirtate, which separated out, was collected by filtration to give 622 mg (82.8%) of the objective compound (colorless powder).

TLC [silica gel: chloroform-methanol (3:1)] $Rf=0.47$.

NMR [90 MHz, $CDCl_3$] δ:0.88(3H,t), 1.26(32H,s), 1.48(3H,t), 1.90–2.40(4H,m), 2.53(3H,s), 3.12(5H,m), 3.47(3H,s), 3.60–4.56(12H,m), 5.15(1H,br.).

IR [KBr] $cm^{-1}$: 3450, 2920, 2850, 1755–1705, 1470, 1260, 1220, 1200.

EXAMPLE 46

2-O-Methyl-3-O-[(1'-methylpyridinio-2'-yl)methyl]carbamoyl-1-O-octadecylcarbamoylglycerol iodide (i) 2-O-Methyl-3-O-[N-(2'-pyridylmethyl)]carbamoyl-1-O-octadecylcarbamoylglycerol To 567 mg of the crude carbonate synthesized from 402 mg (1 mmole) of 2-O-methyl-1-O-octadecylcarbamoylglycerol, 172 mg (1.1 mmole) of phenyl chloroformate, 158 mg (2 mmole) of pyridine and 3 ml of methylene chloride were added 122 μl (1.2 mmole) of 2-(aminomethyl)pyridine and 1 ml of chloroform, followed by heating under reflux for 12 hours. The reaction solution was concentrated under reduced pressure, and the resulting crude product was purified by column chromatography [silica gel; 20 g: an eluent: n-hexane-ethyl acetate (1:3)] to give 454 mg (84.7%) of the objective compound (colorless solid).

TLC [silica gel; n-hexane-ethyl acetate (1:3)] $Rf=0.21$.

NMR [90 MHz, $CDCl_3$] δ:0.87(3H,t), 1.25(32H,s), 3.15(2H,q), 3.43(3H,s), 3.59(1H,quint.), 4.18(4H,m), 4.50(2H,d), 4.90(1H,br,), 6.00(1H,br.), 7.22(2H,m), 7.65(1H,m), 8.52(1H,m).

IR [KBr] $cm^{-1}$: 3320, 2925, 2850, 1695, 1535, 1470, 1260, 1250.

(ii) 2-O-Methyl-3-O-[(1'-methylpyridinio-2'-yl)methyl]carbamoyl-1-O-octadecylcarbamoylglycerol iodide In 0.5 ml of chloroform and 6 ml of ethyl ether was dissolved 170 mg (0.317 mmole) of the compound as synthesized in (i), and after 135 mg (0.952 mmole) of methyl iodide was added to the solution. The mixture was allowed to stand at room temperature for 14 days under shielding from light. The precipitate, which separated out, was collected by filtration to give 123 mg (57.1%) of the objective compound (pale yellow powder).

TLC [silica gel: chloroform-methanol(3:1)] $Rf=0.20$.

NMR [90 MHz, $CDCl_3$] δ:0.87(3H,t), 1.24(32H,s), 3.12(2H,q), 3.42(3H,s), 3.59(1H,quint.), 4.15(4H,m), 4.55(3H,s), 4.89(2H,d), 5.20(1H,br.), 7.04(1H,br.), 7.85–8.23(2H,m), 8.46(1H,t), 9.19(1H,d).

IR [KBr] $cm^{-1}$: 3340, 2920, 2850, 1698, 1635, 1530, 1470, 1260.

EXAMPLE 47

2-O-Acetyl-3-O-octadecyl-1-O-[N-acetyl-N-(2'-trimethylammonioethyl)]carbamoylglycerol chloride In 20 ml of 70% methanol was dissolved 342 mg (0.5 mmole) of the iodide as obtained in Example 3, and the solution was passed through IRA-410($Cl^-$) ion exchange resin and washed with a small amount of 70% methanol. The eluate and washing were combined and concentrated to dryness under reduced pressure, and the residue was recrystallized from 5 ml of ethyl ether to give 289 mg (yield of 97.5%) of a colorless powder.

Elemental analysis, for $C_{31}H_{61}N_2O_6Cl \cdot H_2O$: Calcd.: C, 60.91; H, 10.39; N, 4.58; Cl, 5.80. Found: C, 60.98; H, 11.03; N, 4.54; Cl, 5.82.

EXAMPLE 48

2-O-Methyl-3-O-octadecylcarbamoyl-1-O-[N-acetyl-N-(2'-trimethylammonioethyl)]carbamoylglycerol chloride A 350 mg (0.5 mmole) portion of the iodide as obtained in Example 25 was treated in the same manner as described in Example 47, and recrystallization from a mixture of 1 ml of acetone and 4 ml of ether was conducted to yield 297 mg (yield of 97.7%) of colorless crystals.

Elemental analysis, for $C_{31}H_{61}N_2O_6Cl \cdot H_2O$: Calcd.: C, 59.45; H, 10.30; N, 6.71; Cl, 5.66. Found: C, 59.56; H, 10.58; N, 6.71; Cl, 5.68.

EXAMPLE 49

1-O-(3-Dimethylaminopropyl)carbamoyl-2-O-methyl-3-O-octadecylcarbamoylglycerol

To 1.5 g (2.9 mmole) of 1-O-octadecylcarbamoyl-2-O-methyl-3-O-phenoxycarbonylglycerol was added 355 mg (3.48 mmole) of asym-dimethyldiaminopropane, and the mixture was heated at 70° C. for 5 hours. The reaction solution was adsorbed onto silica gel (28 g), and elution was performed with chloroform-methanol (19:1). The eluate was concentrated to dryness under reduced pressure, and the residue was recrystallized from acetone to give 1.53 g (yield of 100%) of colorless crystals.

TLC [silica gel; n-BuOH, AcOH, H$_2$O (4:1:1)] Rf=0.31.

IR (KBr) cm$^{-1}$: 3330, 2920, 2850, 2750, 1690, 1530, 1470, 1275, 1260, 1250, 1230, 1140, 1100, 1070, 1040.

NMR (60 MC, CDCl$_3$) δ:0.88(3H), 1.25(32H), 2.22(6H), 2.37(2H), 3.20(4H), 3.45(3H), 3.72(1H), 4.17(4H), 4.67(1H), 5.57(1H).

EXAMPLE 50

2-O-Methyl-3-O-octadecylcarbamoyl-1-O-(3-trimethylammoniopropyl)carbamoylglycerol iodide In 1 ml of methyl iodide was dissolved 450 mg (0.85 mmole) of the dimethylaminopropyl derivative as obtained in Example 49, and the reaction solution was allowed to stand at room temperature for 18 hours and concentrated to dryness under reduced pressure. The residue was recrystallized from 1 ml of acetone and 4 ml of ether to give 507 mg (yield of 88.8%) of a colorless powder.

TLC [silica gel; n-BuOH, AcOH, H$_2$O (4:1:1)] Rf=0.27.

IR (KBr) cm$^{-1}$: 3300, 2920, 2850, 1695, 1430, 1465, 1260, 1150.

NMR (60 MC, CDCl$_3$) δ:0.87(3H), 1.25(32H), 2.18(2H), 3.17(4H), 3.38(9H), 3.43(3H), 3.63(1H), 3.78(2H), 4.15(4H), 5.07(1H), 6.07(1H).

Elemental analysis, for C$_{30}$H$_{62}$N$_2$O$_5$I.1.2H$_2$O: Calcd.: C, 51.97; H, 9.36; N, 6.06. Found: C, 51.93; H, 9.38; N, 6.31.

EXAMPLE 51

1-O-(N-Dimethylaminoethyl-N-propionyl)carbamoyl-2-O-methyl-3-O-octadecylcarbamoylglycerol In 1 ml of dichloromethane was dissolved 516 mg (1 mmole) of the dimethylaminoethyl derivative as obtained in Example 9, and after 185 mg (2 mmole) of propionyl chloride and 395 mg of pyridine were added to the solution, the mixture was allowed to stand at room temperature for 64 hours. 10 ml of water containing 500 mg of sodium hydrogencarbonate and 9 ml of dichloromethane were added to the reaction solution, and the mixture was stirred for a while and allowed to stand. The dichloromethane layer was separated out, dried over anhydrous sodium sulfate and concentrated to dryness under reduced pressure, and the residue was purified by silica gel (10 g). Development with chloroform-methanol (19:1) yielded 560 mg (yield of 98.1%) of a colorless oil.

TLC [silica gel, CHCl$_3$, MeOH (5:1)] Rf=0.25 (single spot).

IR [film] cm$^{-1}$: 3350, 2930, 2850, 1735, 1710, 1675, 1520, 1460, 1370, 1260, 1175.

NMR (60 MC, CDCl$_3$) δ:0.90(3H), 1.25(32H), 1.17(3H), 2.28(6H), 2.43(2H), 2.66(2H), 3.08(2H), 3.43(3H), 3.72(1H), 3.92(2H), 4.18(2H), 4.30(2H), 5.33(1H).

EXAMPLE 52

2-O-Methyl-3-O-octadecylcarbamoyl-1-O-[N-propionyl-N-(2'-trimethylammonioethyl)]carbamoylglycerol iodide In 2 ml of methyl iodide was dissolved 560 mg (0.98 mmole) of the propionyl derivative as obtained in Example 51, and the solution was allowed to stand at room temperature overnight, followed by concentration to dryness under reduced pressure. The residue was recrystallized from 8 ml of ether to give 453 mg (yield of 64.7%) of pale yellow crystalline powder.

TLC [silica gel; n-BuOH, AcOH, H$_2$O (4:1:1)] Rf=0.24.

IR (KBr) cm$^{-1}$: 3320, 2920, 2850, 1700, 1530, 1470, 1370, 1270, 1200, 1150.

NMR (60 MC, CDCl$_3$) δ:0.83(3H), 1.13(3H), 1.28(32H), 2.93 (2H), 3.09(2H), 3.47(3H), 3.55(9H), 3.80(1H), 3.90(2H), 4.22(2H), 4.30(2H), 4.40(2H), 5.07(1H).

Elemental analysis, for C$_{32}$H$_{64}$N$_3$O$_6$I.2.6H$_2$O: Calcd.: C, 50.53; H, 9.17; N, 5.52. Found: C, 50.49; H, 8.89; N, 5.97.

EXAMPLE 53

1-O-(N-Dimethylaminoethyl-N-methylcarbamoyl)carbamoyl-2-O-methyl-3-O-octadecylcarbamoylglycerol In a mixture of 1 ml of methyl isocyanate and 1 ml of chloroform was dissolved 500 mg (0.97 mmole) of the dimethylaminoethyl derivative as obtained in Example 9, and the reaction solution was stirred at 60° C. for 6 hours and concentrated to dryness under reduced pressure. The residue was purified by silica gel column chromatography with chloroform-methanol (9:1) as an eluent to give 500 mg (yield of 90.0%) of a colorless oil.

TLC [silica gel; CHCl$_3$, MeOH (5:1)] Rf=0.70, single spot.

IR (film) cm$^{-1}$: 3350, 2930, 2850, 1725, 1700, 1525, 1470, 1420, 1205, 1240, 1190.

NMR (60 MC, CDCl$_3$) δ:0.88(3H), 1.25(32H), 2.27(6H), 2.50(2H), 2.83(3H), 3.22(2H), 3.43(3H), 3.60(1H), 3.88(2H), 4.17(2H), 4.27(2H), 5.77(1H), 8.42(1H).

EXAMPLE 54

2-O-Methyl-1-O-[N-methylcarbamoyl-N-(2'-trimethylammonioethyl)carbamoyl-3-O-octadecylcarbamoylglycerol chloride A 500 mg (0.87 mmole) portion of the methylcarbamoyl derivative as obtained in Example 53 was methylated in the same manner as described in Example 52, and converted into a different salt form by passing through a column of 30 ml of IRA-410 (Cl$^-$) to give 327 mg (yield of 60.3%) of the objective compound (colorless crystalline powder).

TLC [silica gel; n-BuOH, AcOH, H$_2$O (4:1:1)] Rf=0.27, single spot.

IR (KBr) cm$^{-1}$: 3350, 2920, 2850, 1730, 1700(sh.), 1695, 1530, 1470, 1255, 1210, 1050.

NMR (60 MC, CDCl$_3$) δ:0.88(3H), 1.25(32H), 2.87(3H), 3.10(2H), 3.45(3H), 3.51(9H), 3.75(1H), 3.87(2H), 4.17(2H), 4.26(2H), 4.37(2H), 5.45(1H), 8.33(1H).

EXAMPLE 55

1-O-[N-(2'-Dimethylaminoethyl)-N-methoxycarbonyl]-carbamoyl-2-O-methyl-3-O-octadecylcarbamoyl-glycerol In 1 ml of chloroform was dissolved 500 mg (0.97 mmole) of the dimethylaminoethyl derivative as obtained in Example 9, and after 0.5 g of methyl chloroformate was added to the solution, 0.5 ml of triethylamine was added dropwise to the mixture under ice-cooling. The reaction solution was concentrated to dryness under reduced pressure, and 20 ml of 5% aqueous sodium hydrogencarbonate solution and 20 ml of ether were added to the residue, followed by stirring thoroughly. The ether layer was separated out, dried over sodium sulfate and concentrated to dryness.

The residue was purified by 10 g of silica gel with chloroform.methanol (19:1) as an eluent to give 350 mg (yield of 62.9%) of the objective compound as a colorless oil.

TLC [silica gel; CHCl$_3$, MeOH (5:1)] Rf=0.75, single spot.

IR (film) cm$^{-1}$: 3350, 2920, 2850, 1790, 1750(sh.), 1725, 1710, 1530, 1470, 1360, 1290, 1250, 1180, 1160, 1110.

NMR (60 MC, CDCl$_3$) δ:0.88(3H), 1.25(32H), 2.25(6H), 2.48(2H), 3.10(2H), 3.45(3H), 3.67(1H), 3.82(3H), 4.20(2H), 4.30(2H), 5.03(1H).

EXAMPLE 56

2-O-Methyl-1-O-[N-methoxycarbonyl-N-(2'-trimethylammonioethyl)]carbamoyl-3-O-octadecylcarbamoylglycerol iodide A 320 mg (0.56 mmole) of the methoxycarbonyl derivative as obtained in Example 55 was treated in the same manner as described in Example 52 to give 327 mg (yield of 81.6%) of the objective compound (colorless powder).

TLC [silica gel; n-BuOH, AcOH, H$_2$O (4:1:1)] Rf=0.27.

IR (KBr) cm$^{-1}$: 3400, 2920, 2850, 1800, 1760, 1710, 1535, 1470, 1480, 1260, 1210, 1150, 1105.

NMR (60 MC, CDCl$_3$) δ:0.88(3H), 1.27(32H), 3.22(2H), 3.45(3H), 3.55(9H), 3.78(1H), 3.90(3H), 4.13(2H), 4.20(2H), 4.38(2H), 4.97(1H).

Elemental analysis, for C$_{31}$H$_{62}$N$_3$O$_7$I.1.5H$_2$O: Calcd.: C, 50.13; H, 8.82; N, 5.66. Found: C, 49.89; H, 8.92; N, 5.87.

EXAMPLE 57

1-O-[N-(2'-Dimethylaminoethyl)-N-phenoxycarbonyl]-carbamoyl-2-O-methyl-O-octadecylcarbamoylglycerol In 5 ml of dichloromethane was dissolved 1.032 mg (2 mmole) of the dimethylaminoethyl derivative as obtained in Example 9, and after 470 mg (3 mmole) of phenyl chloroformate was added to the solution, 633 mg (8 mmole) of pyridine was added dropwise to the mixture under ice-cooling, followed by stirring at room temperature for 4 hours. 15 ml of dichloromethane and 20 ml of water containing 0.5 g of sodium hydrogencarbonate were added to the reaction solution, followed by shaking thoroughly. The dichloromethane layer was separated out, dried over sodium sulfate, and concentrated to dryness under reduced pressure to give the objective compound. Yield of 1.27 g (yield of 100%).

EXAMPLE 58

1-O-[N-(2'-Dimethylaminoethyl)-N-pyrrolidinocarbonyl]carbamoyl-2-O-methyl-O-octadecylcarbamoyl-glycerol A 0.5 ml portion of pyrrolidine was added to 636 mg (1 mmole) of the phenoxycarbonyl derivative as obtained in Example 57, followed by stirring at 70° C. for 5 hours. The reaction solution was concentrated to dryness under reduced pressure, and the residue was purified by silica gel column (10 g), with chloroform.methanol (19:1) used as an eluent to give 613 mg (yield of 100%) of the objective compound (colorless oil).

TLC [silica gel; CHCl$_3$, MeOH (5:1)] Rf=0.75, single spot.

IR (film) cm$^{-1}$: 3350, 2940, 2850, 1730, 1690, 1530, 1470, 1450, 1400, 1360, 1260, 1180, 1160, 1110.

NMR (60 MC, CDCl$_3$) δ:0.92(3H), 1.27(32H), 1.88(4H), 2.22(6H), 2.45(2H), 3.08(2H), 3.42(3H), 3.53(1H), 3.67(6H), 4.17(2H), 4.23(2H), 5.05(1H).

EXAMPLE 59

2-O-Methyl-3-O-octadecylcarbamoyl-1-O-[N-pyrrolidinocarbonyl-N-(2'-trimethylamminoethyl)]carbamoylglycerol iodide In 2 ml of methyl iodide was dissolved 613 mg (1 mmole) of the dimethylamino derivative as obtained in Example 58, and the solution was allowed to stand at room temperature for 24 hours and treated in accordance with the conventional procedure to give 551 mg (yield of 73.0%) of the objective compound (colorless powder).

TLC [silica gel; n-BuOH, AcOH, H$_2$O (4:1:1)] Rf=0.25.

IR (KBr) cm$^{-1}$: 3320, 2930, 2850, 1720, 1680, 1520, 1470, 1440, 1240, 1160.

NMR (60 MC, CDCl$_3$) δ:0.88(3H), 1.27(32H), 1.97(4H), 3.07(2H), 3.43(3H), 3.52(9H), 3.63(1H), 4.10(4H), 4.22(2H), 4.32(2H), 5.06(1H).

Elemental analysis, for C$_{34}$H$_{67}$N$_4$O$_6$I.2H$_2$O: Calcd.: C, 51.64; H, 9.05; N, 7.08. Found: C, 51.49; H, 9.22; N, 7.37.

EXAMPLE 60

1-O-[N-Carbamoyl-N-(2'-trimethylammonioethyl)]carbamoyl-2-O-methyl-3-O-octadecylcarbamoylglycerol iodide In 5 ml of 8.9% ammonia-methanol solution was dissolved 100 mg (0.14 mmole) of the methoxycarbonyl derivative as obtained in Example 56, and the solution was allowed to stand at room temperature for 1 day, and concentrated to dryness under reduced pressure. The residue was recrystallized from 4 ml of ether to give 81 mg (yield of 82.5%) of the objective compound (colorless powder).

TLC [silica gel; n-BuOH, AcOH, H$_2$O (4:1:1)] Rf=0.26.

IR (KBr) cm$^{-1}$: 3300, 2940, 2850, 1800, 1750(sh.), 1710, 1520, 1470, 1260, 1220, 1150, 1100.

NMR (60 MC, CDCl$_3$) δ:0.88(3H), 1.27(32H), 3.08(2H), 3.47(9H), 3.56(3H), 3.67(1H), 3.86(2H), 4.13(2H), 4.27(2H), 4.37(2H), 4.70(1H), 4.97(1H), 6.48(1H).

Elemental analysis, for C$_{30}$H$_{61}$N$_4$O$_6$I.1.5H$_2$O: Calcd.: C, 49.51; H, 8.86; N, 7.70. Found: C, 49.76; H. 8.90; N, 7.59.

EXAMPLE 61

1-O-[N-Dimethylcarbamoyl-N-(2'-dimethylaminoethyl)]carbamoyl-2-O-methyl-3-O-octadecylcarbamoylglycerol In 10 ml of 20% dimethylamine-toluene solution was dissolved 636 mg (1 mmole) of the phenoxy derivative as obtained in Example 57, and the reaction solution was allowed to stand at room temperature for 24 hours and concentrated to dryness under reduced pressure. The residue was purified by 10 g of silica gel, with chloroform.methanol (19:1) used as an eluent to give 440 mg (yield of 75.0%) of the objective compound (colorless oil).

TLC [silica gel; CHCl$_3$, MeOH (5:1)] Rf=0.66, single spot.

IR (film) cm$^{-1}$: 3350, 2930, 2850, 1730, 1690, 1540, 1475, 1420, 1395, 1360, 1290(sh.), 1260, 1170, 1100, 1070.

EXAMPLE 62

1-O-[N-Dimethylcarbamoyl-N-(2'-trimethylammonioethyl)]carbamoyl-2-O-methyl-3-O-octadecylcarbamoylglycerol iodide In 1 ml of chloroform was dissolved 440 mg (0.75 mmole) of the dimethylcarbamoyl derivative as obtained in Example 61, and after 600 mg of methyl iodide was added to the solution, the mixture was allowed to stand at room temperature overnight. The reaction solution was concentrated to dryness under reduced pressure, and the residue was recrystallized from 2 ml of acetone and 8 ml of ether to give 463 mg (yield of 84.7%) of the objective compound (colorless crystalline powder).

TLC [silica gel; n-BuOH, AcOH, H$_2$O (4:1:1)] Rf=0.27.

IR (KBr) cm$^{-1}$: 3400, 2920, 2850, 1710, 1690, 1530, 1470, 1400, 1300, 1260, 1200, 1140.

NMR (60 MC, CDCl$_3$) δ:0.90(3H), 1.25(32H), 3.00(6H), 3.10(2H), 3.43(3H), 3.55(9H), 3.63(1H), 3.93(2H), 3.98(2H), 4.13(2H), 4.30(2H), 4.96(1H).

Elemental analysis, for C$_{32}$H$_{65}$N$_4$O$_6$I.2H$_2$O: Calcd.: C, 50.25; H, 9.09; N, 7.33. Found: C, 50.02; H, 9.14; N, 7.65.

EXAMPLE 63

1-O-[N-(2'-Dimethylaminoethyl)-N-propylcarbamoyl]-carbamoyl-2-O-methyl-3-O-octadecylcarbamoylglycerol.

To 636 mg (1 mmole) of the phenoxy derivative as obtained Example 57 was added 1 ml of propylamine, and the solution was allowed to stand at room temperature for 24 hours and concentrated to dryness under reduced pressure. The residue was purified by 10 g of silica gel, with chloroform.methanol (19:1) used as an eluent to give 586 mg (yield of 100%) of the objective compound (colorless oil).

TLC [silica gel; CHCl$_3$, MeOH (5:1)] Rf=0.75.

IR (film) cm$^{-1}$: 3350, 2940, 2850, 1730, 1630, 1540, 1470, 1410, 1380, 1250, 1195.

EXAMPLE 64

2-O-Methyl-1-O-[N-propylcarbamoyl-N-(2'-trimethylammonioethyl)]carbamoyl-3-O-octadecylcarbamoylglycerol iodide In 2 ml of methyl iodide was dissolved 586 mg (1 mmole) of the propylcarbamoyl derivative as obtained in Example 63, and the solution was allowed to stand at room temperature for 24 hours and concentrated to dryness under reduced pressure. The residue was washed with n-hexane to give 563 mg (yield of 77.2%) of the objective compound (pale yellow solid).

TLC [silica gel, n-BuOH, AcOH, H$_2$O (4:1:1)] Rf=0.25.

IR (KBr) cm$^{-1}$: 3350, 2930, 2850, 1730, 1530, 1470, 1380, 1210, 1150.

NMR (60 MC, CDCl$_3$) δ:0.92(3H), 1.25(32H), 1.57(2H), 3.15(2H), 3.47(3H), 3.50(9H), 3.75(1H), 3.90(2H), 4.17(2H), 4.30(2H), 4.38(2H), 4.67(1H), 5.05(1H).

EXAMPLE 65

1-O-[N-Acetyl-N-(2'-dimethylaminoethyl)]carbamoyl-2-O-benzyl-3-O-octadecylglycerol In 15 ml of pyridine and 7.5 ml of acetic anhydride was dissolved in 1.5 g (2.71 mmole) of the dimethylaminoethyl derivative as obtained in Example 1, and the reaction solution was stirred at room temperature overnight and concentrated to dryness under reduced pressure. The residue was purified by 20 g of silica gel, with chloroform.methanol used as an eluent, to give 1.61 g (yield of 100%) of the objective compound (colorless oil).

TLC [silica gel; CHCl$_3$, MeOH (5:1)] Rf=0.59.

IR (film) cm$^{-1}$: 2930, 2850, 1745, 1705, 1470, 1375, 1245, 1170.

NMR (60 MC, CDCl$_3$) δ:0.92(3H), 1.27(36H), 2.45(6H), 2.47(2H), 2.77(2H), 3.60(2H), 3.83(1H), 3.97(2H), 4.37(2H), 4.65(2H), 7.30(5H).

EXAMPLE 66

1-O-[N-Acetyl-N-(2'-trimethylammonioethyl)]carbamoyl-2-O-benzyl-3-O-octadecylglycerol iodide In 4 ml of methyl iodide was dissolved 1.61 g (2.71 mmole) of the dimethylaminoethyl derivative as obtained in Example 65, and the solution was allowed to stand at room temperature overnight. The reaction solution was concentrated to dryness under reduced pressure, and the residue was recrystallized from 20 ml of ether to give 1.83 g (yield of 92.3%) of the objective compound (colorless crystalline powder).

TLC [silica gel; n-BuOH, AcOH, H$_2$O (4:1:1)] Rf=0.23.

IR (film) cm$^{-1}$: 2930, 2850, 1750, 1690, 1465, 1375, 1350, 1260, 1200, 1160, 1145, 1120, 1095.

NMR (60 MC, CDCl$_3$) δ:0.92(3H), 1.27(32H), 2.50(3H), 3.32(9H), 3.45(2H), 3.53(2H), 3.67(1H), 4.00(2H), 4.13(2H), 4.47(2H), 4.67(2H), 7.33(5H).

Elemental analysis, for C$_{36}$H$_{62}$N$_2$O$_5$I.H$_2$O: Calcd.: C, 57.59; H, 8.99; N, 3.73. Found: C, 57.70; H, 9.19; N, 3.82.

EXAMPLE 67

1-O-[N-Acetyl-N-(2'-trimethylammonioethyl)]carbamoyl-3-O-octadecylglycerol.chloride In 50 ml of 75% methanol was dissolved 1.333 g (1.82 mmole) of the iodide as obtained in Example 66, and the solution was passed through 50 ml of IRA-410(Cl$^-$), followed by washing with a small amount of methanol. The effluent and washing were combined, and concentrated to dryness under reduced pressure. The residue was dissolved in 25 ml of 75% acetic acid, and the solution was stirred overnight in the presence of 300 mg of palladium-carbon under a hydrogen atmosphere. The insoluble material was filtered off, and the filtrate was concentrated to dryness under reduced pressure. The residue was washed with 20 ml of acetone to give 620 mg (yield of 61.8%) of the objective compound (colorless powder).

TLC [n-BuOH, AcOH, H$_2$O; (4:1:1)] Rf=0.28.

IR (film) cm$^{-1}$: 3350, 2910, 2845, 1740, 1690, 1455, 1365, 1255, 1200, 1060.

Elemental analysis, for C$_{29}$H$_{59}$N$_2$O$_5$Cl.H$_2$O: Calcd.: C, 61.19; H, 10.80; N, 4.92. Found: C, 61.05; H, 11.25; N, 5.07.

EXAMPLE 68

1-O-(N-Dimethylaminoethyl)carbamoyl-3-O-octadecylglycerol

In 35 ml of 50% acetic acid was dissolved 3.5 g (6.33 mmole) of the dimethylaminoethyl derivative as obtained in Example 1, and the solution was stirred at room temperature overnight in the presence of 300 mg of palladium carbon under a hydrogen atmosphere. The insoluble material was filtered off, and the filtrate was concentrated to dryness under reduced pressure to give 3.0 g of the objective compound (colorless solid material).

TLC [silica gel; CHCl$_3$, MeOH, H$_2$O (65:25:4)] Rf=0.33.

EXAMPLE 69

1-O-[N-(2'-Dimethylaminoethyl)-N-phenoxycarbonyl]-carbamoyl-3-O-octadecyl-2-O-phenoxycarbonyl-glycerol In 4 ml of dichloromethane were dissolved 1.0 g (2.24 mmole) of the dimethylamino derivative as obtained in Example 68 and 1.4 g (8.95 mmole) of phenyl chlorocarbonate, and 2.8 g (35.2 mmole) of pyridine was added to the solution, followed by stirring at room temperature for 2 hours. 8 ml of dichloromethane and 10 ml of water were added to the reaction solution, and after shaking thoroughly, the organic layer was separated out, dried over sodium sulfate and concentrated to dryness under reduced pressure to give 1.56 g (yield of 100%) of the objective compound (colorless residue).

TLC [silica gel; CHCl$_3$, MeOH (5:1)] Rf=0.68.

IR (film) cm$^{-1}$: 2920, 2850, 1750, 1720, 1460, 1270, 1120.

EXAMPLE 70

2-O-Methoxycarbonyl-1-O-[N-methoxycarbonyl-N-(2'-trimethylammonioethyl)]carbamoyl-3-O-octadecyl-glycerol iodide In 5 ml of methanol and 2 ml of triethylamine was dissolved 0.76 g (1.12 mmole) of the phenoxy derivative as obtained in Example 69, and the solution was allowed to stand at room temperature overnight and concentrated to dryness under reduced pressure. The residue was dissolved in 2 ml of methyl iodide, and the solution was allowed to stand at room temperature for 24 hours and concentrated to dryness under reduced pressure. The resulting residue was purified by 5 g of silica gel, with chloroform.methanol.water (65:25:4), to give 433 mg (yield of 61.8%) of the objective compound (colorless solid).

TLC [silica gel; n-BuOH, AcOH, H$_2$O (4:1:1)] Rf=0.21.

IR (film) cm$^{-1}$: 3350, 2930, 2850, 1650(sh), 1720, 1280, 1260.

NMR (60 MC, CDCl$_3$) δ:0.92(3H), 1.27(32H), 3.43(9H), 3.78(6H), 5.0(1H), miscellaneous 3.3–4.6.

EXAMPLE 71

2-O-Dimethylcarbamoyl-1-O-[N-dimethylcarbamoyl-N-(2'-trimethylammonioethyl)]carbamoyl-3-O-octadecylglycerol chloride In 10 ml of 20% dimethylamine.toluene solution was dissolved 0.76 g (1.12 mmole) of the phenoxy derivative as obtained in Example 69, and the solution was allowed to stand at room temperature overnight and concentrated to dryness under reduced pressure. The residue was dissolved in 2 ml of methyl iodide, and the solution was allowed to stand at room temperature for 24 hours, and concentrated again to dryness under reduced pressure. The resulting residue was dissolved in 20 ml of 75% methanol, and the solution was passed through 15 ml of IRA-410(Cl$^-$), followed by washing with a small amount of 75% methanol. The effluent and washing were combined and concentrated to dryness under reduced pressure. The residue was recrystallized from 2.5 ml of acetone and 2.5 ml of ether to give 259 mg (yield of 35.5%) of the objective compound (colorless powder).

TLC [n-BuOH, AcOH, H$_2$O (4:1:1)] Rf=0.21.

IR (film) cm$^{-1}$: 3400, 2920, 2850, 1700, 1525, 1480, 1400, 1260, 1215, 1195, 1120.

EXAMPLE 72

1-Octadecyloxy-2-phthalimido-3-(2'-pyridinioethyl)-carbamoyloxypropane chloride (i) 3-O-Octadecyl-2-O-tosyl-1-O-tritylglycerol In 9 ml of pyridine was dissolved 5.0 g (8.52 mmole) of 3-O-octadecyl-1-O-tritylglycerol, and after 1.95 g (10.22 mmole) of tosyl chloride was added to the solution, the mixture was stirred at room temperature overnight and concentrated to dryness under reduced pressure. The residue was dissolved in 50 ml of water and 50 ml of dichloromethane, and after shaking thoroughly, the dichloromethane layer was separated out. The organic layer was concentrated to dryness under reduced pressure, and the residue was purified by silica gel column (50 g), with n-hexane.ethyl acetate (193:7) used as an eluent, to give 5.3 g (yield of 83.9%) of colorless needles.

m.p. 52°–53° C.

(ii) 3-Octadecyloxy-2-phthalimido-1-trityloxypropane

In 53 ml of dimethylsulfoxide was dissolved 5.3 g (7.15 mmole) of the tosyl derivative as obtained in Example 72-(i), and 10.6 g of potassium phthalimide was added to the solution, followed by stirring at the temperature of the bath of 115° C. for 3.5 hours. The reaction solution was poured into 500 ml of water, followed by extraction with 500 ml of ether, and the ether layer separated was dried over sodium sulfate, and concentrated to dryness under reduced pressure. The residue was purified by silica gel column (50 g), with n-hexane.ethyl acetate (193:7) used as an eluent, to give 3.0 g (yield of 58.6%) of a colorless oil.

TLC [silica gel; n-hexane, EtOAc (9:1)] Rf=0.25, single spot.

(iii) 1-Hydroxy-3-ocatadecyloxy-2-phthalimidopropane

In 50 ml of 70% acetic acid was dissolved 3.0 g (4.19 mmole) of the trityl derivative as obtained in Example 72-(ii), followed by heating under reflux for 1 hour. The reaction solution was concentrated to dryness under reduced pressure, and the residue was purified by silica gel column (40 g), with n-hexane, ethyl acetate (4:1) as an eluent, to give 1.17 g (yield of 58.9%) of colorless needles, m.p. 60°–61° C.

TLC [silica gel; n-hexane, EtOAc (4:1)] Rf=0.16.

IR (KBr) cm$^{-1}$: 3500, 3450, 2910, 2850, 1765, 1700, 1465, 1390, 1150, 1060, 875.

(iv) 1-Octadecyloxy-2-phthalimido-3-(2'-chloroethylcarbamoyloxy)propane

In 6 ml of dichloromethane was dissolved 1.057 g of 3-octadecyloxy-2-phtalimido-1-propanol, and 283 mg of β-chloroethyl isocyanate and 300 mg of triethylamine were added to the solution, followed by stirring at room temperature for 14 hours. The reaction solution was concentrated to dryness under reduced pressure, and the residue was purified by silica gel chromatography (eluent; n-hexane-ethyl acetate=3:1) to give 1.30 g of the objective compound as a colorless solid.

NMR (90 MHZ, CDCl$_3$): 0.87(3H,t), 1.16, 1.25(32H,m), 3.3–3.65(6H,m), 4.85(2H,m), 4.4–4.9(3H,m), 5.11(1H,br.), 7.6–7.95(4H,m).

(v) 1-Octadecyloxy-2-phthalimido-3-(2'-pyridinioethyl)carbamoyloxypropane chloride In 1 ml of pyridine was dissolved 200 mg of the chloride as obtained in Example 72-(iv), followed by heating under reflux for 6 hours. The reaction solution was concentrated to dryness, and the residue was purified by silica gel chromatography (eluent; chloroform-methanol-water, 65:25:2) to give 150 mg of the objective compound. Pale brown solid.

IR (KBr, cm$^{-1}$); 2925, 2850, 1778, 1715, 1635, 1490, 1470, 1390, 1260, 1120, 730.

NMR (90 MHz, CDCl$_3$) δ:0.87(3H,t), 1.16, 1.25(32H,m), 3.0–3.55(2H,m), 3.55–4.0(4H,m), 4.27(2H,d), 4.53(1H,m), 5.03(2H,m, CH$_2$N$^+$, 7.12(1H,br,NH), 7.6–7.9(4H,m), 8.05(2H,m), 8.45(1H,m), 9.31(2H,d).

TLC Rf=0.6 (CHCl$_3$—MeOH—H$_2$O, 65:25:4).

EXAMPLE 73

1-Octadecyloxy-2-phthalimido-3-(2'-thiazolioethyl)carbamoyloxypropane chloride

In 1 ml of thiazole was dissolved 200 mg of the chloride as obtained in Example 72-(iv), followed by heating at 100° C. for 48 hours.

The reaction solution was post-treated and purified in the same manner as described in Example 72 to give 70 mg of the objective compound. Pale brown solid.

IR (KBr, cm$^{-1}$): 3400, 3050, 2925, 2855, 1780, 1715, 1530, 1475, 1390, 1260, 1125, 1040, 880.

NMR (90 MHz, CDCl$_3$): 0.87(3H,t), 1.16, 1.25(32H,m), 3.4(2H,m), 3.5–4.0(4H,m), 4.33(2H,d), 4.55(1H,m), 4.86(2H,m,CH$_2$N$^+$), 7.04(1H,br,NH), 7.6–7.95(4H,m), 8.18(1H), 8.50(1H), 10.70(1H).

TLC Rf=0.5 (CHCl$_3$—MeOH—H$_2$O=65:25:4).

EXAMPLE 74

1-Octadecyloxy-2-phthalimido-3-[N-2'-(N-methylpyrrolidinio)ethyl]carbamoyloxy]propane chloride In 1 ml of N-methylpyrrolidine was dissolved 300 mg of the chloride as obtained in Example 72-(iv), followed by heating under reflux for 8 hours. The reaction solution was purified in the same manner as described in Example 73 to give 144 mg of the objective compound. Pale brown solid.

IR (KBr, cm$^{-1}$): 3420, 2925, 2850, 1780, 1718, 1530, 1475, 1390, 1265, 1125, 1040, 880, 730.

NMR (90 MHz, CDCl$_3$): 0.87(3H,t), 1.16, 1.25(32H,m), 2.22(4H,m), 3.27(3H,s,NMe), 3.5–4.0(10H,m), 4.43(2H,d), 4.67(1H,m), 7.6–7.9(4H,m).

TLC Rf=0.6 (CHCl$_3$—MeOH—H$_2$O; 65:25:4).

EXAMPLE 75

1-Octadecyloxy-2-phthalimido-3-[(2'-N,N-dimethylaminoethyl)carbamoyloxy]propane

In 3 ml of chloroform was dissolved 287 mg of 1-octadecyloxy-2-amino-3-(2'-N,N-dimethylaminoethyl)-carbamoyloxypropane as obtained in Example 20-(ii), and 151.3 mg of carboethoxyphthalimide and 69 mg of triethylamine were added to the solution, followed by stirring at room temperature for 2 days. The reaction solution was concentrated to dryness, and the residue was purified by silica gel chromatography (eluent: n-hexane-ethyl acetate; 10:1) to give 292 mg of a colorless solid.

IR (film, cm$^{-1}$): 3360, 2920, 2850, 1775, 1710, 1520, 1470, 1382, 1250, 1120, 1035, 875.

NMR (90 MHz, CDCl$_3$) δ:0.87(3H,t), 1.17, 1.25(32H,m), 2.15(6H,s), 2.31(2H,t), 3.17(2H,m), 3.40(2H,m), 3.84(2H,m), 4.4–4.9(3H,m), 5.15(1H,br,NH), 7.6–8.0(4H,m).

EXAMPLE 76

1-Octadecyloxy-2-phthalimido-3-[N-acetyl-N-(2'-N,N-dimethylaminoethyl)carbamoyloxy]propane In 3 ml of chloroform was dissolved 212 mg of the compound as obtained in Example 75, and 1 ml of triethylamine and 0.3 m.l of acetic anhydride were added to the solution, followed by stirring overnight. The reaction solution was concentrated to dryness, and the residue was purified by silica gel chromatography (eluent; chloroform-methanol: 20:1) to give 153 mg of a colorless solid.

IR (film, cm$^{-1}$): 2925, 2850, 1775, 1740, 1712, 1470, 1385, 1245, 1180, 980, 880.

NMR (90 MHz, CDCl$_3$): 0.87(3H,t), 1.20, 1.25(32H,m), 2.15(6H,s), 2.33(2H,t), 2.39(3H,s), 3.44(2H,t), 3.69–3.98(4H,m), 4.4–4.9(3H,m), 7.6–8.0(4H,m).

TLC Rf=0.6(CHCl$_3$—MeOH, 10:1).

EXAMPLE 77

1-Octadecyloxy-2-phthalimido-3-[N-acetyl-N-(2'-trimethylammonioethyl)carbamoyloxy]propane iodide In 5 ml of ether was dissolved 150 mg of the dimethylamino derivative as obtained in Example 76, and 100 mg of methyl iodide was added to the solution, followed by stirring at room temperature overnight. The reaction solution was concentrated to dryness, and the residue was purified by silica gel chromatography (eluent; chloroform-methanol, 5:1), followed by reprecipitation from ether to give 115 mg of the objective compound. Pale yellow solid.

IR (KBr, cm$^{-1}$): 2925, 2850, 1778, 1750, 1715, 1470, 1390, 1265, 1205, 1160, 1120, 1095, 1040, 880, 778, 730.

NMR (90 MHz, CDCl$_3$) δ:0.87(3H, t), 1.16, 1.25(32H,m), 2.38 (3H,s), 3.52(9H,s), 3.3–3.8(4H,m), 3.93(2H,d), 4.15(2H,m), 4.5–4.95(3H,m), 7.65–7.95(4H,m).

EXAMPLE 78

3-Octadecyloxy-2-(1-pyrrolidyl)-1-propanol

In 4 ml of pyrrolidine was dissolved 1.89 g of 3-octadecyl-2-tosyl-1-tritylglycerol, followed by heating under reflux for 4 hours. The reaction solution was concentrated to dryness, and from the residue, the substance soluble in h-hexane was purififed by silica gel chromatography (eluent n-hexane-ethyl acetate-aqueous ammonia, 15:5:1, supernatant layer) to give 1.60 g of the 2-pyrrolidyl derivative in the form of a colorless oil.

The compound was dissolved in 60% acetic acid, and the solution was heated at 100° C. for 1.5 hours and concentrated to dryness. The residue was dissolved in chloroform, and the solution was washed with aqueous sodium hydrogencarbonate solution, dried and concentrated, followed by purification by silica gel chromatography (eluent, chloroform-methanol, 20:1) to give 789 mg of the objective compound in the form of a pale brown solid.

IR (KBr, cm$^{-1}$): 3210, 2925, 2850, 1490, 1475, 1420, 1382, 1328, 1135.

EXAMPLE 79

1-Octadecyloxy-2-(1-pyrrolidyl)-3-(2'-dimethylaminoethylcarbamoyloxy)propane

In 5 ml of dichloromethane was dissolved 397 mg of 1-octadecyloxy-2-pyrrolidyl-1-propanol, and 158 mg of pyridine and 156 mg of phenyl chloroformate were added to the solution under ice-cooling, followed by stirring at room temperature for 1 hour. 20 ml of chloroform and 10 ml of water were added to the reaction solution, followed by separation. The organic layer was washed with aqueous sodium hydrogencarbonate solution, dried, and concentrated to give the formate derivative. 1.5 ml of asym-dimethylethylenediamine was added to the compound, followed by heating at 70° C. for 4 hours. The reaction solution was subjected to silica gel chromatography (eluent chloroform-methanol-water, 65:25:4) to give 200 mg of the objective compound in the form of a pale brown solid.

IR (KBr, cm$^{-1}$): 3340, 2920, 2850, 2798, 1692, 1542, 1470, 1385, 1280, 1130.

NMR (90MHz, CDCl$_3$): 0.87(3H, t), 1.25(32H, m), 1.77(4H, m), 2.20(6H, s), 2.37(2H, t), 2.70(5H, m), 3.20(2H, t), 3.40(2H, t), 3.55(2H, d), 4.25(2H, m), 5.28(1H, br, NH).

TLC Rf=0.33 (CHCl$_3$—MeOH—H$_2$O, 65:25:4).

EXAMPLE 80

2-Methoxy-3-octadecylcarbamoyloxypropylamine

A 3.48 g (20 mmole) portion of diethyl diazocarboxylate was added dropwise to a solution of 4 g (10 mmol) of 2-methoxy-3-octadecylcarbamoyloxy-1-propanol, 2.94 g (20 mmole) of phthalimide and 5.24 g (20 mmole) of triphenylphosphine in 100 ml of anhydrous tetrahydrofuran, followed by further stirring at room temperature for 40 hours. The reaction solution was concentrated to dryness under reduced pressure, and the residue was subjected to separation and purification by chromatography on a column of 100 g of silica gel. From the eluate of n-hexane-ethyl acetate (4:1), there was obtained 5.7 g of the crude phthalimide derivative. 100 ml of methanol and 0.5 ml of hydrazine hydrate were added to the compound, followed by heating under reflux for 2 hours. The reaction solution was concentrated to dryness under reduced pressure, and chloroform was added to the residue. The insoluble matter was filtered off, and the filtrate was concentrated to dryness under reduced pressure. The residue was subjected to separation and purification by chromatography on a column of 80 g of silica gel. From the eluate of chloroform-methanol-triethylamine (95:5:0.125), there was obtained the objective compound in the form of a colorless powder. Yield of 2.7 g (68%).

IR (KBr) cm$^{-1}$: 3350(NH$_2$), 2915(CH), 1690(C=O), 1520(CONH), 1469(CH$_2$), 1273.

NMR δ (CDCl$_3$): 0.87(3H), 1.23(32H), 2.7–2.95(2H,CH$_2$NE$_2$), 3.03–3.4(3H,CH+CONHCH$_2$), 3.43(3H, s,OCH$_3$), 4.14(2H,d,J=4.8 Hz, CH$_2$O), 4.7–4.95(CONH).

EXAMPLE 81

2-Dimethylaminoethyl [(3-octadecylcarbamoyloxy-2-methoxy)propyl]carbamate

A 391 mg (2.5 mmole) portion of phenyl chloroformate was added dropwise to a solution of 223 mg (2.5 mmole) of N,N-dimethylethanolamine and 253 mg (2.5 mmole) of triethylamine in 5 ml of methylene chloride under ice-cooling with stirring, followed by stirring further under ice-cooling for 10 minutes and then at room temperature for 30 minutes. The reaction solution was diluted with methylene chloride, and the solution was washed with 1% aqueous sodium hydrogencarbonate solution and dried over sodium sulfate. The solvent was distilled off, and there was obtained 465 mg of the crude 2-dimethylaminoethyl phenyl carbonate in the form of a colorless oil. 880 mg (2.2 mmole) of the compound as obtained in Example 80 was added to the compound, followed by warming at 90° C. for 2 hours. The reaction solution was subjected to separation and purification by chromatography on a column of silica gel (40 g). After impurities were removed with n-hexane-ethyl acetate (1:4) as an eluent, there was obtained the objective compound in the form of a colorless powder from the eluate of chloroform-methanol (10:1). Yield of 800 mg (71%).

IR (KBr) cm$^{-1}$: 3300(NH), 2920(CH), 2850(CH), 1695(CO), 1532 (CONH), 1472(CH$_2$), 1277(CONH), 1155.

NMR (CDCl$_3$) δ:0.87(3H), 1.25(32H), 2.26(6H,s,NMe$_2$), 2.53 (2H,t,J=5.9 Hz, CH$_2$N), 3.03–3.5(5H), 3.40(3H,s,OCH$_3$), 4.12 (2H,d,J=4.5 Hz,CHCH$_2$O), 4.16(2H,t,J=5.9 Hz,OCH$_2$CH$_2$N), 4.8(1H, CONH), 5.18(1H,CONH).

EXAMPLE 82

2-Trimethylammonioethyl N-[2-(methoxy-3-octadecyloxy)propyl]carbamate iodide

To a solution of 258 mg (0.5 mmole) of the compound as obtained in Example 81 in 5 ml of ether was added 355 mg (2.5 mmole) of methyl iodide, and the mixture was allowed to stand at room temperature overnight. The substance which separated out was collected by filtration to give the objective compound in the form of colorless crystals. Yield of 305 mg (93%).

IR (KBr) cm$^{-1}$: 3325(NH), 2920(CH), 2850(CH), 1728(CO), 1708 (CO), 1530(CONH), 1469(CH$_2$), 1257(CONH).

NMR δ (CDCl$_3$): 0.87(3H), 1.26(32H), 3.02–3.45(5H), 3.43(3H,s, OCH$_3$), 3.53(9H,s,N$^+$Me$_3$), 3.95–4.20(4-

H,OCH$_2$+CH$_2$N+), 4.50-4.70 (2H,CH$_2$CH$_2$N+) , 5.07(1H,NH), 6.15(1H,NH).

EXAMPLE 83

2-Dimethylaminoethyl N-acetyl-N-[(2-methoxy-3-octadecylcarbamoyloxy)-propyl]carbamate In 1 ml of anhydrous tetrahydrofuran was dissolved 145 mg (0.28 mmole) of the compound as obtained in Example 81, and 0.18 ml (1.55N, 0.28 mmole) of n-butyl lithium was added to the solution under ice-cooling with stirring. The solution was poured into acetic anhydride all at once, and the reaction solution was diluted with chloroform, washed with 1% aqueous sodium hydrogencarbonate solution and dried over sodium sulfate. The solvent was distilled off, and the resulting residue was subjected to separation and purification by chromatography on a column of 5 g of silica gel. From the eluate of ethyl acetate-acetone (15:1), there was obtained the objective compound in the form of a colorless powder. Yield of 25 mg (16%).

IR (KBr) cm$^{-1}$: 3330(NH), 2915(CH), 2845(CH), 1735sh(CO), 1720(CO), 1525(CONH), 1465(CH$_2$), 1373, 1247, 1189, 1152.

NMR δ (CDCl$_3$): 0.87(3H), 1.25(32H), 2.27(6H,s,NMe$_2$), 2.48(3H,s,COCH$_3$), 2.61(2H,t,J=6.0 Hz, CH$_2$N), 3.03-3.30(2H, NHCH$_2$), 3.38(3H,s,OCH$_3$), 3.5-2.7(1H,CH), 3.84-3.96(2H,m,CH$_2$N), 4.03-4.17(2H,m,CH$_2$O), 4.29(2H,t,J=6.0 Hz,OCH$_2$CH$_2$N), 4.78(1H,NH).

EXAMPLE 84

2-Trimethylammonioethyl N-acetyl-N-[(2-methoxy-3-octadecylcarbamoyloxy)-propyl]carbamate iodide In 0.5 ml of ether was dissolved 25 mg (0.045 mmole) of the compound as obtained in Example 83, and 32 mg (0.225 mmole) of methyl iodide was added to the solution. The mixture was allowed to stand at room temperature overnight, and the substance which separated out was collected by filtration to give the objective compound in the form of colorless crystals. Yield of 25 mg (80%).

IR (KBr) cm$^{-1}$: 2910(CH), 2845(CH), 1707(CO) 1528(CONH), 1466(CH$_2$), 1255, 1190, 1150.

NMR δ (CDCl$_3$): 0.87(3H), 1.25(32H), 2.51(3H,s,COCH$_3$), 3.03-3.25(2H,NHCH$_2$), 3.32(3H,s,OCH$_3$), 3.55(9H,s,N+Me$_3$), 3.5-3.7 (1H,CH), 3.85-4.5(6H), 4.6-4.8(2H,OCH$_2$CH$_2$N+), 5.47(1H,NH).

EXAMPLE 85

3-[2-(2-Tetrahydropyranyloxy)ethyl]hydantoin

In ethanol (40 ml) was dissolved 1.24 g (0.02 mole) of potassium hydroxide, and 2 g (0.02 mole) of hydantoin was added to the solution, followed by stirring at room temperature for 30 minutes. 4.6 g (0.022 mole) of 2-(2-tetrahydropyranyloxy)ethyl bromide was added, followed by heating under reflux for 66 hours. After cooling, the reaction solution was filtered, and the filtrate was concentrated to dryness under reduced pressure. The residue was treated with water, followed by extraction with chloroform, and the extract was dried over potassium carbonate and the solvent was distilled off under reduced pressure. n-Hexane was added to the resulting residue, and the mixture was filtered to give the objective compound in the form of colorless crystals. Yield of 1.7 g (37%).

IR (KBr) cm$^{-1}$: 3300(NH), 2955(CH), 2925(CH), 2860(CH), 1765(CO), 1720(CO), 1705(CO), 1450(CH$_2$), 1075

NMR δ (CDCl$_3$): 1.60(6H), 3.5-3.856H), 3.95(2H,s,NHCH$_2$), 4.61(1H,CH), 6.57(1H,NH).

EXAMPLE 86

1-(2-Benzyloxy-3-octadecyloxy)propyl tosylate

In 24 ml of triethylamine were dissolved 1.3 g (3 mmole) of 1-(2-benzyloxy-3-octadecyloxy)propanol and 1.7 g (9 mmole) of tosyl chloride, and the solution was warmed at 65° C. and stirred for 1.5 days. The reaction solution was concentrated to dryness under reduced pressure, and the residue was dissolved in chloroform. The solution was washed with water, dried over potassium carbonate. The solvent was distilled off under resuced pressure, and the residue was subjected to separation and purification by chromatography on a column of 40 g of silica gel. From the eluate of n-hexane-ethyl acetate (4:1), there was obtained the objective compound in the form of a colorless oil. Yield of 1.4 g (83%).

IR (liq) cm$^{-1}$: 2920(CH), 2850(CH), 1465(CH$_2$), 1367(SO$_2$), 1173(SO$_2$).

NMR δ (CDCl$_3$): 0.87(3H), 1.25(32H), 2.42(3H,s,CH$_3$), 3.33 (2H,t,J=6.0 Hz,OCH$_2$CH$_2$), 3.42(2H,d,J=5.5 Hz,CHCH$_2$O), 3.73(1H,CH), 3.96-4.29(2H,CH$_2$OSO$_2$), — 4.57(2H,CH$_2$Ph), 7.23-7.33(7H,phenyl ring-H), 7.77(2H,phenyl ring-H).

EXAMPLE 87

1-[1-(2-Benzyloxy-3-octadecyloxy)propyl]-3-(2-hydroxyethyl)hydantoin

A 740 mg (13.2 mmole) portion of potassium hydroxide was added to a solution of 753 mg (3.3 mmole) of the compound as obtained in Example 85 and 650 mg (1.1 mmole) of the compound as obtained in Example 86 in 5 ml of dimethylsulfoxide, and the mixture was stirred vigorously at room temperature for 2 days. The reaction solution was poured into ice-cold water, and the mixture was made acid with aqueous hydrochloric acid, followed by extraction with ethyl acetate. The extract was dried over sodium sulfate and the solvent was distilled off under reduced pressure. 25 ml of ethanol and 1 ml of aqueous hydrochloric acid were added to the residue, and the mixture was warmed at 80° C. and stirred for 0.5 hour. The reaction solution was concentrated under reduced pressure, and the residue was dissolved in chlorform. The solution was washed with water, dried over potassium carbonate and the solvent was distilled off under reduced pressure. The residue was subjected to separation and purification by chromatography on a column of 20 g of silica gel. From the eluate of n-hexane-ethyl acetate, there was was obtained the objective compound in the form of a pale yellow oil. Yield of 190 mg (31%).

NMR δ (CDCl$_3$): 0.87(3H), 1.26(32H), 2.78(1H,t,J=5.5 Hz,OH), 3.35-3.53(6H,CHCH$_2$OCH$_2$+NCH$_2$), 3.63-3.83-(5H,NCH$_2$+CH$_2$OH+CH), 3.88(2H,ABq,

4.47 and 4.73(2H, two sets of doublet, J=12.0 Hz,CH₂Ph), 7.29(5H,s,phenyl ring-H).

EXAMPLE 88

1-[1-(2-Benzyloxy-3-octadecyloxy)propyl]-3-(2-tosyloxyethyl)hydantoin

A solution of 187 mg (0.33 mmole) of the compound as obtained in Example 87 and 70 mg (0.37 mmole) of tosyl chloride in 2.6 ml of triethylamine was allowed to stand at room temperature overnight, further warmed at 50°–55° C. and stirred for 4 hours. The reaction solution was concentrated to dryness under reduced pressure, and the residue was subjected to separation and purification by chromatography on a column of 5 g of silica gel. From the eluate of n-hexane-ethyl acetate (4:1), there was obtained the objective compound in the form of a pale yellow oil. Yield of 200 mg (84%).

IR (liq) cm⁻¹: 2925(CH), 2850(CH), 1772(CO), 1720(CO), 1467 (CH₂), 1370(SO₂), 1178(SO₂), 760.

NMR δ (CDCl₃): 0.87(3H), 1.25(32H), 2.41(3H,s,CH₃), 3.35–3.53 (6H,CH₂OCH₂+NCH₂), 3.64–3.76(3H,NCH₂+CH), 3.83(2H,ABq,

NCH₂C), 4.22(2H,t,J=5.7 Hz,CH₂OTs), 4.48 and 4.71(2H,two sets of doublet, J=12.0 Hz,CH₂Ph), 7.25–7.33(7H,phenyl ring-H), 7.76 (2H,d,phenyl ring-H).

EXAMPLE 89

1-[1-(2-Hydroxy-3-octadecyloxy)propyl]-3-(2-tosyloxyethyl)hydantoin

A 8 ml portion of acetic acid was added to 200 mg (0.28 mmole) of the compound as obtained in Example 88 and 150 mg of 10% Pd-C (50% wet), and the mixture was stirred at room temperature overnight under a hydrogen atmosphere. The catalyst was filtered off, and the filtrate was concentrated to dryness under reduced pressure. The residue was subjected to separation and purification by chromatography on a column of 10 g of silica gel. From the eluate of n-hexane-ethyl acetate (1:1), there was obtained the objective compound in the form of a colorless solid. Yield of 100 mg (57%).

IR (film) m⁻¹: 2925(CH), 2850(CH), 1772(CO), 1713(CO), 1470 (CH₂), 1370(SO₂), 1178(SO₂), 760.

NMR δ (CDCl₃): 0.87(3H), 1.25(32H), 2.43(3H,s,CH₃), 2.80 (1H,d,J=4.0 Hz,OH), 3.35–3.53(6H,CH₂OCH₂+NCH₂), 3.76(2H,t,J=5.5 Hz, NCH₂), 3.9–4.1(1H,CH), 4.02(2H,s,

NCH₂C), 4.25(2H,t,J=5.5 Hz, CH₂OTs), 7.31(2H,d,phenyl ring-H), 7.76(2H,d,phenyl ring-H).

EXAMPLE 90

1-[1-(2-Acetoxy-3-octadecyloxy)propyl]-3-(2-tosyloxyethyl)hydantoin

To 75 mg (0.12 mmole) of the compound as obtained in Example 89 were added 0.5 ml of pyridine and 0.5 ml of acetic anhydride, and the mixture was allowed to stand at room temperature overnight. The reaction solution was concentrated to dryness under reduced pressure, and the residue was subjected to separation and purification by chromatography on a column of 5 g of silica gel. From the eluate of n-hexane-ethyl acetate (2:1), there was obtained the objective compound in the form of colorless crystals. Yield of 55 mg (69%).

IR (KBr) cm⁻¹: 2920(CH), 2850(CH), 1760(CO), 1738(OAc), 1712(CO), 1478(CH₂), 1360(SO₂), 1230(OAc), 1172(SO₂).

NMR δ (CDCl₃): 0.87(3H), 1.25(32H), 2.05(3H,s,COCH₃), 2.43 (3H,s,CH₃), 3.35–3.67(6H,CH₂OCH₂+NCH₂), 3.75(2H,t,J=5.5 Hz, NCH₂), 3.92(2H,ABq,

NCH₂C), 4.23(2H,t,J=5.5 Hz,CH₂OTs), 5.11(1H,CH), 7.31(2H,d,phenyl ring-H), 7.76(2H,d,phenyl ring-H).

EXAMPLE 91

1-[1-(2-Acetoxy-3-octadecyloxy)propyl]-3-(2-trimethylammonioethyl)hydantoin chloride In 10 ml of 20% trimethylamine-toluene solution was dissolved 100 mg (0.15 mmole) of the compound as obtained in Example 90, and the solution was allowed to stand at room temperature for 3.5 days, then warmed in a sealed tube at 60° C. and allowed to stand for 12 hours. The reaction solution was concentrated to dryness under reduced pressure, and the residue was dissolved in methanol-water (8:2), followed by passing through a column of Dowex 21K (Cl type), a strongly basic ion exchange resin. The eluate containing the objective compound was concentrated to dryness, and the residue was subjected to separation and purification by chromatography on a column of 2 g of silica gel. From the eluate of chloroform-methanol-water (65:25:4), there was obtained the objective compound in the form of a colorless powder. Yield of 75 mg (85%).

IR (KBr) cm⁻¹: 2920(CH), 2850(CH), 1767(CO), 1735(OAc), 1709(CO), 1470(CH₂), 1235(OAc).

NMR δ (CDCl₃): 0.87(3H), 1.25(32H), 2.06(3H,s,COCH₃), 3.35–3.67(6H,CH₂OCH₂+NCH₂), 3.43(9H,s,N+Me₃), 3.96—4.06(6H,NCH₂CH₂N+

+NCH₂C), 5.02–5.20(1H,CH).

EXAMPLE 92

1-[1-(2-Acetoxy-3-octadecyloxy)propyl]-3-(2-thiazolioethyl)hydantoin chloride

To 400 mg (0.6 mmole) of the compound as obtained in Example 90 was added 5 ml of thiazole, and the mixture was heated at 95° C. and stirred for 15 hours. The reaction solution was concentrated to dryness under reduced pressure, and the residue was dissolved in methanol-water (8:2), followed by passing through a column of Dowex 21K (Cl type), a strongly basic ion exchange resin. The eluate containing the objective compound was concentrated to dryness, and the residue was subjected to separation and purification by chromatography on a column of 5 g of silica gel. From the eluate of chloroform-methanol-water (65:25:4), there was obtained the objective compound in the form of a colorless powder. Yiled of 270 mg (73%).

IR (KBr) cm⁻¹: 2920(CH), 2850(CH), 1767(CO), 1737(OAc), 1703(CO), 1470(CH₂), 1236(OAc).

NMR δ (CDCl₃): 0.87(3H), 1.25(32H), 2.07(3H,s,COCH₃), 3.34–3.63(6H,CH₂OCH₂+NCH₂), 4.08(4H,

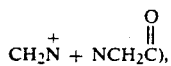

4.95–5.23(3H, NCH₂CH₂N⁺+CH), 8.16(1H,thiazole ring-H), 8.75(1H,thiazole ring-H), 11.23(1H, thiazole ring-H).

EXAMPLE 93

2-O-Benzyl-3-O-octadecyl-1-O-tosylglycerol

In 5 ml of pyridine were dissolved 1 g (2.3 mmole) of 2-O-benzyl-3-O-octadecylglycerol and 1.144 g (6.0 mmole) of tosyl chloride, and the solution was stirred at room temperature overnight. The reaction solution was concentrated to dryness under reduced pressure, and 20 ml of 10% aqueous hydrogencarbonate solution and 20 ml of ether were added to the residue, followed by shaking thoroughly. The ether layer was separated, dried over sodium sulfate and concentrated to dryness under reduced pressure. The residue was purified by 15 g of silica gel, with n-hexane-ethyl acetate (9:1) used as an eluent, to give 1.2 g (yield of 88.6%) of a colorless solid.

IR (film) cm⁻¹: 2920, 2850, 1460, 1365, 1190, 1180, 1120, 1100, 990, 820.

NMR (60 MC, CDCl₃) δ:0.85(3H), 1.28(32H), 2.43(3H), 3.37(4H), 3.77(1H), 4.15(2H), 4.57(2H), 7.2(2H), 7.27(5H), 7.77(2H).

EXAMPLE 94

1-(2-Benzyloxy-3-octadecyloxy)propylurasil

In a mixture of 20 ml of dimethylformamide and 5 ml of dimethylsulfoxide were dissolved 0.91 g (8.16 mmole) of urasil, 1.2 g (2.04 mmole) of the tosylate as obtained in Example 93 and 865 mg (8.16 mmole) of sodium carbonate, and the solution was stirred at 50° C. for 5 hours. The reaction solution was concentrated to dryness under reduced pressure, 5 ml of water was added to the resulting residue, and the mixture was adjusted to pH 7.0 with conc. hydrochloric acid, and concentrated again to dryness under reduced pressure. The residue was treated with 15 ml of chloroform and 10 ml of methanol to carry out extraction, and after the insoluble material was filtered off, the filtrate was again concentrated to dryness. The residue was purified by 10 g of silica gel with chloroform-methanol (49:1) used as an eluent to give 710 mg (yield of 65.8%) of a colorless powder.

TLC [silica gel; CHCl₃—MeOH (19:1)] Rf=0.46.

IR (film) cm⁻¹: 2930, 2850, 1690, 1460, 1380, 1360, 1240, 1120, 1060.

UV spectrum, λ_{max}(90% MeOH); 266 mμ, λ_{min}(90% MeOH) 233 mμ. λ_{max}(pH 6.0, 90% MeOH) 264.5 mμ. λ_{min}(pH 1.0, 90% MeOH) 242 mμ.

EXAMPLE 95

1-(2-Benzyloxy-3-octadecyloxy)propyl-3-(2-tetrahydropyranyloxy)ethylurasil

A mixture of 710 mg (1.34 mmole) of the 1-substituted uracil as obtained in Example 94, 842 mg (4.08 mmole) of 2-pyranyloxyethyl bromide and 300 mg (5.36 mmole) of potassium hydroxide in 3 ml of dimethylsulfoxide was stirred vigorously at 50° C. for 2 hours. The reaction solution was poured into 20 ml of ice-water, and 20 ml of ether was added to the resulting mixture, followed by shaking vigorously. The ether layer was separated and concentrated to dryness under reduced pressure. The residue was purified by 10 g of silica gel with n-hexane-ethyl acetate (19:1) to give 570 mg (yield of 64.7%) of a colorless solid.

TLC [silica gel; CHCl₃—MeOH (19:1)] Rf=0.80.

IR (film) cm⁻¹: 2910, 2850, 1700, 1660, 1445, 1380, 1355, 1115, 1070, 1030, 750.

NMR (60 MC, CDCl₃): 0.87(3H), 1.26(32H), 1.60(6H), 3.2–4.1 (12H), 4.22(1H), 4.53(2H), 4.67(1H), 5.57(1H), 7.13(1H), 7.20(5H).

UV spectrum, λ_{max}(MeOH) 267 mμ λ_{min}(MeOH) 240 mμ. λ_{max}(0.05N-NaOH in MeOH) 267 mμ. λ_{max}(0.05N-NaOH in MeOH) 240 mμ.

EXAMPLE 96

1-(2-Benzyloxy-3-octadecyloxy)propyl-3-(2-hydroxy)ethylurasil

In 30 ml of tetrahydrofuran and 6 ml of water was dissolved 570 mg (0.868 mmole) of the tetrahydropyranyl derivative as obtained in Example 95, and 2 ml of conc. hydrochloric acid was added to the solution, followed by stirring at room temperature for 1 hour. The reaction solution was concentrated to dryness under reduced pressure, and the residue was purified by 10 g of silica gel, with chloroform-methanol (195:5) used as an eluent to give 496 mg (yield of 100%) of a colorless solid.

TLC [silica gel, CHCl₃, MeOH (19:1)] Rf=0.25.

IR (film) cm⁻¹: 3460, 2920, 2850, 1700, 1465, 1345, 1220, 1120, 1090, 1060, 825, 770.

EXAMPLE 97

1-(2-Benzyloxy-3-octadecyloxy)propyl-3-(2-chloroethyl)urasil

In 2.5 ml of dichloromethane were dissolved 510 mg (0.868 mmole) of the hydroxy derivative as obtained in Example 96, 339 mg (1.78 mmole) of tosyl chloride and 282 mg (3.56 mmole) of pyridine, and the solution was stirred at room temperature for 16 hours. After 20 ml of dichloromethane and 20 ml of 2.5% aqueous hydrogencarbonate solution were added to the reaction solution, the mixture was shaken thoroughly and the dichloromethane layer was separated. The dichloromethane layer separated was washed with 0.5N hydrochloric acid and water successively, dried over sodium sulfate and concentrated to dryness under reduced pressure to give 513 mg (yield of 100%) of the subject chloride.

TLC [silica gel; CHCl₃, MeOH (19:1)] Rf=0.93.

IR (film) cm⁻¹: 2940, 2850, 1715, 1670, 1460, 1400, 1370, 1350, 1120.

NMR (60 MC, CDCl₃) δ:0.85(3H), 1.25(32H), 3.48(4H), 3.68(2H), 3.82(1H), 4.03(2H), 4.25(2H), 4.50(2H), 5.57(1H), 7.12(1H), 7.20(5H).

EXAMPLE 98

1-(2-Benzyloxy-3-octadecyloxy)propyl-3-(2-thiazolioethyl)urasil chloride

In 1 ml of thiazole was dissolved 30 mg (0.051 mmole) of the chloride as obtained in Example 97, and the solution was heated at the temperature of oil bath of 120° C. overnight. The reaction solution was concentrated to dryness under reduced pressure, and the residue was purified by 2 g of silica gel with chloroform-methanol-water (65:25:4) to give 6.2 mg (yield of 18.0%) of a colorless solid.

TLC [silica gel; n—BuOH—AcOH—H₂O (4:1:1)] Rf=0.19.

EXAMPLE 99

1-(2-Benzyloxy-3-octadecyloxy)propyl-3-(2-trimethylammonioethyl)urasil chloride

In 10 ml of 20% trimethylamine-toluene solution was dissolved 490 mg (0.83 mmole) of the chloride as obtained in Example 97, and the solution was heated at 120° C. for 24 hours. The reaction solution was concentrated to dryness under reduced pressure, and the residue was purified by 5 g of silica gel with chloroform-methanol-water (65:25:4) used as an eluent to give 115 mg (yield of 21.3%) of a colorless solid.

TLC [silica gel; CHCl₃—MeOH—H₂O (65:25:4)] Rf=0.31.

NMR (60 MC, CDCl₃+CD₃OD): δ:0.87(3H), 1.25(32H), 3.30(9H), 3.47(4H), 3.67(2H), 3.87(1H), 4.22(2H), 4.52(2H), 5.67(1H), 7.13(1H), 7.20(5H).

EXAMPLE 100

1-(2-Hydroxy-3-octadecyloxy)propyl-3-(2-trimethylammonio)ethylurasil chloride

In 5 ml of 60% acetic acid was dissolved 112 mg (0.17 mmole) of the trimethylammonium derivative as obtained in Example 99, and the solution was stirred in the presence of 20 mg of palladium carbon under a hydrogen atmosphere for 4 hours. The insoluble material was removed by filtration from the reaction solution, and washed with a small amount of methanol, and the filtrate and washing were combined and concentrated to dryness under reduced pressure to give 95 mg (yield of 100.0%) of a colorless solid material.

TLC [silica gel, CHCl₃—MeOH—H₂O (65:25:4)] Rf=0.19.

EXAMPLE 101

1-(2-Dimethylcarbamoylmoxy-3-octadecyloxy)propyl-3-(2-trimethylammonio)ethylurasil chloride In 0.5 ml of dichloromethane were dissolved 47.5 mg (0.085 mmole) of the hydroxy derivative as obtained in Example 100, 0.1 ml of phenyl chlorocarbonate and 0.1 ml of pyridine, and the solution was stirred at room temperature for 2 hours. The reaction solution was concentrated to dryness under reduced pressure, and the residue was dried thoroughly and treated with 5 ml of 20% dimethylamine-toluene solution, followed by allowing the mixture to stand at room temperature overnight. The reaction solution was concentrated to dryness under reduced pressure, and the residue was dissolved in 20 ml of 20% methanol. The solution was passed through a column of 15 ml of XAD-11 for adsorption, and after the column was washed with 80% methanol, elution was effected with 40 ml of methanol. The eluate was concentrated to dryness under reduced pressure, and the residue was purified by 2 g of silica gel with chloroform-methanol-water (65:25:4) used as an eluent to give 30 mg (yield of 55.9%) of a colorless solid.

TLC [silica gell CHCl₃—MeOH—H₂O (65:25:4)] Rf=0.39.

IR (film) cm⁻¹: 3360, 2920, 2850, 1710, 1660, 1400, 1240, 1220, 1195, 1125, 930, 915.

NMR (90 MC, CDCl₃) δ:0.87(3H), 1.23(32H), 2.83(6H), 3.47(9H), 3.58(4H), 3.85(4H), 4.37(2H), 5.15(1H), 5.73(1H), 7.20(1H), 7.25(5H).

EXAMPLE 102

1-(2-Acetyloxy-3-octadecyloxy)propyl-3-(2-trimethylammonioethyl)urasil chloride

In 0.5 ml of acetic anhydride and 0.5 ml of pyridine was dissolved 47.5 mg (0.085 mmole) of the hydroxy derivative as obtained in Example 100, and the solution was heated at 50° C. for 1 hour. The reaction solution was concentrated to dryness under reduced pressure, and the residue was purified by 2 g of silica gel with chloroform-methanol-water (65:25:4) used as en eluent to give 42 mg (yield of 82.0%) of a colorless solid.

TLC [silica gel; CHCl₃—MeOH—H₂O (65:25:4)] Rf=0.43.

IR (film) cm⁻¹: 3400, 2930, 2850, 1730, 1705, 1655, 1460, 1370, 1235, 1120, 1060, 1010, 810, 760.

NMR (60 MC, CDCl₃) δ:0.92(3H), 1.23(32H), 2.03(3H), 3.30(9H), 3.58(4H), 3.67(2H), 4.15(2H), 4.38(2H), 5.25(1H), 7.25(1H).

EXAMPLE 103

3-[N-Acetyl-N-(2-pyridyl)methyl]carbamoyl-2-methyl-1-octadecylcarbamoylglycerol

In 7 ml of chloroform was dissolved 252 mg of 3-O-[N-(2-pyridyl)methyl]carbamoyl-2-O-methyl-1-O-octadecylcarbamoylglycerol as obtained in Example 46-(i), and 5.5 ml of triethylamine and 1 ml of acetic anhydride were added to the solution, followed by heating under reflux for 3 days. After cooling, 3% sodium hydrogencarbonate was added to the reaction solution, and the mixture was extracted with chloroform. The organic layer was dried over magnesium sulfate and the solvent was distilled off under reduced pressure. The resulting residue was purified by column chromatography [silica gel, 15 g; eluent, n-hexane-ethyl acetate; 1:2] to give 89 mg of the objective compound.

TLC: Rf=0.33 [silica gel, n-hexane-ethyl acetate, 1:3].

IR (KBr) cm⁻¹: 3370, 2923, 2850, 1740, 1700, 1600, 1535, 1475, 1370, 1232, 1090, 1065, 985, 775.

NMR (90 MHz, CDCl₃) δ:0.88(3H,t,Me), 1.28(32H,s,CH₂), 2.60 (3H,s,NAc), 3.12(2H,q,CONHCH₂), 3.29(3H,s,OMe), 3.46 (1H,quint,CH-O), 3.98(2H,d,CH₂ CO), 4.21(2H,d,CH₂OCO), 4.92(1H,broad t NH), 5.09(2H,s,CH₂-pyridyl), 7.11, 7.60, 8.48(4H,pyridine).

EXAMPLE 104

3-O-[N-Acetyl-N-(N-methylpridnio-2-yl)methyl]carbamoyl-2-O-methyl-1-O-octadecylcarbamoylglycerol chloride To 85 mg of the compound as obtained in Example 103 was added 0.5 ml of methyl iodide, and the mixture was refluxed for 2 days, under shielding from light. After cooling, the reaction solution was concentrated under reduced pressure, and the residue was treated with IRA-410 [Cl⁻] (5 ml, eluent: MeOH-H₂O, 7:3). The resulting crude chloride derivative was purified by column chromatography [silica gel, 5 g; eluent, chloroform-methanol, 6:1 to 4:1] to give 52 mg of the objective compound.

TLC: Rf=0.17 (silica gel, CHCl$_3$:MeOH, 4:1)

IR (film) cm$^{-1}$: 3340, 2920, 2850, 1740, 1700, 1630, 1465, 1370, 1210.

NMR (90 MHZ, CDCl$_3$) δ:0.88(3H,t,Me), 1.24(32H,s,CH$_2$), 2.61 (3H,s,NAc), 3.10(2H,q,CONH CH$_2$), 3.38(3H,s,OMe), 3.70 (1H,m,CHO), 3.99(4H,m,CH$_2$OCOx2), 4.35(1H,m,NH), 4.70(3H,s,NMe), 5.43(2H,br,s,CH$_2$-pyridinio), 7.71, 8.02, 8.43, 9.65(4H,m,pyridinio).

EXAMPLE 105

2-O-Methyl-1-O-octadecylcarbamoyl-3-O-(N-acetyl-N-2-trimethylammonioethyl)carbamoylglycerol acetate In 20 ml of 75% methanol was dissolved 350 mg (0.5 mmole) of the iodide as obtained in Example 25, and the solution was passed slowly through a column (15 ml) of IRC-410 (acetate type), followed by washing with a small amount of 75% methanol. The effluent and washing were combined and concentrated to dryness under reduced pressure, and the residue was recrystallized from a mixture of 1 ml of ether and 4 ml of n-hexane to give 315 mg (yield of 100%) of a strongly hygroscopic colorless powder.

Elemental analysis, for C$_{33}$H$_{65}$N$_3$O$_8$·1.5H$_2$O: Calcd.: C, 60.15; H, 10.40; N, 6.33; I, 0. Found: C, 60.22; H, 10.87; N, 6.32; I, 0.

EXAMPLE 106

1-Methyl-2-[N-acetyl-N'-(3-octadecylcarbamoyloxy-2-methoxypropyl)ureido]methylpyridinium chloride (i) 2-[N'-(3-octadecylcarbamoyloxy-2-methoxypropyl)ureido]methylpyridine In 5 ml of toluene was dissolved 200 mg (0.5 mmole) of the amino derivative as obtained in Example 80, and 181 μl (1.5 mmole) of diphosgene was added to the solution, followed by stirring at room temperature for 10 minutes under a nitrogen atmosphere and further at 79° C. for 5 hours. After cooling, the reaction solution was concentrated under reduced pressure to give a crude isocyanate derivative.

In 2 ml of chloroform was dissolved the isocyanate derivative, and 61 μl (0.6 mmole) of 2-(aminomethyl)-pyridine was added to the solution under ice-cooling. The reaction solution was stirred at room temperature for 17.5 hours and concentrated under reduced pressure. The resulting crude product was purified by column chromatography [silica gel: 20 g; eluent:-chloroform-methanol=20:1] to give 206 mg (77.0%) of the objective compound as a colorless solid.

TLC [silica gel: CHCl$_3$/MeOH(20/1)]: Rf=0.27.

NMR [90 MHz, CDCl$_3$]δ:0.86(3H, t), 1.25(32H, s), 3.12(2H, q), 3.37(3H, s), 3.30-3.55(3H, m), 4.12(2H, m), 4.47(2H, d), 5.25(1H, br), 5.58(1H, br, t), 6.04(1H, br, t), 7.18(2H, m), 7.62(1H, d, t), 8.47(1H, br, d).

IR [KBr] cm$^{-1}$: 3330, 2920, 2855, 1695, 1635, 1590, 1539, 1478, 1442, 1290, 1280, 1262, 1251, 1235, 1139, 1105, 1055.

(ii) 2-[N-Acetyl-N'-(3-octadecylcarbamoyloxy-2-methoxypropyl)ureido]methylpyridine In 5 ml of chloroform was dissolved 200 mg (0.374 mmole) of the compound as obtained in (i), and 3.8 ml of triethylamine and 0.7 ml of acetic anhydride were added to the solution, followed by refluxing for 2 days under a nitrogen atmosphere. After cooling, the reaction solution was treated with 3% aqueous NaHCO$_3$ solution and extracted with chloroform. The organic layer was dried over magnesium sulfate and the solvent was distilled off under reduced pressure. The resulting crude product was purified by column chromatography [silica gel: 10 g; eluent: n-hexane/ethyl acetate=½] to give 158 mg (73.2%) of the objective compound as a pale brown solid.

TLC[silica gel; n-hexane/AcOEt(½)] Rf=0.32.

NMR[90 MHz, CDCl$_3$] δ:0.87(3H, t), 1.26(32H, s), 2.31(3H, s), 3.15(2H, q), 3.26-3.72(3H, m), 3.43(3H, s), 4.18(2H, m), 5.05(2H, s), 5.14(1H, br), 7.09-7.37(2H, m), 7.67(1H, d, t), 8.51(1H, m), 9.58(1H, br).

IR [KBr]cm$^{-1}$: 3320, 2920, 2850, 1717, 1698, 1660, 1530, 1395, 1275, 1262, 1200.

(iii) 1-Methyl-2-[N-acetyl-N'-(3-octadecylcarbamoyloxy-2-methoxypropyl)ureido]methylpyridinium chloride To 150 mg (0.26 mmole) of the compound as obtained in (ii) was added 2 ml of methyl iodide, and the mixture was refluxed for 3 days under a nitrogen atmosphere under shielding from light. After cooling, the reaction solution was concentrated to dryness, and the residue was treated with IRA-410 (Cl$^-$ type) [15 ml; eluent: 70% methanol-water]. The resulting crude chloride derivative was purified by reprecipitation from acetone-petroleum ether to give 131 mg (80.3%) of the objective compound as a colorless solid).

TLC[silica gel;AcOEt/AcOH/H$_2$O(3/1/1)] Rf=0.26.

NMR[90 MHz, CDCl$_3$] δ:0.87(3H, t), 1.24(32H, s), 2.55(3H, s), 3.10(2H, q), 3.27-3.65(3H, m), 3.38(3H, s), 4.08(2H, m), 4.71(3H, s), 5.10(1H, br), 5.62(2H, br, s), 7.66(1H, m), 7.85(1H, m), 8.30(1H, m), 9.27(1H, br, t), 9.48(1H, m)

IR[KBr]cm$^{-1}$: 3400, 2923, 2850, 1710, 1635, 1530, 1470.

EXAMPLE 107

[N-Acetyl-N'-(3-octadecylcarbamoyloxy-2-methoxypropyl)ureido]ethyltrimethylammonium chloride (i) N-(dimethylamino)ethyl-N'-(3-octadecylcarbamoyloxy-2-methoxy)propylurea In 25 ml of toluene was dissolved 1.00 g (2.5 mmole) of the amino derivative as produced in Example 80, and 905 μl (7.5 mmole) of diphosgene was added to the solution, followed by heating at 80° C. for 5 hours. After cooling, the reaction solution was concentrated under reduced pressure to give a crude isocyanate derivative.

In 10 ml of chloroform was dissolved the isocyanate derivative, and 331 mg (3.75 mmole) of asym.-dimethylethylenediamine was added to the solution, followed by stirring at room temperature for 16 hours and refluxing for 2 hours. The reaction solution was concentrated under reduced pressure and the crude product was purified by column chromatography [silica gel: 50 g; eluent: chloroform-methanol=20:1 to 3:1] to give 470 mg (36.5%) of the objective compound as a colorless solid.

TLC[silica gel: CHCl$_3$/MeOH(3/1) Rf=0.26.

NMR[90 MHz, CDCl$_3$] δ:0.87(3H, t), 1.24(32H, s), 2.37(6H, s), 2.61(2H, t), 3.14(2H, q), 3.20-3.63(5H, m), 3.41(3H, s), 4.15(2H, br), 5.42(1H, br), 5.84(2H, br, t).

IR[KBr]cm$^{-1}$: 3350, 2925, 2850, 1695, 1630, 1590, 1540, 1470.

(ii) N-Acetyl-N-(dimethylamino)ethyl-N'-(3-octadecylcarbamoyloxy-2-methoxy)propylurea To 129 mg (0.25 mmole) of the compound as synthesized in (i) were added 0.5 ml of acetic anhydride and 3 ml of triethylamine, and the reaction solution was refluxed for 4 hours under a nitrogen gas stream. The reaction solution was treated with chloroform and washed with 5% NaHCO$_3$ solution. The organic layer was dried over sodium sulfate and concentrated under reduced pressure. The resulting crude product was purified by column chromatography [silica gel: 8 g; eluent: acetone] to give 139 mg (100%) of the objective compound as a colorless oil.

TLC[silica gel: acetone] Rf=0.13

NMR[90 MHz, CDCl$_3$] δ:0.87(3H, t), 1.26(32H, s), 2.28(6H, s), 2.33(3H, s), 2.50(2H, t), 3.15(2H, q), 3.36–3.63(3H, m), 3.43(3H, s), 3.76(2H, t), 4.16(2H, d), 5.03(1H, br), 9.68(1H, br).

IR[film]cm$^{-1}$: 3320, 2930, 2855, 1708, 1660, 1539, 1470, 1370, 1250.

(iii) [N-Acetyl-N'-(3-octadecylcarbamoyloxy-2-methoxypropyl)ureido]ethyltrimethylammonium chloride To 139 mg (0.25 mmole) of the compound as synthesized in (ii) was added 2 ml of methyl iodide, and the reaction solution was stirred at room temperature for 2 days in a shade and concentrated under reduced pressure. The resulting crude product was reprecipitated from acetone-petroleum ether to give 150 mg of an iodide derivative. The iodide derivative was treated with IRA-410 (Cl$^-$ type) [10 ml; eluent: 70% methanol/water) to give 135 mg (88.9%) of the objective compound as a colorless powder.

TLC[silica gel; AcOEt/AcOH/H$_2$O(3/1/1)] Rf=0.69.

NMR[90 MHz, CDCl$_3$] δ:0.86(3H, t), 1.25(32H, s), 2.55(3H, s), 3.12(2H, q), 3.32–3.72(3H, m), 3.42(3H, s), 3.49(9H, s), 3.82–4.45(6H, m), 5.14(1H, br), 9.30(1H, br).

IR[KBr]cm$^{-1}$: 3430, 2925, 2855, 1710, 1668, 1540, 1468, 1390, 1259, 1200.

EXAMPLE 108

1-Ethyl-2-[N-acetyl-N-(3-octadecylcarbamoyloxy-2-methoxypropyloxy)carbonyl]aminomethylpyridinium chloride To 140 mg (0.243 mmole) of the compound as produced in Example 103 was added 3 ml of iodethane, and the reaction solution was refluxed for 3 days under a nitrogen atmosphere. After cooling, the reaction solution was concentrated to dryness and the residue was treated with IRA-410 (Cl$^-$ type) [15 ml; eluent: 70% methanol/water] to give 192 mg of a crude chloride derivative. This crude chloride derivative was dissolved in acetone and cooled with ice, and the precipitate which was separated out was collected by filtration to give 120 mg (76.9%) of the objective compound as a colorless powder.

TLC[silica gel; CHCl$_3$/MeOH(3/1)] Rf=0.32.

NMR[90 MHz, CDCl$_3$] δ:0.88(3H, t), 1.25(32H, s), 1.71(3H, t), 2.65(3H, s), 3.12(2H, q), 3.38(3H, s), 3.66(1H, quint), 4.02(2H, br, d), 4.37(2H, m), 5.20(2H, q), 5.31(1H, br), 5.48(2H, br, s), 7.75(1H, br, d), 8.06(1H, br, t), 8.47(1H, br, t), 10.00(1H, br, d).

IR[KBr]cm$^{-1}$: 3405, 2930, 2850, 1754, 1700, 1638, 1224.

EXAMPLE 109

1-Ethoxycarbonylmethyl-2-[N-acetyl-N-(3-octadecylcarbamoyloxy-2-methoxypropyloxy)carbonyl]aminomethylpyridinium chloride To 173 mg (0.3 mmole) of the compound as produced in Example 103 was added 1 ml of ethyl chloroacetate, and the reaction solution was heated at 50° C. for 2 hours and further at 90° C. for 24 hours. After cooling, the reaction solution was concentrated under reduced pressure, and the resulting crude product was purified by column chromatography [silica gel: 10 g; eluent: chloroform/methanol=4/1] to give 62 mg (29.5%) of the objective compound as a pale brown powder.

TLC[silica gel; CHCl$_3$/MeOH(3/1)] Rf=0.30.

NMR[90 MHz, CDCl$_3$] δ:0.86(3H, t), 1.24(32H, s), 1.37(3H, m), 2.59(3H, s), 3.13(2H, q), 3.37(3H, s), 3.70(1H, m), 3.89–4.56(6H, m), 5.31(3H, br), 6.32(2H, br), 7.86, 8.10, 8.55, 9.90(each 1H, m).

IR[KBr]cm$^{-1}$: 3380, 2925, 2850, 1750, 1700, 1627, 1525, 1465, 1420, 1375, 1348, 1220.

EXAMPLE 110

1-[(2-methoxy-3-octadecylcarbamoyloxy)propyl]-3-(2-thiazolioethyl)hydantoin chloride (i) 2-Methyl-3-tritylglycerol In 150 ml of methylene chloride were dissolved 13.60 g (64.7 mmole) of 1-benzoyl-2-methylglycerol and 10.23 g (129.4 mmole) of pyridine, and 27.05 g (97.0 mmole) of trityl chloride was added to the solution under ice-cooling. The reaction solution was stirred at room temperature for 18 hours and washed with water. The organic layer was dried over anhydrous potassium carbonate and the solvent was distilled off under reduced pressure.

The residue was dissolved in 30 ml of dioxane and 250 ml of ethanol, and 10% aqueous sodium hydroxide solution was added to the solution, followed by reflux for 20 hours. After cooling, the reaction solution was concentrated under reduced pressure, and water was added to the residue, followed by extraction with chloroform. The organic layer was dried over anhydrous potassium carbonate and the solvent was distilled off under reduced pressure. The resulting crude product was purified by column chromatography [silica gel: 300 g; eluent: n-hexane/ethyl acetate=3/1] to give 22.48 g (99.7%) of the objective compound as a pale yellow oil.

TLC[silica gel; n-hexane/ethyl acetate (3:1)] Rf=0.17.

NMR[90 MHz, CDCl$_3$] δ:2.13(1H, br), 3.22(2H, m), 3.38(3H, s), 3.67(2H, m), 7.19–7.54(15H, m).

IR[film]cm$^{-1}$: 3420, 3025, 2940, 2875, 2830, 1600, 1490, 1220, 1132, 1080, 1040, 780, 768, 750, 710.

(ii) 2-Methyl-3-p-toluenesulfonyl-1-tritylglycerol

In 40 ml of methylene chloride were dissolved 3.484 g (10 mmole) of the alcohol derivative as synthesized in (i) and 3.036 g (30 mmole) of triethylamine, and 2.478 g (13 mmole) of p-toluenesulfonyl chloride was added to the solution under ice-cooling. The reaction solution was stirred at room temperature for 17 hours, treated with 1N hydrochloric acid and extracted with chloroform. The organic layer was dried over magnesium sulfate and the solvent was distilled off under reduced pressure. The resulting crude product was purified by column chromatography [silica gel: 170 g; eluent: n-hexane/ethyl acetate=5/1 to 3/1] to give 4.491 g (89.4%) of the objective compound as a colorless solid.

TLC[silica gel: n-hexane/ethyl acetate (3/1)] Rf=0.43.

NMR[90 MHz, CDCl$_3$] δ:2.37(3H, s), 3.12(2H, d), 3.22(3H, s), 3.40(1H, quint), 4.13(2H, m), 7.04–7.48(17H, m), 7.73(2H, d).

IR[KBr]cm$^{-1}$: 3060, 2930, 2890, 2870, 2820, 1599, 1450, 1370, 1190, 1180, 1100, 1080, 980, 790, 770, 715.

(iii) 3-(2-Benzyloxyethyl)-1-[1-(2-methoxy-3-trityloxy)propyl]hydantoin

In 12 ml of dimethylsulfoxide were dissolved 6.031 g (12 mmole) of the tosylate derivative as synthesized in (ii) and 1.406 g (6 mmole) of 3-(2-benzyloxyethyl)-hydantoin, and 673 mg (12 mmole) of powdered potassium hydroxide was added to the solution. The reaction solution was stirred at room temperature for 17.5 hours, treated with 1N hydrochloric acid (12 ml) and extracted with ethyl acetate. The organic layer was washed with water and dried over magnesium sulfate and the solvent was distilled off under reduced pressure. The resulting crude product was purified by column chromatography [silica gel: 250 g; eluent: n-hexane/ethyl acetate = 1.5/1] to give 2.793 g (82.4%) of the objective compound as a viscous material.

TLC[silica gel; n-hexane/ethyl acetate (1/1)] Rf=0.49

NMR[90 MHz, CDCl$_3$] δ:3.18(2H, m), 3.28(3H, s), 3.48(2H, m), 3.67(4H, t), 3.75(1H, m), 3.87(2H, ABq), 4.48(2H, s), 7.12-7.69(20H, m).

IR[film]cm$^{-1}$: 3070, 3030, 2940, 2875, 1775, 1720, 1600, 1470, 1115, 1080, 760, 710.

(iv) 3-(2-Benzyloxyethyl)-1-[(3-hydroxy-2-methoxy)propyl]hydantoin

In 65 ml of tetrahydrofuran was dissolved 2.259 g (4 mmole) of the compound as synthesized in (iii), and 5 ml of water and 5 ml of conc. hydrochloric acid was added to the solution, followed by reflux for 1 hour and 20 minutes. After cooling, the reaction solution was concentrated under reduced pressure, neutralized with 1N sodium hydroxide solution and extracted with chloroform. The organic layer was dried over magnesium sulfate and the solvent was distilled off under reduced pressure. The resulting crude product was purified by column chromatography [silica gel: 50 g; eluent: ethyl acetate] to give 1.093 g (84.8%) of the objective compound as a colorless oil.

TLC[silica gel: AcOEt] Rf=0.30.

NMR[90 MHz, CDCl$_3$] δ:2.90(1H, t), 3.38(3H, s), 3.41-3.65(4H, m), 3.70(4H, t), 3.80(1H, m), 3.98(2H, ABq), 4.50(2H, s), 7.28(5H, s).

IR[film]cm$^{-1}$: 3450, 2940, 2870, 1765, 1710, 1470, 1110, 760.

(v) 3-(2-Benzyloxyethyl)-1-[(2-methoxy-3-octadecylcarbamoyloxy)propyl]hydantoin

In 20 ml of pyridine was dissolved 1.093 g (3.391 mmole) of the alcohol derivative as synthesized in (iv), and 2.00 g (6.781 mmole) of stearyl isocyanate was added to the solution, followed by warming at 70° C. for 22 hours. A mixture of n-hexane/ethyl acetate (1/1.5) was added to the reaction solution and the precipitate was removed by filtration. The filtrate was concentrated under reduced pressure and the resulting crude product was purified by column chromatography [silica gel: 80 g; eluent: n-hexane/ethyl acetate = 1/1.5] to give 1.914 g (91.4%) of the objective compound as a viscous material.

TLC[silica gel; n-hexane/ethyl acetate (1/1.5)] Rf=0.39

NMR[90 MHz, CDCl$_3$] δ:0.89(3H, t), 1.28(32H, s), 3.13(2H, q), 3.29(3H, s), 3.47-3.68(2H, m), 3.72(4H, t), 3.80(1H, m), 3.97(2H, s), 4.12(2H, d), 4.53(2H, s), 4.90(1H, br), 7.30(5H, s)

IR[film]cm$^{-1}$: 3320, 2920, 2850, 1765, 1700, 1525, 1462, 1245, 1100

(vi) 3-(2-Hydroxyethyl)-1-[1-(2-methoxy-3-octadecylcarbamoyloxy)propyl]hydantoin To 1.853 g (3 mmole) of the compound as synthesized in (v) and 600 mg of 10% Pd/C was added 90% aqueous acetic acid solution, and catalytic reduction was conducted at room temperature for 14 hours. After the catalyst was removed by filtration, the filtrate was concentrated under reduced pressure and the resulting crude product was purified by column chromatography [silica gel: 50 g; eluent: ethyl acetate] to give 1.429 g (90.3%) of the objective compound as a colorless powder.

TLC[silica gel: AcOEt] Rf=0.47

NMR[90 MHz, CDCl$_3$] δ:0.89(3H, t), 1.28(32H, s), 3.16(2H, q), 3.41(3H, s), 3.50-3.70(2H, m), 3.76(4H, m), 3.83(1H, m), 4.03(2H, s), 4.16(2H, m), 5.00(1H, br)

IR[KBr]cm$^{-1}$: 3430, 2930, 2850, 1765, 1710, 1690, 1542, 1480.

(vii) 1-[(2-Methoxy-3-octadecylcarbamoyloxy)propyl]-3-(2-p-toluenesulfonyloxyethyl)hydantoin In 10 ml of methylene chloride were dissolved 1.429 g (2.708 mmole) of the alcohol derivative as synthesized in (vi) and 30 ml of triethylamine, and 619 mg (3.249 mmole) of p-toluenesulfonyl chloride was added to the solution under ice-cooling, followed by stirring at room temperature for 3 days. To the reaction solution was added 1N hydrochloric acid solution and extraction with chloroform was conducted. The organic layer was dried over magnesium sulfate and the solvent was distilled off under reduced pressure. The resulting crude product was purified by column chromatography [silica gel: 80 g; eluent: n-hexane/ethyl acetate = 1/1.5] to give 1.846 g (100%) of the objective compound as a viscous material.

TLC[silica gel; n-hexane/ethyl acetate (1/1.5)] Rf=0.31.

NMR[90 MHz, CDCl$_3$] δ:0.88(3H, t), 1.28(32H, s), 2.43(3H, s), 3.16(2H, q), 3.40(3H, d), 3.45-3.68(2H, m), 3.75(2H, t), 3.70-3.88(1H, m), 3.98(2H, ABq), 4.12(2H, d), 4.25(2H, t), 4.85(1H, br), 7.32(2H, d), 7.78(2H, d).

IR[film]cm$^{-1}$: 3330, 2920, 2850, 1770, 1710, 1598, 1525, 1465, 1360, 1240, 1190, 1180, 760.

(viii) 1-[(2-Methoxy-3-octadecylcarbamoyloxy)propyl]-3-(2-thiazolioethyl)hydantoin chloride To 44 mg (0.065 mmole) of the tosyl compound as synthesized in (vii) was added 0.5 ml of thiazole, and the reaction mixture was heated at 88°-90° C. for 40 hours under a nitrogen atmosphere. The reaction solution was concentrated under reduced pressure and the residue was treated with IRA-410 (Cl type) [5 ml; eluent: methanol/water = 7/3] and the resulting crude chloride derivative was purified by column chromatography (silica gel: 4 g; eluent: chloroform/methanol/water = 65/25/1) to give 12 mg (29.2%) of the objective compound as a colorless powder.

TLC[silica gel; CHCl$_3$/MeOH/H$_2$O (65/25/1)] Rf=0.13

NMR[90 MHz, CDCl$_3$] δ:0.85(3H, t), 1.23(32H, s), 3.09(2H, q), 3.38(3H, s), 3.41-4.28(11H, m), 5.04(1H, br), 8.21, 8.76, 11.05(each 1H, br).

IR[film]cm$^{-1}$: 3300, 2920, 2850, 1763, 1700, 1520, 1465.

EXAMPLE 111

1-[(2-Methoxy-3-octadecylcarbamoyloxy)propyl]-3-[2-(1-methylimidazolio)ethyl]hydantoin chloride (i) 3-(2-Iodoethyl)-1-[(2-methoxy-3-octadecylcarbamoyloxy)-propyl]hydantoin In 30 ml of acetone were dissolved 1.846 g (2.708 mmole) of the compound as synthesized in Example 110-(vii) and 609 mg (4.062 mmole) of sodium iodide, and the solution was refluxed for 31 hours under shielding from light. After cooling, the reaction solution was concentrated under reduced pressure and chloroform was added to the residue. The precipitate was removed by filtration and the filtrate was concentrated under reduced pressure. The resulting crude product was purified by column chromatography [silica gel: 55 g; eluent: n-hexane/ethyl acetate=1/1] to give 1.418 g (82.1%) of the objective compound as a colorless solid.

TLC[silica gel; n-hexane/ethyl acetate (1/1)] Rf=0.32.

NMR[90 MHz, CDCl$_3$] δ:0.88(3H, s), 1.25(32H, s), 3.16(2H, q), 3.33(2H, t), 3.40(3H, s), 3.53(2H, m), 3.72(1H, m), 3.89(2H, t), 4.03(2H, s), 4.14(2H, d), 4.81(1H, br)

IR[KBr]cm$^{-1}$: 3330, 2920, 2850, 1770, 1718, 1698, 1540, 1480, 1277, 1265, 1250, 1125.

(ii) 1-[(2-Methoxy-3-octadecylcarbamoyloxy)-propyl]-3-[2-(1-methylimidazolio)ethyl]hydantoin chloride To 128 mg (0.2 mmole) of the compound as synthesized in (i) was added 164 mg (2 mmole) of 1-methylimidazole, and the reaction solution was heated at 60° C. for 24 hours under a nitrogen atmosphere and concentrated under reduced pressure. The residue was treated with IRA-410 (Cl type) [6 ml; eluent: methanol/water=7/3] and the resulting chloride derivative was purified by column chromatography (silica gel: 6 g; eluent: chloroform/methanol/water=65/25/1) to give 115 mg (91.5%) of the objective compound as a colorless powder.

TLC[(silica gel: CHCl$_3$/MeOH/H$_2$O(65/25/1)] Rf=0.29

NMR[90 MHz, CDCl$_3$] δ:0.88(3H, t), 1.27(32H, s), 3.15(2H, q), 3.42(3H, s), 3.58(2H, m), 3.73(1H, m), 3.89-4.30(9H, m), 4.68(2H, br), 5.38(1H, br), 7.43 and 7.75(each 1H, br, s), 10.36(1H, br, s)

IR[KBr]cm$^{-1}$: 3425, 2925, 2850, 1770, 1710, 1530, 1470, 1252.

EXAMPLE 112

1-[(2-Methoxy-3-octadecylcarbamoyloxy)propyl]-3-[2-(1-methylpyrrolidinio-1-yl)ethyl]hydantoin chloride To 128 mg (0.2 mmole) of the compound as synthesized in Example 111-(i) was added 170 mg (2 mmole) of 1-methylpyrrolidine, and the reaction solution was heated at 60° C. for 24 hours under a nitrogen atmosphere and concentrated under reduced pressure. The residue was treated with IRA-410 (Cl type) [6 ml; eluent: methanol/water=7/3) and the resulting crude chloride derivative was purified by column chromatography (silica gel: 6 g; eluent: chloroform/methanol/water=65/25/1) to give 120 mg (95.0%) of the objective compound as a colorless powder.

TLC[silica gel: CHCl$_3$/MeOH/H$_2$O(65/25/1)] Rf=0.24.

NMR[90 MHz, CDCl$_3$] δ:0.88(3H, t), 1.26(32H, s), 2.29(4H, br), 3.15(2H, q), 3.40(3H, s), 3.42(3H, s), 3.57(2H, m), 3.72(1H, m), 3.78-4.33(12H, m), 5.48(1H, br, t).

IR[KBr]cm$^{-1}$: 3460, 2920, 2853, 1765, 1702, 1539, 1470, 1255.

EXAMPLE 113

3-[2-(3-Methoxycarbonylpyridinio)ethyl]-1-[(2-methoxy-3-octadecylcarbamoyloxy)propyl]hydantoin iodide and 3-[2-(3-carboxylatopyridinio)ethyl]-1-[(2-methoxy-3-octadecylcarbamoyloxy)propyl]hydantoin iodide To 319 mg (0.5 mmole) of the compound as synthesized in Example 111-(i) was added 686 mg (5 mmole) of methyl nicotinate, and the reaction solution was heated at 80° C. for 24 hours under a nitrogen atmosphere and concentrated under reduced pressure. The resulting crude product was subjected to separation and purification by column chromatography (silica gel: 30 g; eluent: chloroform/methanol=5/1) to give from the former eluate 94 mg of the carboxylato derivative as a yellow powder and from the latter eluate 197 mg (50.9%) of the methoxycarbonyl derivative as a yellow powder.

Methoxycarbonyl derivative

TLC[silica gel: CHCl$_3$/MeOH(5/1)] Rf=0.24.

NMR[90 MHz, CDCl$_3$] δ:0.85(3H, t), 1.24(3H, s), 3.11(2H, q), 3.40(3H, s), 3.50(2H, m), 3.66(1H, m), 3.95-4.38(9H, m), 5.13(1H, br), 5.41(2H, br), 8.30(1H, t), 8.92(1H, d), 9.85(1H, s), 9.98(1H, d).

IR[KBr]cm$^{-1}$: 3450, 2920, 2850, 1770, 1710, 1640, 1535, 1470, 1440, 1308, 1248, 1205, 1160, 1130, 759.

Carboxylato derivative

TLC[silica gel: CHCl$_3$/MeOH(5/1)] Rf=0.37

NMR[90 MHz, CDCl$_3$] δ:0.88(3H, t), 1.28(32H, s), 3.14(2H, q), 3.35-3.81(6H, m), 3.89-4.40(6H, m), 4.55(1H, m), 5.29(2H, br), 8.29(1H, m), 8.95(1H, m), 9.63-10.02(2H, m).

IR[KBr]cm$^{-1}$: 3400, 2920, 2850, 1770, 1710, 1530, 1470, 1475, 1250.

EXAMPLE 114

3-[2-(4-Dimethylaminopyridinio)ethyl]-1-[(2-methoxy-3-octadecylcarbamoyloxy)propyl]hydantoin iodide In 2 ml of chloroform were dissolved 128 mg (0.2 mmole) of the compound as synthesized in Example 111-(i) and 244 mg (2 mmole) of 4-dimethylaminopyridine, and the reaction solution was refluxed for 28 hours. After cooling, the reaction solution was concentrated under reduced pressure and the residue was purified by column chromatography (silica gel: 12 g; eluent: chloroform/methanol/water=65/25/1) to give from the former eluate 7 mg (4.6%) of the objective compound as a colorless powder and from the latter eluate 188 mg of a mixture of the objective compound and 4-dimethylaminopyridine.

TLC[silica gel: CHCl$_3$/MeOH/H$_2$O(65/25/1) Rf=0.54

NMR[90 MHz, CDCl$_3$] δ:0.88(3H, t), 1.25(32H, s), 3.13(2H, q), 3.28(6H, s), 3.42(3H, s), 3.59(2H, m), 3.70(1H, m), 3.88-4.28(6H, m), 4.62(2H, m), 5.05(1H, br), 6.99 and 8.43 (each 2H, d).

IR[KBr]cm$^{-1}$: 3400, 2920, 2850, 1770, 1710, 1650, 1570, 1540, 1470, 1250.

EXAMPLE 115

1-[(2-Methoxy-3-octadecylcarbamoyloxy)propyl]-3-[2-(trimethylammonio)ethyl]hydantoin chloride To 230 mg (0.362 mmole) of the compound as synthesized in Example 111-(i) was added 10 ml of 20% trimethylaminetoluene solution, and the reaction solution was allowed to stand at room temperature for 2 weeks. The iodide which was separated out was treated with IRA-410 (Cl type) [15 ml; eluent: methanol/water=7/3) to give 219 mg (100%) of the objective compound as a colorless powder.

TLC[silica gel; $CHCl_3/MeOH/H_2O(65/25/1)$] Rf=0.35.

NMR[90 MHz, $CDCl_3$] δ:0.87(3H, t), 1.26(32H, s), 3.13(2H, q), 3.40-3.79(3H, m), 3.42(3H, s), 3.49(9H, br, s), 3.89-4.26(8H, m), 5.42(1H, br, t)

IR[KBr]$cm^{-1}$: 3415, 2930, 2855, 1768, 1710, 1540, 1473, 1255.

EXAMPLE 116

2-[N-(3-Octadecylcarbamoyloxy-2-ethoxypropyloxycarbonyl)amino]methyl-N-methylpyridinium chloride (i) 2-O-Ethyl-3-O-[N-(pyridin-2-yl)methyl]carbamoyl-1-O-octadecylcarbamoylglycerol To the carbonate derivative synthesized from 830 mg (2 mmole) of 2-O-ethyl-1-O-octadecylcarbamoylglycerol (m.p. 55°-56° C.), 344 mg (2.2 mmole) of phenyl chloroformate, 320 mg of pyridine and 10 ml of methylene chloride were added 260 mg of 2-(aminomethyl)pyridine and 5 ml of chloroform, and the reaction solution was refluxed for 12 hours and concentrated to dryness. The resulting product was purified by column chromatography [silica gel: 40 g; eluent: n-hexane-ethyl acetate (1:3)] to give 727 mg (66%) of the objective compound.

IR[KBr]$cm^{-1}$: 3325, 2925, 2850, 1697, 1540, 1470, 1270

NMR[60 MHz, $CDCl_3$] δ:0.87(3H), 1.08(3H, t), 1.27(32H, s), 3.16(2H, q), 3.3-4.0(3H, m), 4.18(4H, m), 4.50(2H, d), 4.80(1H, br), 5.90(1H, br), 7.20(2H, m), 7.65(1H, m), 8.50(1H, m).

(ii) 2-O-Ethyl-3-O-[N-acetyl-N-(pyridin-2-yl)methyl]carbamoyl-1-O-octadecylcarbamoylglycerol In 5 ml of pyridine was dissolved 285 mg of the carbamoyl derivative as obtained in (i), and 2 ml of acetic anhydride was added to the solution, followed by heating at 100° C. for 23 hours. The reaction solution was concentrated to dryness and the residue was purified by silica gel chromatography (eluent: n-hexane-ethyl acetate (1:1)] to give 228 mg (75%) of the objective compound.

IR[KBr]$cm^{-1}$: 3350, 2930, 2855, 1742, 1705, 1698, 1598, 1532, 1370, 1115, 1080, 980, 778, 760.

NMR[90 MHz, $CDCl_3$] δ:0.87(3H, t), 1.07(3H, t), 1.23(32H, s), 2.60(3H, s, Ac), 3.11(2H, q), 3.3-3.7(3H, m), 3.97(2H, d), 4.21(2H, m), 4.83(1H, br, NH), 5.08(2H, s, $CH_2Py$), 7.10(2H), 7.60(1H), 8.48(1H).

(iii) 2-[N-(3-Octadecylcarbamoyloxy-2-ethoxypropyloxycarbonyl)amino]methyl-N-methylpyridinium chloride To 222 mg of the compound as obtained in (ii) was added 1.5 ml of methyl iodide, and the solution was refluxed for 2 days. After cooling, the reaction solution was concentrated under reduced pressure and the residue was treated with IRA-410 (Cl type) [15 ml; eluent: MeOH—$H_2O$ (7:3)]. The resulting chloride derivative was purified by column chromatography [silica gel: 15 g; eluent: chloroformmethanol (4:1)] to give 125 mg of the objective compound.

NMR[60 MHz, $CDCl_3$] δ:0.87(3H, t), 1.12(3H), 1.25(32H, s), 2.64(3H, s, Ac), 3.14(2H), 3.60(2H, q), 3.8-4.6(6H), 4.72(3H, s, $N^-Me$), 5.45(2H, br-s, $CH_2$-Py), 7.6-8.6(3H, m), 9.60(1H).

EXAMPLE 117

2-[N-(3-Octadecylcarbamoyloxy-2-ethoxypropyloxycarbonyl)amino]methyl-N-ethylpyridinium iodide In 0.5 ml of ethyl iodide was dissolved 130 mg of the compound as obtained in Example 116-(iii), and the solution was refluxed for 27 hours, and purified by silica gel chromatography [eluent: chloroform to chloroformmethanol (20:1)] to give 103 mg of the objective compound.

IR(KBr)$cm^{-1}$: 3420, 2925, 2850, 1738, 1700, 1628, 1530, 1465, 1370, 1220, 1160, 985, 778.

NMR[90 MHz, $CDCl_3$] δ:0.87(3H, t), 1.15(3H, t), 1.25(32H, s), 1.73(3H, t), 2.66(3H, s, N-Ac), 3.11(2H, q), 3.61(2H, q), 3.85(1H, m), 4.02(2H), 4.39(2H), 4.93(1H, br, NH), 5.08(2H, q, $N^+-CH_2$), 5.47(2H, s, $CH_2$-Py), 7.84(1H), 8.05(1H), 8.41(1H), 9.64(1H).

EXAMPLE 118

3-Octadecylcarbamoyl-2-methyl-1-(pyridin-3-yl)carbamoylglycerol

In 10 ml of toluene were dissolved 0.615 g (5 mmole) of nicotinic acid, 1.515 g (5.05 mmole) of diphenylphosphorylazide and 0.6 g of triethylamine, and the reaction solution was stirred at room temperature for 2 hours and refluxed for 1 hour. The reaction solution was concentrated to about a half volume, and 1.9 g (4.74 mmole) of 3-octadecylcarbamoyl-2-methylglycerol was added to the resulting solution. The mixture was heated at 100° C. overnight and concentrated to dryness under reduced pressure. The residue was purified by silica gel (25 g) with chloroform as an eluent to give 1.74 g (yield 70.4%) of colorless crystals.

TLC[silica gel, $CHCl_3$—MeOH(19:1)] Rf=0.27 single spot.

NMR[60 MC, $CDCl_3$] δ:0.97(3H), 1.25(32H), 3.17(2H), 3.47(3H), 3.67(1H), 4.23(2H), 4.33(2H), 7.23(1H), 7.95(1H).

EXAMPLE 119

3-[(3-Octadecylcarbamoyloxy-2-methoxypropoxy)carbonylamino]1-methylpyridinium iodide In 2 ml of methyl iodide and 2 ml of dichloromethane was dissolved 300 mg (0.57 mmole) of the pyridine derivative as obtained in Example 118, and the solution was allowed to stand at room temperature for 2 days.

The reaction solution was concentrated to dryness under reduced pressure, and the residue was washed with n-hexane to give 375 mg (yield: 100%) of a colorless powder.

IR(KBr)$cm^{-1}$: 3310, 2920, 2850, 1730, 1695, 1550, 1510, 1460, 1270, 1240, 1160, 1060.

NMR(60 MC, $CDCl_3$) δ:0.87(3H), 1.25(32H), 3.17(2H), 3.45(3H), 3.70(1H), 4.20(4H), 4.50(3H), 5.13(1H), 7.90(1H), 8.70(1H), 8.87(1H), 9.38(1H), 9.93(1H).

EXAMPLE 120

3-Octadecylcarbamoyl-2-methyl-1-(N-acetyl-N-pyridin-3-yl)carbamoylglycerol

In a mixture of 3 ml of pyridine and 1.5 ml of acetic anhydride was dissolved 320 mg (0.613 mmole) of the pyridine derivative as obtained in Example 118, and the solution was refluxed for 3 hours. The reaction solution was concentrated to dryness under reduced pressure, and the residue was purified by silica gel (5 g) with chloroform as an eluent to give 203 mg (yield 58.7%) of a colorless solid.

TLC[silica gel; $CHCl_3$—MeOH(19:1)] Rf=0.52 single spot.

NMR(60 MC, $CDCl_3$) δ:0.92(3H), 1.23(32H), 2.65(3H), 3.07(2H), 3.25(3H), 3.40(1H), 3.90(2H), 4.20(2H), 4.90(1H), 7.43(2H), 8.40(1H), 8.57(1H).

EXAMPLE 121

3-[N-(3-Octadecylcarbamoyloxy-2-methoxypropoxycarbonyl)-N-acetyl]amino-1-methylpyridinium iodide In a mixture of 1 ml of dichloromethane and 2 ml of methyl iodide was dissolved 200 mg (0.35 mmole) of the acetate as obtained in Example 120, and the solution was allowed to stand at room temperature for 2 days, followed by concentration to dryness under reduced pressure. The residue was washed with n-hexane to give 246 mg (yield 100%) of a colorless powder.

TLC[silica gel; $CHCl_3$, MeOH, $H_2O$(65:25:4)] Rf=0.50 single spot.

IR(KBr)cm$^{-1}$: 3400, 2920, 2850, 1760, 1720, 1500, 1470, 1370, 1250, 1100, 1045, 915.

NMR(60 MC, $CDCl_3$) δ:0.92(3H), 1.25(32H), 2.72(3H), 3.05(2H), 3.37(3H), 3.60(1H), 3.89(2H), 4.28(2H), 4.63(3H), 5.00(1H), 8.0–8.5(2H), 9.17–9.47(2H).

EXAMPLE 122

3-Octadecylcarbamoyl-2-methyl-1-(pyridin-2-yl)carbamoylglycerol

α-Picolinic acid (1.23 g: 10 mmole), diphenylphosphorylazide (3.03 g: 11 mmole), triethylamine (1.2 g) and toluene (20 ml) were treated in the same manner as described in Example 118 to give 2.7 g (yield 83%) of colorless crystals.

TLC [silica gel; $CHCl_3$, MeOH (19:1)] Rf=0.51 single spot

NMR (60MC, $CDCl_3$) δ:0.92(3H), 1.25(32H), 3.13(2H), 3.47(3H), 3.70(1H), 4.20(2H), 4.30–4.73(1H), 6.90(1H), 7.65(1H), 7.90(1H), 8.33(1H), 8.83(1H).

EXAMPLE 123

N-[2-[3-(Octadecylcarbamoyloxy-2-methoxypropoxy)carbonylamino]ethyl]-N-ethoxycarbonylmethyl-N,N-dimethylammonium chloride In 2 ml of ethyl monochloroacetate was dissolved 1.03 g (2 mmole) of the dimethyl derivative as obtained in Example 9, and the solution was allowed to stand at room temperature for 16 hours, followed by concentration under reduced pressure. The residue was recrystallized when hot from 6 ml of ethyl acetate to give 1.2 g (yield 94.0%) of colorless needles.

TLC [silica gel; $CHCl_3$, MeOH, $H_2O$ (65:25:4)] Rf=0.37.

IR (film) cm$^{-1}$: 3350, 2920, 2850, 1775, 1710, 1520, 1470, 1450, 1260, 1150, 1030.

NMR (60MC, $CDCl_3$) δ:0.83(6H), 1.27(32H), 3.13(2H), 3.60(6H), 4.13(6H), 5.13(1H), 7.33(1H), 3.2–4.3(5H).

EXAMPLE 124

N-[2-[(3-Octadecylcarbamoyloxy-2-methoxypropoxy)carbonylamino]ethyl]-N-carboxylatomethyl-N,N-dimethylammonium In 1.56 ml of t-butanol was dissolved 300 mg of the ester as obtained in Example 123, and 26 mg of powdered potassium hydroxide was added to the solution. The reaction solution was stirred at room temperature for 1 hour and neutralized with conc. hydrochloric acid. 10 ml of ice-water and 10 ml of dichloromethane were added to the reaction solution, followed by stirring. The organic layer was separated, dried over sodium sulfate and concentrated to dryness under reduced pressure. The residue was purified by silica gel (5 g) [eluent: chloroform-methanol-water (65:25:4)] to give 216 mg (yield 80.0%) of a colorless powder.

TLC [silica gel; $CHCl_3$, MeOH, $H_2O$ (65:25:4)] Rf=0.31 single spot.

IR (KBr) cm$^{-1}$: 3450, 2930, 2850, 1710, 1640, 1540, 1470, 1400, 1270, 1140, 1050.

NMR (60MC, $CDCl_3$) δ:0.83(3H), 1.25(32H), 3.10(2H), 3.32(3H), 3.40(6H), 4.08(4H), 5.30(1H), 7.60(1H), 2.9–4.0(5H).

EXAMPLE 125

1-(3-Trityloxy-2-methoxypropyl)uracil

In 20 ml of dimethylformamide was suspended 2.24 g (20 mmole) of uracil and 5.03 g (10 mmole) of 3-trityl-2-methylglycerol in the presence of 4.24 g of sodium carbonate, and the suspension was stirred at 105° C. for 16 hours. The reaction solution was concentrated to dryness under reduced pressure, and 100 ml of water, and 100 ml of chloroform were added to the residue. After the aqueous layer was adjusted to pH 7.0 with acetic acid and shaken vigorously, the organic layer was separated, dried over sodium sulfate and concentrated to dryness under reduced pressure. The residue was purified by silica gel (30 g) [eluent: chloroform-ethyl acetate-n-hexane (4:1:3)] to give 2.67 g (yield 60.5%) of a colorless powder.

TLC [silica gel; $CHCl_3$, MeOH (19:1)] Rf=0.44.

EXAMPLE 126

1-(3-Trityloxy-2-methoxypropyl)-3-(pyridin-2-yl)methyluracil

In 6 ml of dimethylsulfoxide were dissolved 1.2 g (2.72 mmole) of the uracil derivative as obtained in Example 125 and 1.04 g (8.15 mmole) of 2-chloromethylpyridine hydrochloride in the presence of 1.12 g of powdered potassium hydroxide, and the reaction solution was stirred at 50° C. for 1 hour and poured into 60 ml of water. The mixture was adjusted to pH 7.0 and extracted with 60 ml of ether. The ether layer was dried over sodium sulfate and concentrated to dryness under reduced pressure. The residue was purified by silica gel (10 g) [eluent: ethyl acetate-n-hexane (2:1)] to give 1.4 g (yield 96.5%) of a colorless solid.

TLC [silica gel; n-hexane-EtOAc (1:2)] Rf=0.14.

NMR (60MC, $CDCl_3$) δ:3.22(1H), 3.28(3H), 3.60(2H), 4.05(2H), 5.23(2H), 7.0–8.0(18H), 8.27(1H).

EXAMPLE 127

1-(3-Hydroxy-2-methoxypropyl)-3-(pyridin-2-yl)methyluracil

In a mixture of 40 ml of methanol, 5 ml of water and 3 ml of conc. hydrochloric acid was dissolved 1.4 g (2.62 mmole) of the trityl derivative as obtained in Example 126, and the solution was stirred at room temperature for 1 hour. After the solution was cooled to 4° C. and the crystals separated was removed by filtration, the filtrate was neutralized with 1 N sodium hydroxide and concentrated to dryness under reduced pressure. The residue was dissolved in a mixture of 19 ml of chloroform and 1 ml of methanol. The insoluble material was removed and the solution was concentrated to dryness under reduced pressure. The residue was purified by silica gel (10 g) [eluent: chloroform, methanol (19:1)] to give 729 mg (yield 100%) of a colorless solid material.

TLC [silica gel; CHCl$_3$, MeOH (19:1)] Rf=0.25.

NMR (60MC, CDCl$_3$) δ:2.85(1H), 3.88(3H), 3.60(3H), 3.93(2H), 5.27(2H), 5.73(1H), 7.23(3H), 7.60(1H), 8.30(1H).

EXAMPLE 128

1-(3-Octadecylcarbamoyloxy-2-methoxy)propyl-3-(pyridin-2-yl)methyluracil

In 1 ml of pyridine were dissolved 729 mg (2.65 mmole) of the hydroxy derivative as obtained in Example 127 and 0.78 g (2.65 mmole) of octadecyl isocyanate, the reaction solution was heated at 105° C. for 16 hours, followed by concentration to dryness under reduced pressure. The residue was purified by silica gel (15 g) [eluent: chloroform, methanol (49:1)] to give 1.2 g (yield 77.2%) of a colorless powder.

TLC [silica gel; CHCl$_3$, MeOH (19:1)] Rf=0.42.

NMR (60MC, CDCl$_3$) δ:0.87(3H), 1.23(32H), 3.38(3H), 3.63(1H), 4.11(2H), 4.15(2H), 5.08(1H), 5.27(2H), 5.72(1H), 7.17(2H), 7.23(1H), 7.58(1H), 8.45(1H).

EXAMPLE 129

2-[1-(3-Octadecylcarbamoyloxy-2-methoxypropyl)uracil-3-yl]methyl-1-methylpyridinium iodide In a mixture of 0.5 ml of dichloromethane and 338.6 mg (2.386 mmole) of methyl iodide was dissolved 700 mg (1.19 mmole) of the pyridine derivative as obtained in Example 128, and the reaction solution was allowed to stand at room temperature overnight, followed by concentration to dryness under reduced pressure. The residue was recrystallized from a mixture of 1.5 ml of dichloromethane and 15 ml of n-hexane to give 880 mg (yield 100%) of a colorless powder.

TLC [silica gel; CHCl$_3$ MeOH, H$_2$O (65:25:4)] Rf=0.33.

IR (film) cm$^{-1}$: 3300, 2940, 2850, 1710, 1660, 1515, 1455, 1400, 1370, 1250.

NMR (60MC, CDCl$_3$) δ:0.90(3H), 1.25(32H), 6.48(2H), 3.40(3H), 3.70(1H), 4.15(4H), 4.72(3H), 5.15(1H), 5.25(2H), 5.80(1H), 7.50(1H), 7.97(2H), 8.43(1H), 9.35(1H).

Elemental Analysis, for C$_{34}$H$_{57}$N$_4$O$_5$I.2H$_2$O (764.79): Calcd.: C, 53.40; H, 8.04; N, 7.33. Found: C, 53.40; H, 7.89; N, 7.43.

EXAMPLE 130

1-(3-Trityloxy-2-methoxypropyl)-3-(2-benzyloxyethyl)uracil

In 6 ml of dimethylsulfoxide were dissolved 1.36 g (3.08 mmole) of the uracil derivative as obtained in Example 125 and 2.83 g (9.24 mmole) of 2-benzyl-1-tosylethyleneglycol, and 690 mg of powdered potassium hydroxide was added to the solution, followed by stirring at 50° C. for 2 hours. The reaction solution was poured into 60 ml of ice-water and the resulting mixture was adjusted to pH 7.0 with acetic acid and extracted with 100 ml of ether. The ether layer was dried over sodium sulfate and concentrated to dryness under reduced pressure. The residue was purified by silica gel (15 g) [eluent: n-hexane, ethyl acetate (2:1)] to give 1.78 g (yield 100%) of a viscous material.

TLC [silica gel; n-hexane, EtOAc (1:1)] Rf=0.50 single spot

NMR (60MC, CDCl$_3$) δ:3.25(3H), 3.23(1H), 3.52(2H), 3.70(2H), 4.13(4H), 4.50(2H), 5.53(1H), 6.7–8.0(21H).

EXAMPLE 131

1-(3-Hydroxy-2-methoxypropyl)-3-(2-benzyloxyethyl)uracil

In a mixture of 40 ml of methanol, 50 ml of water, 10 ml of dichloromethane and 3 ml of conc. hydrochloric acid was dissolved 1.78 g (3.08 mmole) of the trityl derivative as obtained in Example 130, and the reaction solution was stirred at room temperature for 1.5 hours, neutralized with sodium hydrogencarbonate and concentrated to dryness under reduced pressure. The residue was purified by silica gel (15 g) [eluent: chloroform, methanol (19:1)] to give 973 mg (yield 94.5%) of a colorless viscous material.

TLC [silica gel; CHCl$_3$, MeOH (19:1)] Rf=0.33.

NMR (60MC, CDCl$_3$) δ:2.75(1H), 3.33(3H), 3.53(2H), 3.70(2H), 3.83(2H), 4.22(2H), 4.50(2H), 5.65(1H), 7:13(1H), 7.24(5H)

EXAMPLE 132

1-(3-Octadecylcarbamoyloxy-2-methoxypropyl)-3-(2-benzyloxyethyl)uracil

In 1 ml of pyridine were dissolved 970 mg (2.9 mmole) of the hydroxy derivative as obtained in Example 131 and 857 mg (2.9 mmole) of octadecyl isocyanate, and the reaction solution was heated at 120° C. for 16 hours, followed by concentration to dryness under reduced pressure. The residue was purified by silica gel (17 g) [eluent: chloroform, ethyl acetate, n-hexane (48:2:50)] to give 1.59 g (yield 87.0%) of a colorless solid.

TLC [silica gel; CHCl$_3$, MeOH (19:1)] Rf=0.74 single spot.

NMR (60MC, CDCl$_3$) δ:0.83(3H), 1.22(32H), 3.17(2H), 3.30(3H), 3.62(1H), 3.73(2H), 4.0–4.4(6H), 4.55(2H), 4.97(1H), 5.67(1H), 7.17(1H), 7.27(5H).

EXAMPLE 133

1-(3-Octadecylcarbamoyloxy-2-methoxypropyl)-3-(2-hydroxyethyl)uracil

In 50 ml of 70% acetic acid was dissolved 1.59 g (2.5 mmole) of the benzyl derivative as obtained in Example 132, and the solution was shaken for 16 hours in the presence of 300 mg of palladium carbon under a hydrogen gas stream. The insoluble material was filtered off, and the filtrate was concentrated to dryness under reduced pressure. The residue was recrystallized from 10 ml of methanol to give 1.16 g (yield 85.2%) of colorless crystals.

TLC [silica gel; CHCl$_3$, MeOH (19:1)] Rf=0.28 single spot.

NMR (60MC, CDCl$_3$) δ:0.92(3H), 1.25(32H), 2.30(1H), 3.13(2H), 3.38(3H), 3.63(3H), 3.87(2H), 4.15(4H), 4.97(1H), 5.68(1H), 7.20(1H).

EXAMPLE 134

1-(3-Octadecylcarbamoyloxy-2-methoxypropyl)-3-(2-toluenesulfonyloxyethyl)uracil

In 3 ml of dichloromethane were dissolved 1.16 g (2.15 mmole) of the hydroxy derivative as obtained in Example 133 and 574 mg (3.01 mmole) of tosyl chloride, and 404 mg of triethylamine was added to the solution, followed by stirring for 3 hours. To the reaction solution were added 20 ml of dichloromethane and 20 ml of ice-water, and the mixture was shaken vigorously. The organic layer was separated, dried over sodium sulfate and concentrated to dryness under reduced pressure. The residue was purified by silica gel (13 g) [eluent: n-hexane, ethyl acetate, chloroform, methanol (50:50:98:2)] to give 1.35 g of a mixture of the objective tosylate derivative and the chloride.

TLC [silica gel; n-hexane, EtOAc (1:1)] Rf=0.12, 0.26 two spots.

EXAMPLE 135

N-[2-{1-(3-Octadecylcarbamoyloxy-2-methoxy)-propyluracil-3-yl}ethyl]thiazolium chloride In 3 ml of thiazole was dissolved 1.08 g of the mixture as obtained in Example 134, and the solution was heated at 100° C. for 3 days, followed by concentration to dryness under reduced pressure. The residue was dissolved in 50 ml of 70% methanol and the solution was passed through a column (25 ml) of IRA-410 (Cl$^-$ type) and washed with a small amount of 70% methanol. The effluent and washing were combined and concentrated to dryness under reduced pressure. The residue was purified by silica gel (2.5 g) [eluent: chloroform, methanol, water (65:25:4)] to give 625 mg (yield 56.5%) of a colorless solid.

TLC [silica gel; CHCl$_3$, MeOH, H$_2$O (65:25:4)] Rf=0.37 single spot.

IR (film) cm$^{-1}$: 3350, 2920, 2850, 1710, 1660, 1540, 1460, 1400, 1250, 1150, 1050.

NMR (60MC, CDCl$_3$) δ:0.93(3H), 1.23(32H), 3.10(2H), 3.38(3H), 3.63(1H), 4.10(4H), 4.57(2H), 5.20(2H), 5.60(1H), 5.77(1H), 7.43(1H), 8.30(1H), 8.85(1H), 10.93(1H).

EXAMPLE 136

N-[2-{1-(3-Octadecylcarbamoyloxy-2-methoxypropyl)uracil-3-yl}ethyl]-N,N,N-trimethylammonium chloride In 5 ml of 20% trimethylamine-toluene (v/v) was dissolved 135 mg of the mixture as obtained in Example 134, and the reaction solution was allowed to stand at room temperature for 4 hours and concentrated to dryness under reduced pressure. The residue was dissolved in 10 ml of 70% methanol and the solution was passed through 7 ml of IRA-410 (Cl$^-$ type). The effluent and washing were combined and concentrated to dryness under reduced pressure. The residue was purified by silica gel (2.5 g) [eluent: chloroform, methanol, water (65:25:4)] to give 83 mg (yield 62.5%) of a colorless solid.

TLC [silica gel; CHCl$_3$, MeOH, H$_2$O (65:25:4)] Rf=0.27 single spot.

IR (film) cm$^{-1}$: 3350, 2920, 2850, 1710, 1660, 1530, 1460, 1380, 1250, 1140, 1055, 930.

NMR (60MC, CDCl$_3$) δ:0.89(3H), 1.23(32H), 3.18(2H), 3.38(3H), 3.53(9H), 3.72(1H), 3.90(2H), 4.12(4H), 4.40(2H), 5.57(1H), 5.77(1H), 7.43(1H).

EXAMPLE 137

N-[2-[1-(3-Octadecylcarbamoyloxy-2-methoxypropyl)uracil-3-yl]ethyl-N-methylpyrrolidinium chloride In 3 ml of N-methylpyrrolidine was dissolved 135 mg of the mixture as obtained in Example 134, and the reaction solution was heated at 100° C. for 2 days, and treated in the same manner as described in Example 136 to give 56 mg (yield 40.5%) of a colorless solid.

TLC [silica gel; CHCl$_3$, MeOH, H$_2$O (65:25:4)] Rf=0.35 single spot.

IR (film) cm$^{-1}$: 3350, 2920, 2850, 2700, 2620, 1710, 1660, 1530, 1460, 1390, 1250, 1100, 1040.

NMR (60MC, CDCl$_3$) δ:0.90(3H), 1.23(32H), 2.27(4H), 3.07(2H), 3.37(3H), 3.40(3H), 3.62(1H), 3.75(4H), 4.10(2H), 4.33(4H), 5.58(1H), 5.77(1H), 7.43(1H)

EXAMPLE 138

2-(3-Octadecylcarbamoyloxy-2-methoxypropoxycarbonyl)aminomethylthiazole

In 2 ml of toluene were dissolved 2.33 g (4.47 mmole) of 3-octadecylcarbamoyl-2-methyl-1-phenoxycarbonyl-glycerol synthesized in the same manner as described in Example 9, 0.77 g (6.13 mmole) of 2-aminomethylthiazole and 2 ml of triethylamine, and the reaction solution was allowed to stand at room temperature for 1 day and concentrated to dryness under reduced pressure. The residue was purified by silica gel (25 g) [eluent: n-hexane, ethyl acetate (1:1)] to give 1.35 g (yield 55.7%) of a pale yellow powder.

TLC [silica gel; n-hexane, EtOAc (1:1)] Rf=0.37 single spot.

NMR (60MC, CDCl$_3$) δ:0.90(3H), 1.25(32H), 3.13(2H), 3.47(3H), 3.62(1H), 4.17(2H), 4.67(2H), 4.80(1H), 5.63(1H), 7.27(1H), 7.67(1H).

EXAMPLE 139

2-[N-Acetyl-N-(3-octadecylcarbamoyloxy-2-methoxypropoxycarbonyl)aminomethyl]thiazole In 0.5 ml of toluene were dissolved 108 mg (0.2 mmole) of the thiazole derivative as obtained in Example 138, 122 mg (1.0 mmole) of dimethylaminopyridine and 102 mg (1.0 mmole) of acetic anhydride, and the reaction solution was heated at 80° C. for 4 hours and concentrated to dryness under reduced pressure. The residue was purified by silica gel (3 g) [eluent: chloroform, methanol (39:1)] and further silica gel (3 g) [eluent: n-hexane, ethyl acetate (1:1)] to give 110 mg (yield 78.1%) of a colorless solid.

TLC [silica gel; n-hexane, EtOAc (1:2)] Rf=0.43 single spot.

IR (film) cm$^{-1}$: 3350, 2930, 2850, 1745, 1715, 1525, 1470, 1430, 1375, 1345, 1210, 1145, 1080, 920.

NMR (60MC, CDCl$_3$) δ:0.92(3H), 1.23(32H), 2.6(3H), 3.08(2H), 3.37(3H), 3.57(1H), 4.10(2H), 4.27(2H), 4.90(1H), 5.27(2H), 7.23(1H), 7.67(1H).

EXAMPLE 140

2-[N-(3-Octadecylcarbamoyloxy-2-methoxypropoxycarbonyl)amino]methyl-3-methylthiazolium iodide In 1.5 ml of methyl iodide was dissolved 100 mg (0.185 mmole) of the thiazole derivative as obtained in Example 138, and the reaction solution was heated at 70° C. for 8 hours and concentrated to dryness under reduced pressure to give 124 mg (yield 100%) of a pale yellow solid.

TLC [silica gel; CHCl$_3$, MeOH, H$_2$O (65:25:4)] Rf=0.35 single spot.

IR (film) cm$^{-1}$: 3340, 2930, 2850, 1700, 1520, 1470, 1250, 1140, 1050.

NMR (60MC, CDCl$_3$) δ:0.88(3H), 1.25(32H), 3.15(2H), 3.45(3H), 3.65(1H), 4.13(2H), 4.23(2H), 5.08(3H), 8.27(1H), 8.45(1H).

EXAMPLE 141

2-[N-(3-Octadecylcarbamoyloxy-2-methoxypropoxycarbonyl)amino]methyl-3-ethylthiazolium iodide In 1.0 ml of ethyl iodide was dissolved 100 mg (0.185 mmole) of the thiazole derivative as obtained in Example 138, and the reaction solution was heated at 80° C. overnight and concentrated to dryness under reduced pressure. The residue was purified by silica gel (2 g) [eluent: CHCl$_3$→CHCl$_3$, MeOH (19:1)] to give 91 mg (yield 70.5%) of a pale yellow solid.

TLC [silica gel; CHCl$_3$, MeOH, H$_2$O (65:25:4)] Rf=0.66 single spot.

IR (film) cm$^{-1}$: 3320, 2920, 2850, 1720, 1520, 1465, 1240, 1140, 1050, 910.

NMR (60MC, CDCl$_3$) δ:0.88(3H), 1.27(32H), 1.67(3H), 3.13(2H), 3.45(3H), 3.63(1H), 4.13(2H), 4.25(2H), 4.73(2H), 4.98(1H), 5.10(2H), 7.33(1H), 8.25(1H), 8.45(1H).

EXAMPLE 142

2-[N-Acetyl-N-(3-octadecylcarbamoyloxy-2-methoxypropoxycarbonyl)amino]methyl-3-methylthiazolium iodide In 1.5 ml of methyl iodide was dissolved 100 mg (0.185 mmole) of the acetate derivative as obtained in Example 139, and the reaction solution was heated at 50° C. for 16 hours and concentrated to dryness under reduced pressure. The residue was purified by silica gel (2 g) [eluent: CHCl$_3$, MeOH, H$_2$O (65:25:4)] to give 116 mg (yield 100%) of a pale yellow powder.

TLC [silica gel: CHCl$_3$, MeOH, H$_2$O (65:25:4)] Rf=0.25 single spot.

IR (film) cm$^{-1}$: 3400, 2930, 2850, 1700, 1560, 1530, 1470, 1375, 1330, 1250, 1200, 1140, 1075.

NMR (60MC, CDCl$_3$) δ:0.92(3H), 1.25(32H), 2.62(3H), 3.08(2H), 3.48(3H), 3.80(1H), 4.17(2H), 4.45(2H), 4.52(2H), 5.33(1H), 5.59(2H), 8.43(1H), 8.58(1H).

EXAMPLE 143

2-[N-Acetyl-N-(3-octadecylcarbamoyloxy-2-methoxypropoxycarbonyl)amino]methyl-3-ethylthiazolium iodide In 1.0 ml of ethyl iodide was dissolved 117 mg (0.2 mmole) of the acetate derivative as obtained in Example 139, and the reaction solution was heated at 90° C. for 5 hours and concentrated to dryness under reduced pressure. The residue was purified by silica gel (2 g) [eluent: CHCl$_3$→CHCl$_3$, MeOH (19:1)] to give 116 mg (yield 50.7%) of a pale yellow powder.

TLC [silica gel; CHCl$_3$, MeOH, H$_2$O (65:25:4)] Rf=0.71 single spot.

IR (film) cm$^{-1}$: 3300, 2920, 2850, 1750, 1700, 1525, 1465, 1370, 1340, 1240, 1205, 1140, 1105, 1070, 990.

NMR (60MC, CDCl$_3$) δ:0.83(3H), 1.23(32H), 1.69(3H), 2.62(3H), 3.13(2H), 3.47(3H), 3.80(1H), 4.17(2H), 4.46(2H), 4.92(2H), 5.10(1H), 5.63(2H), 8.43(1H), 8.67(1H).

EXAMPLE 144

2-[N-Acetyl-N-(3-octadecylcarbamoyloxy-2-methoxypropoxycarbonyl)amino]methyl-3-propylthiazolium iodide In 1.0 ml of propyl iodide was dissolved 117 mg (0.2 mmole) of the acetate derivative as obtained in Example 139, and the reaction solution was heated at 90° C. for 5 hours and concentrated to dryness under reduced pressure. The residue was purified by silica gel (2 g) [eluent: CHCl$_3$→CHCl$_3$, MeOH (19:1)] to give 116 mg (yield 50.7%) of a pale yellow powder.

TLC [silica gel: CHCl$_3$, MeOH, H$_2$O (65:25:4)] Rf=0.73 single spot.

IR (film) cm$^{-1}$: 3350, 2920, 2850, 1750, 1700, 1535, 1470, 1375, 1340, 1240, 1205, 1150, 1100, 1070, 990.

NMR (60MC, CDCl$_3$) δ:0.88(3H), 1.08(3H), 1.23(32H), 2.16(2H), 2.62(3H), 3.15(2H), 3.45(3H), 3.83(1H), 5.62(2H), 8.43(1H), 8.67(1H).

EXAMPLE 145

2-[N-Acetyl-N-(3-octadecylcarbamoyloxy-2-methoxypropoxycarbonyl)amino]methyl-3-butylthiazolium iodide In 1.0 ml of butyl iodide was dissolved 117 mg (0.2 mmole) of the acetate derivative as obtained in Example 139, and the reaction solution was heated at 90° C. for 5 hours and concentrated to dryness under reduced pressure. The residue was purified by silica gel (2 g) [eluent: CHCl$_3$→CHCl$_3$, MeOH (19:1)] and further silica gel (2 g) [eluent: acetone, ethyl acetate (1:1)] to give 47 mg (yield 30.5%) of a pale brown solid.

TLC [silica gel; CHCl$_3$MeOH, H$_2$O (65:25:4)] Rf=0.74 single spot.

IR (film) cm$^{-1}$: 3340, 2925, 2855, 1755, 1700, 1535, 1470, 1430, 1375, 1340, 1240, 1205, 1150, 1110, 1070, 1040, 985.

NMR (60MC, CDCl$_3$) δ:0.88(3H), 1.00(3H), 1.25(32H), 2.00(4H), 2.65(3H), 3.10(2H), 3.45(3H), 3.78(1H), 5.12(1H), 5.58(2H), 8.42(1H), 8.62(1H).

EXAMPLE 146

4-(3-Octadecylcarbamoyloxy-2-methoxypropoxycarbonyl)aminomethylthiazole

In 5 ml of dichloromethane were dissolved 2.60 g (5.0 mmole) of 3-octadecylcarbamoyl-2-methyl-1-phenoxycarbonylglycerol synthesized in the same manner as described in Example 9, 0.57 g (5.00 mmole) of 4-aminomethylthiazole and 1 ml of triethylamine, and the reaction solution was heated at 50° C. overnight and concentrated to dryness under reduced pressure. The residue was purified by silica gel (25 g) [eluent: n-hexane, ethyl acetate (1:1)] to give 440 mg (yield 16.0%) of a pale yellow powder.

TLC [silica gel; n-hexane, EtOAc (1:1)] Rf=0.51 single spot.

EXAMPLE 147

4-[N-Acetyl-N-(3-octadecylcarbamoyloxy-2-methoxypropoxycarbonyl)amino]methylthiazole In 1.0 ml of toluene were dissolved 162 mg (0.3 mmole) of the thiazole derivative as obtained in Example 146, 244 mg (2.0 mmole) of dimethylaminopyridine and 204 mg (2.0 mmole) of acetic anhydride, and the reaction solution was heated at 110° C. overnight and concentrated to dryness under reduced pressure. The residue was purified by silica gel (2 g) [eluent: chloroform] and further silica gel (2 g) [eluent: n-hexane, ethyl acetate (1:1)] to give 84 mg (yield 48.0%) of a colorless solid.

TLC [silica gel; n-hexane, EtOAc (1:2)] Rf=0.63 single spot.

IR (film) cm$^{-1}$: 3350, 2920, 2850, 1740, 1705, 1535, 1465, 1435, 1370, 1350, 1200, 1140, 1080, 980, 950.

NMR (60MC, CDCl$_3$) δ:0.88(3H), 1.25(32H), 2.57(3H), 3.18(2H), 3.38(3H), 3.67(1H), 4.12(2H), 4.24(2H), 4.92(1H), 5.14(2H), 7.17(1H), 8.73(1H).

EXAMPLE 148

4-[N-Acetyl-N-(3-octadecylcarbamoyloxy-2-methoxypropoxycarbonyl)amino]methyl-3-methylthiazolium iodide In 0.5 ml of methyl iodide was dissolved 4.5 mg of the acetate as obtained in Example 147, and the reaction solution was heated at 60° C. for 16 hours and concentrated to dryness under reduced pressure. The residue was purified by silica gel (0.5 g) [eluent: CHCl$_3$, MeOH (65:25)] to give 1.85 mg of a pale yellow powder.

TLC [silica gel; CHCl$_3$, MeOH, H$_2$O (65:25:4)] Rf=0.69 single spot.

EXAMPLE 149

4-[N-Acetyl-N-(3-octadecylcarbamoyloxy-2-methoxypropoxycarbonyl)amino]methyl-3-ethylthiazolium iodide In 1.0 ml of ethyl iodide was dissolved 79.5 mg (0.136 mmole) of the acetate derivative as obtained in Example 147, and the reaction solution was heated at 90° C. overnight and concentrated under reduced pressure. The residue was purified by silica gel (1.7 g) [eluent: CHCl$_3$→CHCl$_3$, MeOH (19:1)] to give 44 mg (yield 43.7%) of a pale yellow solid.

TLC [silica gel; CHCl$_3$, MeOH, H$_2$O (65:25:4)] Rf=0.72 single spot.

IR (film) cm$^{-1}$: 3350, 2925, 2855, 1750, 1705, 1525, 1465, 1370, 1335, 1240, 1205, 1140, 1105, 1070, 1040, 995, 940.

NMR (60MC, CDCl$_3$) δ:0.87(3H), 1.23(32H), 1.72(3H), 2.60(3H), 3.08(2H), 3.45(3H), 3.79(1H), 4.14(2H), 4.42(2H), 4.87(2H), 5.07(1H), 5.20(2H), 8.25(1H), 10.80(1H).

EXAMPLE 150

4-Methyl-5-(3-octadecylcarbamoyloxy-2-methoxypropoxycarbonylaminoethylthiazole

In 1 ml of toluene were dissolved 439 mg (1.26 mmole) of 3-octadecylcarbamoyl-2-methyl-1-phenoxycarbonylglycerol synthesized in the same manner as described in Example 9, 179.5 mg (1.26 mmole) of 4-methyl-5-aminoethylthiazole and 1 ml of triethylamine, and the reaction solution was heated at 50° C. for 4 hours and concentrated to dryness under reduced pressure. The residue was purified by silica gel (5 g) [eluent: n-hexane, ethyl acetate (1:1)] to give 345 mg (yield 73.6%) of a pale yellow powder.

TLC [silica gel; n-hexane, EtOAc (1:1)] Rf=0.21 single spot.

NMR (60MC, CDCl$_3$) δ:0.80(3H), 1.25(32H), 2.46(3H), 2.52(3H), 3.07(2H), 3.13(2H), 3.47(3H), 3.63(1H), 4.16(2H), 4.23(1H), 4.97(1H), 8.50(1H).

EXAMPLE 151

3,4-Dimethyl-5-[2-(3-octadecylcarbamoyloxy-2-methoxypropoxycarbonyl)amino]ethylthiazolium iodide In 1.5 ml of methyl iodide was dissolved 100 mg (0.18 mmole) of the thiazole derivative as obtained in Example 150, and the reaction solution was heated at 70° C. for 8 hours and concentrated to dryness under reduced pressure to give 128 mg (yield 100%) of a pale yellow solid.

TLC [silica gel; CHCl$_3$, MeOH, H$_2$O (65:25:4)] Rf=0.39 single spot.

NMR (60MC, CDCl$_3$) δ:0.87(3H), 1.27(32H), 2.52(3H), 3.18(4H), 3.45(3H), 3.58(3H), 4.17(4H), 4.27(3H), 5.06(1H), 6.27(1H), 10.45(1H).

EXAMPLE 152

4-Methyl-5-[N-acetyl-N-(3-octadecylcarbamoyloxy-2-methoxypropoxycarbonyl)amino]ethylthiazole In 1 ml of toluene were dissolved 190 mg (0.341 mmole) of the thiazole derivative as obtained in Example 150, 244 mg (2.0 mmole) of dimethylaminopyridine and 204 mg (2.0 mmole) of acetic anhydride, and the reaction solution was heated at 100° C. for 16 hours and concentrated to dryness under reduced pressure. The residue was purified by silica gel (2 g) [eluent: chloroform, methanol (39:1)] and further silica gel (2 g) [eluent: n-hexane, ethyl acetate (1:1)] to give 20 mg (yield 9.8%) of a colorless oil.

TLC [silica gel; n-hexane, EtOAc (1:1)] Rf=0.21 single spot.

NMR(60 MC, CDCl$_3$) δ:0.80(3H), 1.25(32H), 2.46(3H), 2.52(3H), 3.07(2H), 3.13(2H), 3.47(3H), 3.63(1H), 4.16(2H), 4.23(1H), 4.97(1H), 8.50(1H).

EXAMPLE 153

3,4-Dimethyl-5-[N-acetyl-N-(3-octadecylcarbamoyloxy-2-methoxypropoxycarbonyl)amino]ethylthiazolium iodide In 1 ml of methyl iodide was dissolved 20 mg (0.033 mmole) of the acetate derivative as obtained in Example 152, and the reaction solution was allowed to stand at room temperature for 16 hours and concentrated to dryness under reduced pressure to give 25 mg (yield 100%) of the objective compound.

TLC[silica gel; CHCl$_3$, MeOH, H$_2$O(65:25:4)] Rf=0.42 single spot

IR(KBr)cm$^{-1}$: 3330, 2920, 2850, 1730, 1700, 1520, 1470, 1370, 1325, 1270, 1250, 1200, 1150, 1100, 1060, 1040, 975, 920.

NMR(60 MC, CDCl$_3$) δ:0.87(3H), 1.23(32H), 2.52(3H), 2.59(3H), 3.72(1H), 3.97(2H), 4.22(4H), 4.40(3H), 5.10(1H), 10.88(1H).

EXAMPLE 154

1-Octadecylcarbamoyl-2-methyl-3-(4-methyl-piperazino)carbonylglycerol

In 20 ml of dichloromethane was dissolved 2.01 g of 3-octadecylcarbamoyl-2-methylglycerol, and 0.941 g of phenyl chloroformate and 0.47 g of pyridine was added to the solution, followed by stirring at room temperature for 30 minutes. The reaction solution was treated with 40 ml of chloroform, washed with water and aqueous sodium hydrogencarbonate solution, dried and concentrated to give the carbonate ester. 2 ml of N-methylpiperazine was added to the ester and the mixture was heated at 60° C. for 1 hour. After cooling, the reaction mixture was purified by silica gel chromatography [eluent: ethyl acetate:methanol (10:1)] to give 2.10 g of the objective compound as a colorless solid.

IR(KBr, cm$^{-1}$) 3340, 2930, 2850, 2800, 1748, 1698, 1536, 1470, 1450, 1300, 1260, 1240, 1150.

NMR(90 MHz, CDCl$_3$) $\delta$:0.87(3H, t), 1.25, 1.70(32H, m), 2.28(3H, s), 2.25–2.5(4H), 3.15(2H, q), 3.44(3H, s), 3.5–3.7(5H, m), 5.18(4H, m), 4.72(1H, m).

TLC:Rf=0.24 [AcOEt—MeOH(10:1)].

EXAMPLE 155

4-(3-Octadecylcarbamoyloxy-2-methoxypropoxycarbonyl)-1,1-dimethylpiperazinium iodide In 20 ml of ether was dissolved 1.80 g of the N-methyl derivative as obtained in Example 154, and 2.86 g of methyl iodide was added to the solution, followed by stirring at room temperature for 20 hours. The reaction solution was concentrated to dryness to give 2.26 g of the objective compound as a colorless powder.

EXAMPLE 156

4-(3-Octadecylcarbamoyloxy-2-methoxypropoxycarbonyl)-1,1-dimethylpiperazinium chloride The iodide derivative (2.0 g) as obtained in Example 155 was treated with Amberlite IRA-410 (Cl$^-$ type) ion exchange resin to conversion of an ion. The resulting chloride derivative was purified by silica gel chromatography [eluent: chloroform-methanol-water (65:25:4)] to give 1.517 g of the objective compound as a colorless powder.

IR(KBr, cm$^{-1}$) 3400, 2925, 2850, 1702, 1550, 1470, 1260, 1190, 1020.

NMR(90 MHz, CDCl$_3$) $\delta$:0.87(3H, t), 1.25(32H, s), 3.12(2H, q), 3.43(3H, s), 3.61(6H, s), 3.5–4.0(9H, m), 4.05–4.3(4H, m), 5.09(1H, br).

EXAMPLE 157

1-Octadecylcarbamoyl-2-methyl-3-(1-ethylpiperidin-3-yl)carbamoylglycerol

3-Amino-1-ethylpiperidine (1 ml) was added to 1.3 g of 1-octadecylcarbamoyl-2-methyl-3-phenoxycarbonylglycerol, and the reaction solution was heated at 60° C. for 1 hour and purified by silica gel chromatography [ethyl acetate-methanol (10:1)] to give 1.13 g of the objective compound as a milk-white solid.

NMR(90 MHz, CDCl$_3$) $\delta$:0.87(3H, t), 1.02(3H, t), 1.25(32H, m), 1.57(4H, m), 2.34(6H, m), 3.14(2H, m), 3.43(3H, s), 3.57(1H, m), 3.77(1H, m), 4.16(4H, m), 4.73(1H, br), 5.25(1H, br).

TLC:Rf=0.16[AcOEt—MeOH(10:1)].

EXAMPLE 158

3-(3-Octadecylcarbamoyloxy-2-methoxypropoxycarbonyl)amino-1-ethyl-1-methylpiperidinium iodide In 10 ml of ether was dissolved 200 mg of the N-ethyl derivative as obtained in Example 157, and 0.5 ml of methyl iodide was added to the solution. The reaction solution was stirred at room temperature for 2 days and concentrated to dryness to give 250 mg of the objective compound as a pale brown powder.

IR(KBr, cm$^{-1}$) 3460, 3330, 2925, 2852, 1702, 1530, 1472, 1260, 1140, 1060, 782, 730.

NMR(90 MHz, CDCl$_3$) $\delta$:0.87(3H, t), 1.25(32H, m), 1.45(3H, t), 2.10(4H, m), 3.13(2H, m), 4.18, 4.38(3H, s), 3.43(3H, s), 3.5–4.1(8H, m), 4.14(4H, m), 4.91(1H, br), 5.8(1H, br).

TLC:Rf=0.25[CHCl$_3$—MeOH=5:1].

EXAMPLE 159

1-Octadecylcarbamoyl-2-methyl-3-[N-acetyl-N-(1-ethylpiperidin-3-yl)]carbamoylglycerol In a mixture of 5 ml of pyridine and 2 ml of acetic anhydride was dissolved 600 mg of the compound as obtained in Example 157, and the reaction solution was refluxed for 18 hours and concentrated to dryness. The residue was purified by silica gel chromatography to give 125 mg of the objective compound as a pale brown solid.

IR(KBr, cm$^{-1}$) 3350, 2930, 2855, 1740, 1710, 1530, 1460, 1378, 1230, 1220, 1145, 780.

NMR(90 MHz, CDCl$_3$) $\delta$:0.87(3H, t), 1.03(3H, t), 1.25(32H, m), 1.5–2.1(4H, m), 2.25–3.0(6H, m), 2.40(3H, s), 3.14(2H, m), 3.45(3H, s), 3.64(1H, m), 4.25(4H, m), 4.60(1H, m), 5.10(1H, br).

TLC:Rf=0.19[AcOEt—MeOH (10:1)].

EXAMPLE 160

3-[N-Acetyl-N-(3-octadecylcarbamoyloxy-2-methoxypropoxycarbonyl]amino-1-ethyl-1-methylpiperidinium iodide In 5 ml of ether was dissolved 118 mg of the compound as obtained in Example 159, and 0.2 ml of methyl iodide was added to the solution. The reaction solution was stirred at room temperature for 3 days and concentrated to dryness to give 146 mg of the objective compound as a pale brown powder.

IR(KBr, cm$^{-1}$) 3420, 2925, 2852, 1738, 1700, 1535, 1470, 1372, 1325, 1240, 1180.

EXAMPLE 161

3-[N-Acetyl-N-(3-octadecylcarbamoyloxy-2-methoxypropoxycarbonyl)]amino-1-ethyl-1-methylpiperidinium chloride The iodide derivative (145 mg) as obtained in Example 160 was subjected to exchange of an ion by Amberlite IRA-410 ion exchange resin (Cl$^-$ type) to give 120 mg of the chloride derivative as a pale brown solid.

IR(KBr, cm$^{-1}$) 3400, 2925, 2850, 1735, 1698, 1538, 1470, 1372, 1325, 1240, 1178, 780, 725.

NMR(90 MHz, CDCl$_3$) $\delta$:0.87(3H, t), 1.25(32H, m), 1.70(3H, t), 2.02(4H, m), 2.44(3H, s), 3.12(2H, m), 3.3–3.65(4H, m), 3.45(3H, s), 3.65–4.1(4H, m), 4.19(2H, d), 4.40(2H, m), 4.9(1H, br), 5.15(1H, br).

TLC Rf=0.2[CHCl$_3$—MeOH (5:1)].

EXAMPLE 162

1-Octadecylcarbamoyl-2-methyl-3-trichloromethyloxycarbonylglycerol

A solution of 2.41 g of 1-octadecylcarbamoyl-2-methylglycerol and 0.96 ml of triethylamine in dichloromethane was added dropwise to a solution of 0.833 ml of diphosgene in 15 ml of dichloromethane under ice-cooling. The reaction solution was stirred at room temperature for 40 minutes and concentrated to dryness under reduced pressure to give the crude product of the carbonate derivative.

TLC Rf=0.45[n-hexane—AcOEt (3:1)].

EXAMPLE 163

1-Octadecylcarbamoyl-2-methyl-3-(2-benzyloxy-1-methoxycarbonylethyl)carbamoylglycerol A solution of 1.01 g (4.12 mmole) of O-benzyl-DL-serin methyl ester hydrochloride and 416 mg (4.12 mmole) of triethylamine in dichloromethane (2 ml) was added to a solution of 1.50 g of the crude carbonate derivative as obtained in Example 162 in dichloromethane (6 ml). The resulting solution was stirred at room temperature for 2 hours and the solvent was distilled off. The residue was purified by silica gel chromatography [eluent: n-hexane-ethyl acetate (2:1)] to give 1.28 g of the objective compound as a colorless solid.

IR(KBr, cm$^{-1}$) 3340, 2925, 2852, 1752, 1698, 1535, 1472, 1262, 1118, 1080, 790, 740, 702.

NMR(90 MHz, CDCl$_3$) δ:0.87(3H, t), 1.25(32H, m), 3.14(2H, m), 3.43(3H, s), 3.57(1H, m), 3.73(3H, s), 3.6–3.95(2H, m), 4.17(4H, m), 4.35–4.5(1H, m), 4.50(2H, s), 4.76(1H, br), 5.60(1H, br).

TLC Rf=0.5[n-hexane—AcOEt(1:1)].

EXAMPLE 164

1-Octadecylcarbamoyl-2-methyl-3-(2-hydroxy-1-methoxycarbonylethyl)carbamoylglycerol In a mixture of 14 ml of acetic acid, 4 ml of water and 2 ml of ethanol was dissolved 1.24 g of the benzyl derivative as obtained in Example 163, and catalytic reduction was conducted using palladium carbon as a catalyst under a hydrogen atmosphere. The catalyst was removed by filtration and the filtrate was concentrated to dryness. The residue was recrystallized from n-hexane to give 1.10 g of the objective compound as a colorless powder.

IR(KBr, cm$^{-1}$) 3330, 2930, 2855, 1745, 1700, 1550, 1540, 1475, 1265, 1080, 790, 730.

NMR(90 MHz, CDCl$_3$) δ:0.87(3H, t), 1.25(32H, m), 2.78(1H, br), 3.15(2H, m), 3.44(3H, s), 3.59(1H, m), 3.77(3H, s), 3.95(2H, m), 4.15(4H, m), 4.4(1H, m), 4.86(1H, br), 5.78(1H, br).

m.p. 59.5°–61° C.

EXAMPLE 165

1-Octadecylcarbamoyl-2-methyl-3-(1-methoxycarbonylvinyl)carbamoylglycerol

To 218.4 mg (0.4 mmole) of the alcohol derivative as obtained in Example 164 were added 183 mg (0.96 mmole) of tosyl chloride and 0.13 ml (0.96 mmole) of triethylamine, and the reaction solution was stirred at room temperature for 3 days. Chloroform was added to the solution and the resulting mixture was washed with water and aqueous sodium hydrogencarbonate solution, dried, concentrated, and purified by silica gel chromatography [eluent: n-hexane-ethyl acetate (3:1)] to give 175 mg of the objective compound as a colorless powder.

IR(KBr, cm$^{-1}$) 3335, 2970, 2925, 2851, 1735, 1710, 1692, 1640, 1540, 1472, 1450, 1350, 1270, 1250, 1218, 1140, 1095, 1070, 902, 810, 715.

NMR(90 MHz, CDCl$_3$) δ:0.87(3H, t), 1.25(32H, m), 3.15(2H, m), 3.46(3H, s), 3.61(1H, m), 3.83(3H, s), 4.21(4H, m), 4.70(1H, br), 5.79(1H, d), 6.27(1H, s).

TLC Rf=0.65[n-hexane—AcOEt (1:1)].

EXAMPLE 166

1-Octadecylcarbamoyl-2-methyl-3-(2-dimethylamino-1-methoxycarbonylethyl)carbamoylglycerol In 0.3 ml of toluene containing 60 mg of dimethylamine was dissolved 30 mg of the compound as obtained in Example 165, and the reaction solution was stirred at room temperature for 3 hours and concentrated to dryness under reduced pressure to give 32.5 mg of the objective compound as a colorless powder.

IR(KBr, cm$^{-1}$) 3325, 2925, 2850, 1750, 1695, 1550, 1470, 1275, 1260, 1150, 1075, 1035, 785, 725.

NMR(90 MHz, CDCl$_3$) δ:0.87(3H, t), 1.25(32H, m), 2.22(6H, s), 2.63(2H, d), 3.14(2H, m), 3.43(3H, s), 3.57(1H, m), 3.73(3H, s), 4.17(4H, m), 4.30(1H, t), 4.84(1H, br), 5.68(1H, br).

TLC Rf=0.58[AcOEt—Acetone (1:1)].

EXAMPLE 167

1-Octadecylcarbamoyl-2-methyl-3-(1-methoxycarbonyl-2-trimethylammonioethyl)carbamoylglycerol iodide In 2 ml of ether was dissolved 26 mg of the dimethylamino derivative as obtained in Example 166, and 0.2 ml of methyl iodide was added to the solution, followed by stirring for 15 hours. The reaction solution was concentrated to dryness and the residue was washed with ether to give 32 mg of the objective compound as a colorless powder.

IR(KBr, cm$^{-1}$) 3350, 2925, 2850, 1740, 1700, 1530, 1470, 1315, 1262, 1140, 1080, 788, 735.

NMR(90 MHz, CDCl$_3$) δ:0.87(3H, t), 1.25(32H, m), 3.13(2H, m), 3.43(3H, s), 3.53(9H, s), 3.5–3.6(1H, m), 3.80(3H, s), 3.9–4.4(6H, m), 4.92(1H, br), 5.07(1H, br), 6.97(1H, br).

TLC Rf=0.4[CHCl$_3$—MeOH—H$_2$O(65:25:2)].

EXAMPLE 168

2-[(3-Octadecylcarbamoyloxy-2-methoxy)propoxycarbonylamino]-3-trimethylammoniopropionate In 2 ml of tetrahydrofuran was dissolved 46 mg of the methyl ester derivative as obtained in Example 167, and 0.2 ml of conc. hydrochloric acid was added to the solution. The reaction solution was stirred at room temperature for 4 hours and neutralized with sodium hydrogencarbonate. The solvent was distilled off and the residue was purified by silica gel chromatography and reprecipitated from chloroform and acetone to give 10 mg of the objective compound.

IR(KBr, cm$^{-1}$) 3390, 2930, 2852, 1695, 1632, 1540, 1470, 1270, 1070.

TLC Rf=0.28[CHCl$_3$—MeOH—H$_2$O (65:25:2)]

Mass spectrum m/e: 574 (M+1).

EXAMPLE 169

3-[N-Acetyl-N-(N'-ethylpyridinio-2-yl)methyl]carbamoyl-1-hexadecylcarbamoyl-2-methylglycerol chloride (1) 2-Methyl-3-(2'-pyridylmethyl)carbamoyl-1-hexadecylcarbamoylglycerol In 4 ml of methylene chloride were dissolved 567 mg (1.52 mmole) of 1-hexadecylcarbamoyl-2-methylglycerol and 240 mg (3.04 mmole) of pyridine, and 261 mg (1.67 mmole) of phenyl chloroformate was added dropwise to the solution under ice-cooling, followed by stirring at room temperature for 1 hour. Aqueous sodium hydrogencarbonate (5%) solution was added to the reaction solution, followed by extraction with chloroform. The organic layer was dried over sodium sulfate and the solvent was distilled off under reduced pressure.

To the obtained crude carbonate was added 0.185 ml (1.82 mmole) of 2-(aminomethyl)pyridine, and the mixture was heated at 90° C. for 3 hours. After cooling, the crude product was purified by column chromatography [silica gel: 20 g; eluent: n-hexane/ethyl acetate=¼] to give 633 mg (82.1%) of the objective compound as a colorless solid.

TLC(silica gel: n-hexane/AcOEt=¼): Rf=0.25.

NMR(90 MHz, CDCl$_3$) δ:0.87(3H, t), 1.24(28H, s), 3.15(2H, q), 3.44(3H, s), 3.60(1H, quint), 4.18(4H, m), 4.50(2H, d), 4.85(1H, br), 5.95(1H, br), 7.23(2H, m), 7.67(1H, d, t), 8.53(1H, d, d).

IR(KBr)cm$^{-1}$: 3325, 2922, 2850, 1692, 1596, 1539, 1466, 1265, 1250.

(2) 3-[N-Acetyl-N-(2'-pyridylmethyl)]carbamoyl-2-methyl-1-hexadecylcarbamoylglycerol In 12.5 ml of pyridine was dissolved 633 mg (1.25 mmole) of the compound as synthesized in 1), and 2.35 ml (24.94 mmole) of acetic anhydride was added to the solution, followed by heating at 110° C. for 60 hours under a nitrogen atmosphere. The reaction solution was concentrated to dryness and 5% aqueous sodium hydrogencarbonate solution was added to the residue. Extraction with chloroform was conducted and the organic layer was dried over sodium sulfate. The solvent was distilled off under reduced pressure, and the obtained crude product was purified by column chromatography (silica gel: 27 g; eluent: n-hexane/ethyl acetate=½) to give 415 mg (60.5%) of the objective compound as a pale yellow solid.

TLC(silica gel; n-hexane/AcOEt): Rf=0.47.

NMR(90 MHz, CDCl$_3$) δ:0.87(3H, t), 1.25(28H, s), 2.62(3H, s), 3.14(2H, q), 3.30(3H, s), 3.47(1H, quint), 4.00(2H, d), 4.24(2H, d.d.), 4.83(1H, br), 5.09(2H, s), 7.17(2H, m), 7.62(1H, d, t), 8.49(1H, d,d)

IR(KBr)cm$^{-1}$: 3352, 2920, 2848, 1738, 1694, 1590, 1532, 1365, 1226.

(3) 3-[N-Acetyl-N-(N'-ethylpyridinio-2-yl)methyl]-carbamoyl-1-hexadecylcarbamoyl-2-methylglycerol chloride To 385 mg (0.70 mmole) of the compound as synthesized in (2) was added 3 ml of ethyl iodide, and the reaction solution was refluxed for 2 days under a nitrogen atmosphere under shielding from light. After cooling, the reaction solution was concentrated to dryness and the obtained iodide was treated with IRA-410(Cl$^-$) [30 ml; eluent: 70% methanol/water] to give 430 mg (100%) of the objective compound as a pale yellow powder.

TLC(silica gel; CHCl$_3$/MeOH=3/1): Rf=0.12.

NMR(90 MHz, CDCl$_3$) δ:0.87(3H, t), 1.24(28H, s), 1.71(3H, t), 2.64(3H, s), 3.10(2H, q), 3.37(3H, s), 3.66(1H, quint), 4.00(2H, d), 4.37(2H, m), 5.22(2H, q and 1H, br), 5.47(2H, s), 7.75(1H, br, d), 8.05(1H, br, t), 8.49(1H, br, t), 10.07(1H, br, d).

IR(KBr)cm$^{-1}$: 3425, 2925, 2851, 1750, 1700, 1629, 1532, 1466, 1371, 1220.

EXAMPLE 170

3-[N-Acetyl-N-(N'-ethylpyridinio-2-yl)methyl]carbamoyl-2-methyl-1-tetradecylcarbamoylglycerol chloride (1) 2-Methyl-3-(2'-pyridylmethyl)carbamoyl-1-tetradecylcarbamoylglycerol In 4 ml of methylene chloride were dissolved 518 mg (1.50 mmole) of 1-tetradecylcarbamoyl-2-methylglycerol and 237 mg (3.00 mmole) of pyridine, and 258 mg (1.65 mmole) of phenyl chloroformate was added dropwise to the solution under ice-cooling, followed by stirring at room temperature for 30 minutes. Aqueous sodium hydrogencarbonate (5%) solution was added to the reaction solution, followed by extraction with chloroform. The organic layer was dried over sodium sulfate and the solvent was distilled off under reduced pressure.

To the obtained crude carbonate was added 0.183 ml (1.80 mmole) of 2-(aminomethyl)pyridine, and the mixture was heated at 90° C. for 3 hours. After cooling, the crude product was purified by column chromatography (silica gel: 20 g; eluent: n-hexane/ethyl acetate=¼) to give 591 mg (82.1%) of the objective compound as a colorless solid.

TLC(silica gel; n-hexane/AcOEt=¼): Rf=0.20.

NMR(90 MHz, CDCl$_3$) δ:0.87(3H, t), 1.24(24H, s), 3.15(2H, q), 3.44(3H, s), 3.59(1H, quint), 4.18(4H, m), 4.50(2H, d), 4.82(1H, br), 5.92(1H, br), 7.22(2H, m), 7.66(1H, d, t), 8.53(1H, d, d).

IR(KBr)cm$^{-1}$: 3320, 2924, 2850, 1690, 1592, 1542, 1465, 1270

(2) 3-[N-Acetyl-N-(2'-pyridylmethyl)]carbamoyl-2-methyl-1-tetradecylcarbamoylglycerol In 11.7 ml of pyridine was dissolved 562 mg (1.17 mmole) of the compound as synthesized in 1), and 2.21 ml (23.43 mmole) of acetic anhydride was added to the solution, followed by heating at 110° C. for 60 hours under a nitrogen atmosphere. The reaction solution was concentrated to dryness and 5% aqueous sodium hydrogencarbonate solution was added to the residue, followed by extraction with chloroform. The organic layer was dried over sodium sulfate and the solvent was distilled off under reduced pressure. The obtained crude product was purified by column chromatography (silica gel: 25 g; eluent: n-hexane/ethyl acetate=½) to give 376 mg (61.5%) of the objective compound as a pale yellow solid.

TLC(silica gel; n-hexane/AcOEt=½) Rf=0.46.

NMR(90 MHz, CDCl$_3$) δ:0.87(3H, t), 1.24(24H, s), 2.60(3H, s), 3.13(2H, q), 3.28(3H, s), 3.47(1H, quint), 4.00(2H, d), 4.23(2H, d, d), 4.88(1H, br), 5.08(2H, s), 7.17(2H, m), 7.61(1H, d, t), 8.48(1H, d, d).

IR(KBr)cm$^{-1}$: 3352, 2920, 2850, 1738, 1694, 1590, 1532, 1365, 1225.

(3) 3-[N-Acetyl-N-(N'-ethylpyridinio-2-yl)methyl]-carbamoyl-2-methyl-1-tetradecylcarbamoylglycerol chloride To 365 mg (0.70 mmole) of the compound as synthesized in 2) was added 3 ml of ethyl iodide, and the reaction solution was heated under reflux for 2 days under a nitrogen atmosphere under shielding from light. After cooling, the reaction solution was concentrated to dryness and the obtained iodide was treated with IRA-410($Cl^-$) [30 ml; eluent: 70% methanol/water] to give 402 mg (98.0%) of the objective compound as a pale yellow powder.

TLC(silica gel; $CHCl_3$/MeOH=3/1): Rf=0.13.

NMR(90 MHz, $CDCl_3$) δ:0.87(3H, t), 1.25(24H, s), 1.71(3H, t), 2.65(3H, s), 3.11(2H, g), 3.37(3H, s), 3.66(1H, quint), 4.01(2H, d), 4.38(2H, m), 5.20(2H, q and 1H, br), 5.48(2H, s), 7.77(1H, br, d), 8.06(1H, br, t), 8.49(1H, br, t), 10.00(1H, br, d).

IR(KBr)$cm^{-1}$: 3390, 2920, 2850, 1750, 1700, 1625, 1524, 1450, 1370, 1215.

EXAMPLE 171

4-[N-Acetyl-N-(3-octadecylcarbamoyloxy-2-methoxypropoxycarbonyl)amino]methyl-3-ethylthiazolium chloride (i) 4-(3-Octadecylcarbamoyloxy-2-methoxypropoxycarbonylaminomethylthiazole A reaction mixture of 10.96 g (21 mmole) of 3-octadecylcarbamoyl-2-methyl-1-phenoxycarbonylglycerol as synthesized in the same manner as described in Example 9 and 2.1 g (21 mmole) of 4-aminomethylthiazole was heated at 50° C. overnight, and purified by silica gel (100 g) [eluent: n-hexane, ethyl acetate (1:1)] to give 7.5 g (yield 65.9%) of a pale yellow powder.

The IR spectrum of this product was the same as that of the product as obtained in Example 146.

(ii) 4-[N-Acetyl-N-(3-octadecylcarbamoyloxy-2-methoxypropoxycarbonyl)aminomethyl]thiazole In 18 ml of toluene were dissolved 6.3 g (11.3 mmole) of the thiazole derivative as obtained in (i), 5.6 g (46.5 mmole) of dimethylaminopyridine and 5.0 g (49 mmole) of acetic anhydride, and the reaction solution was heated at 70° C. for 4 days and concentrated to dryness under reduced pressure. The residue was purified by silica gel (60 g) [eluent: chloroform] and further by silica gel (60 g) [eluent: n-hexane-ethyl acetate (1:1)] to give 3.0 g (yield 45.5%) of a colorless solid.

The IR spectrum of this product was the same as that of the product as obtained in Example 147.

(iii) 4-[N-Acetyl-N-(3-octadecylcarbamoyloxy-2-methoxypropoxycarbonyl)amino]methyl-3-ethylthiazolium iodide In 20 ml of ethyl iodide was dissolved 3.0 g (5.1 mmole) of the acetate as obtained in (ii), and the reaction solution was heated at 120° C. overnight in a sealed vessel and concentrated to dryness under reduced pressure to give 3.78 g (yield 100%) of a pale yellow solid.

The IR spectrum of this product was the same as that of the product as obtained in Example 148.

(iv) 4-[N-Acetyl-N-(3-octadecylcarbamoyloxy-2-methoxycarbonyl)amino]methyl-3-ethylthiazolium chloride In 150 ml of 75% methanol was dissolved 3.3 g (4.46 mmole) of the iodide as obtained in iii), and the solution was passed through a column of IRA-410 ($Cl^-$) [150 ml] and washed with a small amount of 75% methanol. The effluent and washing were combined and concentrated to dryness under reduced pressure. The residue was recrystallized from 4 ml of acetone, 4 ml of ether and 40 ml of n-hexane to give 2.8 g (96.9%) of colorless crystals.

TLC [silica gel; $CHCl_3$, MeOH, $H_2O$ (65:25:4)] Rf=0.72 single spot.

IR [film]$cm^{-1}$: 3350, 2925, 2855, 1750, 1705, 1525, 1465, 1370, 1335, 1240, 1205, 1140, 1105, 1070, 1040, 995, 940.

NMR [60 MC, $CDCl_3$] δ:0.87(3H), 1.23(32H), 1.72(3H), 2.60(3H), 3.08(2H), 3.45(3H), 3.79(1H), 4.14(2H), 4.42(2H), 4.87(2H), 5.07(1H), 5.20(2H), 8.25(1H), 10.80(1H).

Elemental Analysis for $C_{32}H_{58}N_3O_6SCl\cdot H_2O$: Calcd.: C,57.68; H,9.08; N,6.31; S,4.81. Found: C,57.89; H,9.07; N,6.41; S,4.90.

EXAMPLE 172

4-[N-Acetyl-N-(3-octadecylcarbamoyloxy-2-methoxypropoxycarbonyl)amino]methyl-3-ethylthiazolium acetate In 15 ml of 75% methanol was dissolved 330 mg (0.446 mmole) of the iodide as obtained in Example 171, and the solution was passed through a column of IRA-410 ($AcO^-$) [15 ml], and washed with a small amount of 75% methanol. The effluent and washing were combined and concentrated to dryness under reduced pressure. The residue was recrystallized from 1 ml of ether and 15 ml of n-hexane to give 290 mg (97.0%) of colorless crystals.

TLC [silica gel; $CHCl_3$, MeOH, $H_2O$ (65:25:4)] Rf=0.72 single spot.

IR [film]$cm^{-1}$: 3350, 2925, 2855, 1750, 1705, 1600, 1525, 1465, 1370, 1335, 1240, 1205, 1140, 1105, 1070, 1040, 995, 940.

NMR [60 MC, $CDCl_3$] δ:0.87(3H), 1.23(32H), 1.72(3H), 2.02(3H), 2.60(3H), 3.08(2H), 3.45(3H), 3.79(1H), 4.15(2H), 4.42(2H), 4.88(2H), 5.07(1H), 5.21(2H), 8.25(1H), 10.80(1H).

EXAMPLE 173

3-[N-Acetyl-N-(N'-propylpyridinio-2-yl)methyl]carbamoyl-1-octadecylcarbamoyl-2-methylglycerol chloride To 173 mg (0.30 mmole) of the compound as synthesized in Example 103 was added 1 ml of n-propyl iodide, and the reaction solution was refluxed for 36 hours under a nitrogen atmosphere under shielding from light. After cooling, the reaction solution was concentrated to dryness and the resulting iodide was purified by column chromatography [silica gel: 10 g; eluent: chloroform/methanol=8/1] and treated with IRA-410 ($Cl^-$) [5 ml; eluent: 70% methanol/water] to give 118 mg (59.9%) of the objective compound as a pale yellow powder.

TLC [silica gel; $CHCl_3$/MeOH=3/1]: Rf=0.22.

NMR [90 MHz, $CDCl_3$] δ:0.86(3H,t), 1.10(3H,t), 1.23(32H,s), 2.05(2H,m), 2.65(3H,s), 3.10(2H,q), 3.37(3H,s), 3.65(1H,quint), 4.01(2H,d), 4.37(2H,br,t), 5.08(2H,t), 5.33(1H,br), 5.43(2H,s), 7.76(1H,br,d), 8.05(1H,br,t), 8.47(1H,br,t), 10.00(1H,br,d).

IR(KBr)$cm^{-1}$: 3425, 2924, 2852, 1750, 1700, 1628, 1532, 1468, 1370, 1220.

EXAMPLE 174

3-[N-Acetyl-N-(N'-allylpyridinio-2-yl)methyl]carbamoyl-1-octadecylcarbamoyl-2-methylglycerol chloride To 173 mg (0.30 mmole) of the compound as synthesized in Example 103 was added 1 ml of allyl iodide, and the reaction solution was refluxed for 16 hours under a nitrogen atmosphere under shielding from light. After cooling, the reaction solution was concentrated to dryness, and the residue was treated with IRA-410 ($Cl^-$)

[15 ml; eluent: 70% methanol/water]. The resulting chloride was purified by column chromatography [silica gel: 10 g; eluent: chloroform/methanol=8/1 to 3/1) to give 43 mg (21.9%) of the objective compound as a pale yellow powder.

TLC [silica gel; CHCl$_3$/MeOH=3/1]: Rf=0.25.

NMR (90 MHz, CDCl$_3$) δ:0.88(3H,t), 1.25(32H,s), 2.64 (3H,s), 3.13(2H,q), 3.39(3H,s), 3.68(1H,quint), 4.03(2H,br,d), 4.37(2H,m), 5.14–5.63(5H,m), 5.74–6.39(3H,m), 7.77(1H,br,d), 8.06(1H,br,t), 8.50(1H,br,t), 9.96(1H,br,d).

IR(KBr)cm$^{-1}$: 3400(br), 2920, 2850, 1750, 1700, 1624, 1530, 1465, 1220.

EXAMPLE 175

2-(3-Octadecylcarbamoyloxypropyloxycarbonyl)aminomethylpyridine

To 20 ml of dichloromethane were added 1.50 g of 3-(octadecylcarbamoyloxy)propanol (mp 80° C.) and 0.76 g of phenyl chlorocarbonate, and 0.4 g of pyridine was added to the solution with stirring under ice-cooling. The reaction solution was stirred under ice-cooling for 1 hour and further stirred at room temperature overnight. As aqueous sodium hydrogencarbonate solution was added to the solution, followed by stirring. The organic layer was separated, dried and concentrated. To the residue were added 518 mg of 2-aminomethylpyridine and 10 ml of chloroform, and the resulting mixture was refluxed for 15 hours and concentrated. The residue was purified by silica gel (100 g) chromatography [eluent: n-hexane-ethyl acetate (1:3)] to give 1.45 g of the objective compound.

TLC [silica gel; n-hexane-ethyl acetate (1:2)] Rf=0.25.

IR(KBr) cm$^{-1}$: 3300, 2905, 2840, 1680, 1530.

EXAMPLE 176

2-[N-(3-Octadecylcarbamoyloxypropoxycarbonyl)aminomethyl]-1-ethylpyridinium iodide In 5 ml of ethyl iodide was dissolved the pyridine derivative as obtained in Example 175, and the reaction solution was heated at 90° C. overnight in a sealed vessel and concentrated to dryness under reduced pressure. The residue was purified by silica gel (10 g) chromatography [eluent: chloroform-methanol (19:1)] to give 510 mg of the objective compound.

IR(KBr) cm$^{-1}$: 3320, 2925, 2850, 1690, 1635, 1535.

EXAMPLE 177

3-[N-Acetyl-N-(N'-butylpyridinio-2-yl)methyl]-carbamoyl-1-octadecylcarbamoyl-2-methylglycerol chloride To 173 mg (0.30 mmole) of the compound as synthesized in Example 103 was added 1 ml of n-butyl iodide, and the mixture was heated at 115° C. for 19 hours in nitrogen streams under shielding from light. After cooling, the reaction solution was concentrated to dryness and the resulting iodide was purified by column chromatography [silica gel : 5 g ; eluent : acetone/ethyl acetate=1/1] and treated with IRA-410 (Cl$^-$) [15 ml; eluent : 70% methanol/water] to give 134 mg (66.6%, pale yellow powder) of the desired compound.

TLC (silica gel; CHCl$_3$/MeOH=5/1) : Rf=0.10.

NMR (90 MHz, CDCl$_3$) δ:0.87(3H,t), 1.00(3H,t), 1.23 (32H,s), 1.42–1.64(4H,m), 2.66(3H,s), 3.12(2H,q), 3.37(3H,s), 3.67(1H,quint), 4.01(2H,d), 4.38(2H,m), 5.08(2H,t), 5.44 (2H,s), 5.47(1H,br,t), 7.83(1H,d), 8.07(1H,t), 8.57(1H,t), 9.97(1H,d).

IR(KBr) cm$^{-1}$: 3425, 2920, 2852, 1755, 1702, 1627, 1534, 1465, 1370, 1220.

EXAMPLE 178

3-[N-Acetyl-N-(N'-ethylpyridinio-2-yl)methyl]carbamoyl-2-methyl-1-dodecylcarbamoylglycerol chloride (1) 2-Methyl-3-(2'-pyridylmethyl)carbamoyl-1-dodecylcarbamoylglycerol In 5 ml of methylene chloride were dissolved 561 mg (1.77 mmole) of 1-dodecylcarbamoyl-2-methylglycerol and 280 mg (3.53 mmole) of pyridine. To the solution was added dropwise, under ice-cooling, 305 mg (1.94 mmole) of phenylchloroformate, followed by stirring at room temperature for one hour. To the reaction solution was added a 5% aqueous solution of sodium hydrogencarbonate, which was subjected to extraction with chloroform. The organic layer was dried over sodium sulfate, from which the solvent was distilled off under reduced pressure.

To the crude carbonate thus obtained was added 0.216 ml (2.12 mmole) of 2-(aminomethyl)pyridine, and the mixture was heated at 90° C. for 3 hours. After cooling, the crude product was purified by means of column chromatography (silica gel : 40 g; eluent : n-hexane/ethyl acetate=½) to give 670 mg (84.0%, a colorless oily substance) of the desired product.

TLC (silica gel ; AcOEt) : Rf=0.34.

NMR (90 MHz, CDCl$_3$) δ:0.87(3H,t), 1.25(20H,s), 3.14 (2H,q), 3.43(3H,s), 3.59(1H,quint), 4.17(4H,m), 4.50(2H,d), 4.89(1H,br), 6.00(1H,br), 7.23(2H,m), 7.66(1H,d,t), 8.53(1H,d,d).

IR(KBr) cm$^{-1}$: 3305, 2915, 2850, 1690, 1593, 1544, 1468, 1311, 1275.

(2) 3-[N-Acetyl-N-(2'-pyridylmethyl)]carbamoyl-2-methyl-1-dodecylcarbamoylglycerol In 10.0 ml of pyridine was dissolved 452 mg (1.00 mmole) of the compound as synthesized in (1). To the solution was added 1.89 ml (20.00 mmole) of acetic anhydride. The mixture was then heated at 120° C. for 48 hours in nitrogen streams. The reaction mixture was concentrated to dryness. To the concentrate was added a 5% aqueous solution of sodium hydrogecarbonate, followed by extraction with chloroform. The organic layer was dried over sodium sulfate, from which the solvent was distilled off under reduced pressure. The resultant crude product was purified by means of column chromatography (silica gel : 20 g; eluent : n-hexane/ethyl acetate=1/1) to give 302 mg (61.2%, pale yellow solid substance) of the desired product.

TLC (silica gel ; n-hexane/ethyl acetate=1/1): Rf=0.20.

NMR (90 MHz, CDCl$_3$) δ:0.86(3H,t), 1.26(20H,s), 2.63 (3H,s), 3.16(2H,q), 3.33(3H,s), 1H,quint), 4.03(2H,d), 4.26(2H,d,d), 4.98(1H,br), 5.15(2H,s), 7.21(2H,m), 7.73(1H,d,t,), 8.63(1H,d,d).

IR(Film) cm$^{-1}$: 3325, 2918, 2848, 1738, 1702, 1592, 1531, 1465, 1440, 1348, 1210.

(3) 3-[N-Acetyl-N-(N'-ethylpyridinio-2-yl)methyl]-carbamoyl-2-methyl-1-dodecylcarbamoylglycerol chloride To 300 mg (0.61 mmole) of the compound as synthesized in 2) was added 3 ml of ethyl iodide, which was heated at 120° C. in a sealed tube. After cooling, the reaction solution was concentrated to dryness. The resultants iodide was treated with IRA-410 (Cl$^-$) [40 ml; eluent: 70% methanol/water] to give 300 mg (88.4%, pale yellow viscous substance) of the desired product.

TLC (silica gel : CHCl$_3$/MeOH=3/1) : Rf=0.16.

NMR (90 MHz, CDCl$_3$) δ:0.89(3H,t), 1.26(20H,s), 1.70 (3H,m), 2.65(3H,s), 3.10(2H,m), 3.37(3H,s), 3.61(1H,m), 4.01(2H,br), 4.38(2H,br), 5.09(2H,m and 1H,br), 5.46(2H,br,s), 7.81(1H,br), 8.08(1H,br), 8.51(9.69(1H,br).

IR(KBr) cm$^{-1}$: 3325, 2910, 2850, 1740, 1690, 1630, 1581, 1520, 1452, 1359, 1210, 1160, 1092.

For reference' sake, structural formulae of the compounds as synthesized in Examples are shown as follows:

Example 1

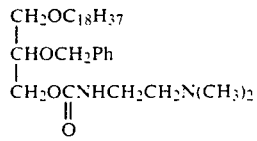

Example 2

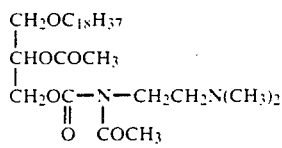

Example 3

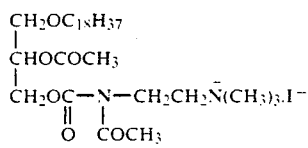

Example 4

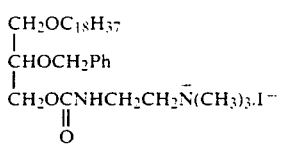

Example 5

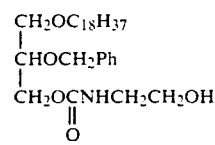

Example 6

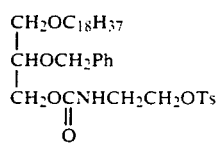

Example 7

Example 8

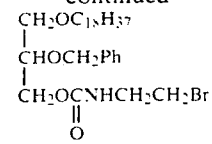

Example 9

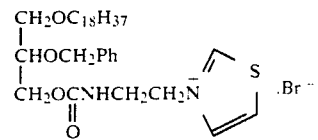

Example 10

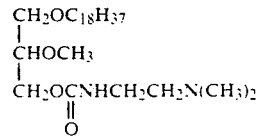

Example 11

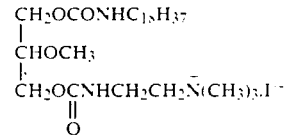

Example 12

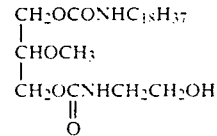

Example 13

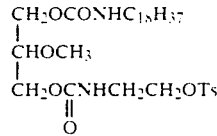

Example 14

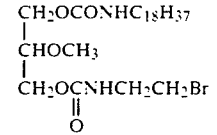

Example 15

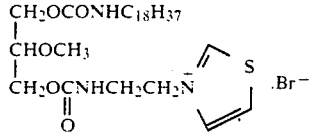

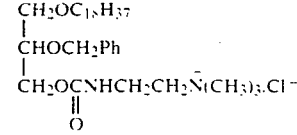

-continued
Example 16
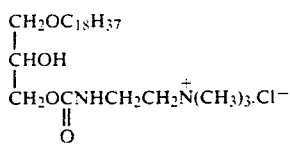
Example 17
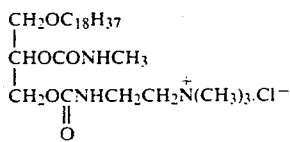
Example 18
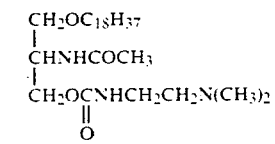
Example 19
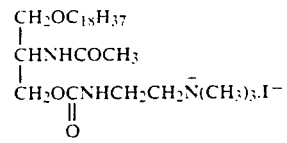
Example 20
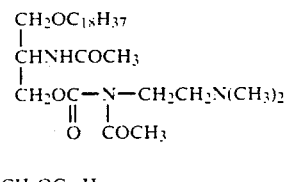
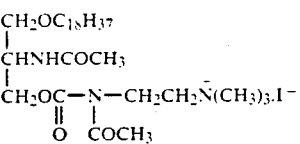
Example 21
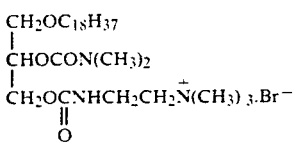
Example 22
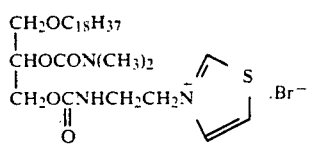
Example 23
-continued
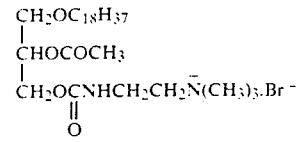
Example 24
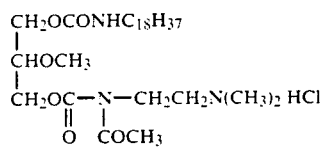
Example 25
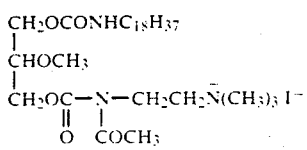
Example 26
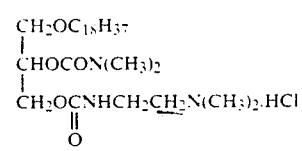
Example 27
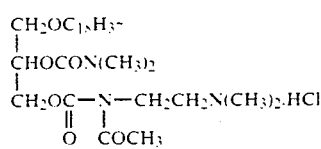
Example 28
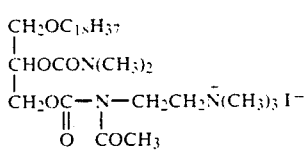
Example 29
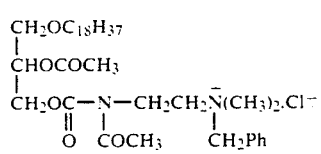
Example 30
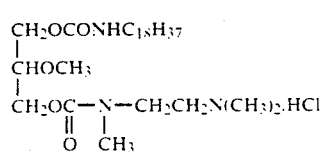
Example 31

-continued
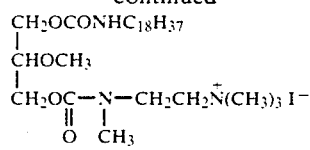
Example 32
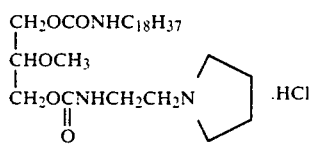
Example 33
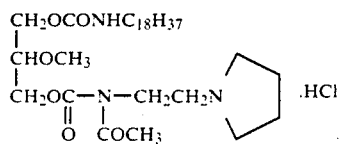
Example 34
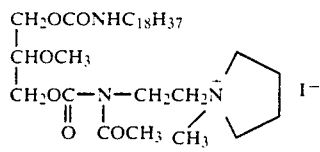
Example 35
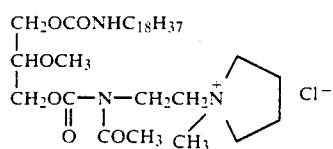
Example 36
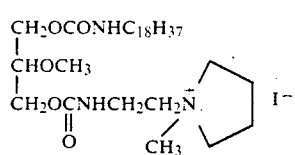
Example 37
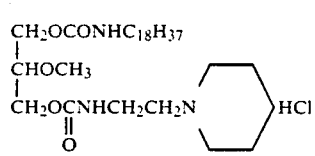
Example 38
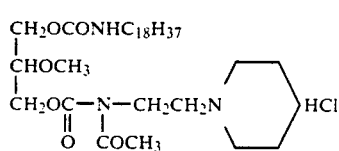
Example 39
-continued
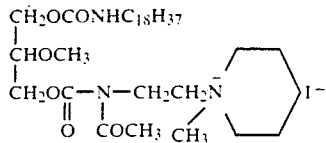
Example 40
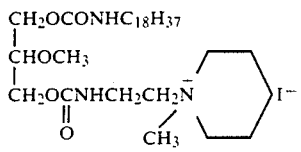
Example 41
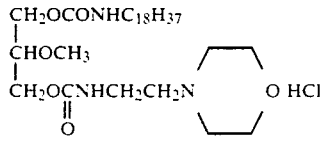
Example 42
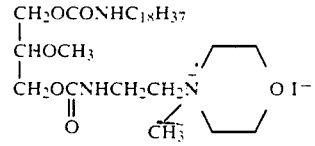
Example 43
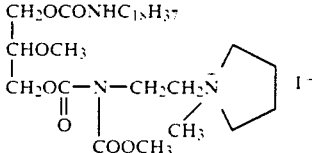
Example 44
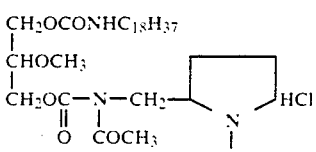
Example 45
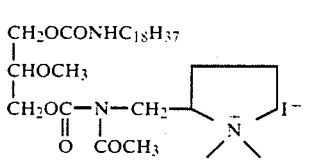
Example 46
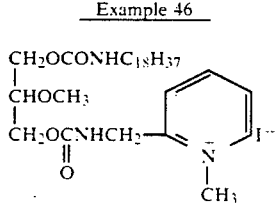
Example 47

-continued
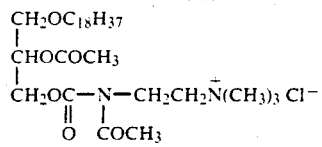
Example 48
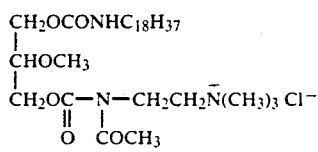
Example 49
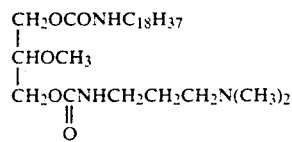
Example 50
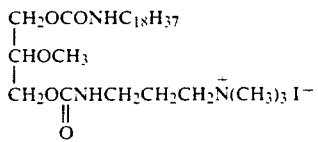
Example 51
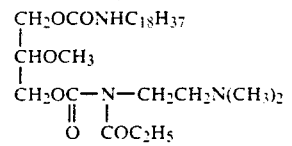
Example 52
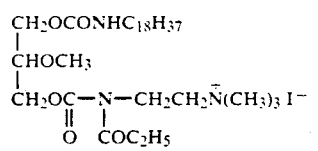
Example 53
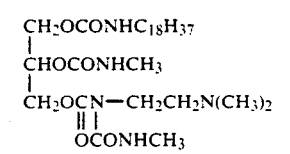
Example 54
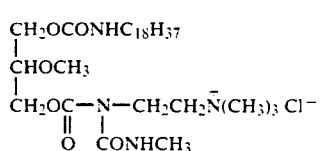
Example 55
-continued
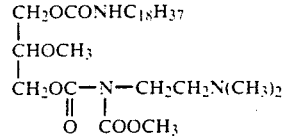
Example 56
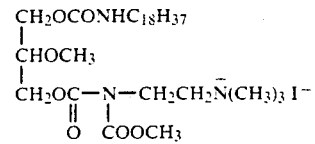
Example 57
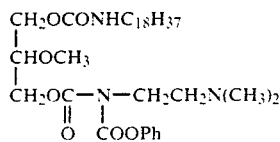
Example 58
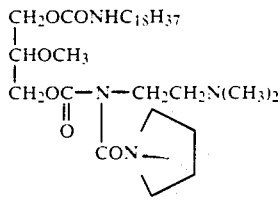
Example 59
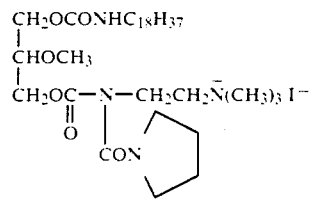
Example 60
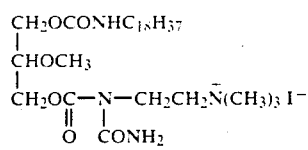
Example 61
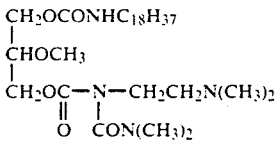
Example 62
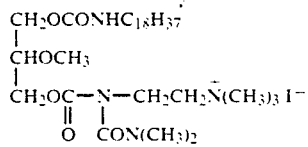
Example 63

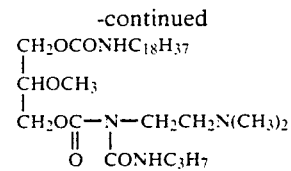
Example 64
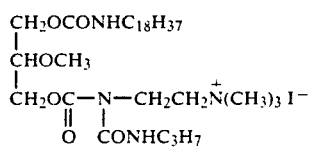
Example 65
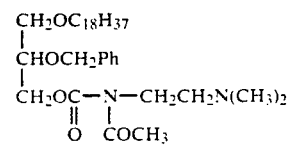
Example 66
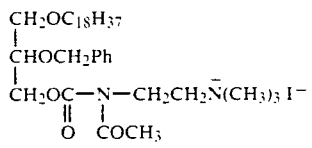
Example 67
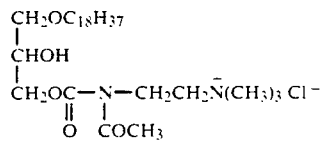
Example 68
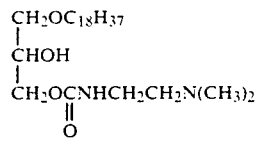
Example 69
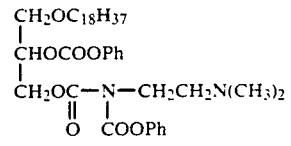
Example 70
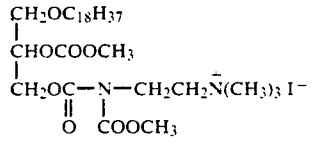
Example 71
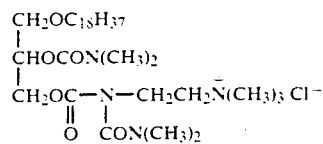
Example 72
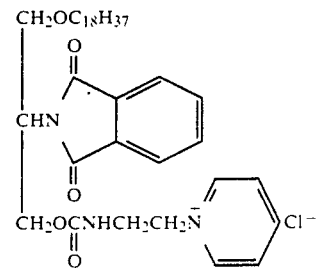
Example 73
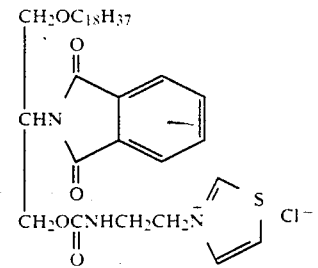
Example 74
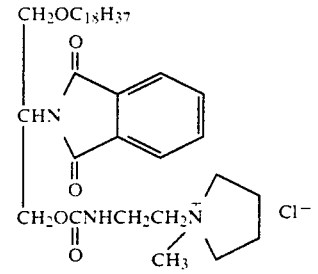
Example 75
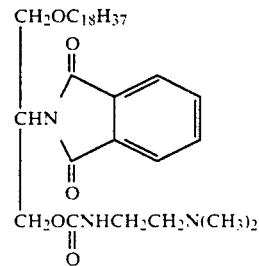
Example 76

-continued
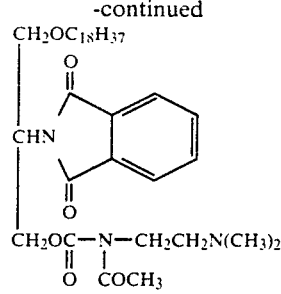
Example 77
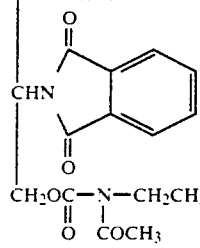
Example 78
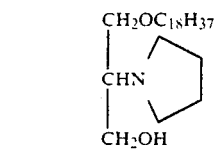
Example 79
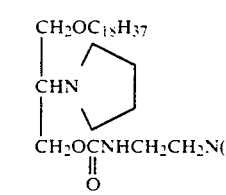
Example 80
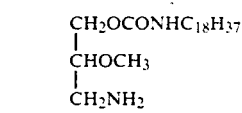
Example 81
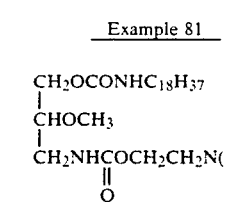
Example 82
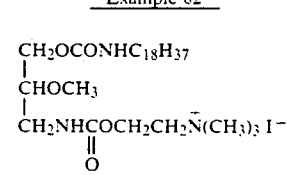
Example 83
-continued
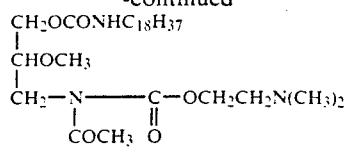
Example 84
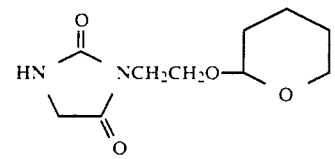
Example 85
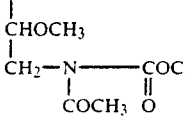
Example 86
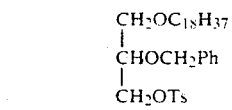
Example 87
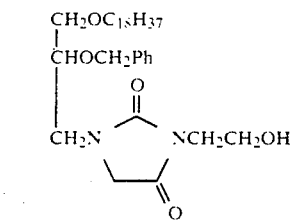
Example 88
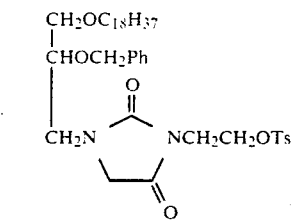
Example 89
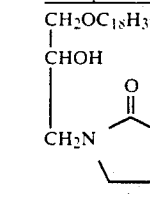
Example 90

-continued
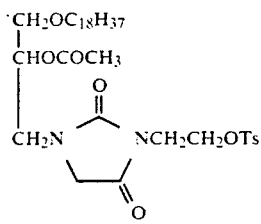
Example 91
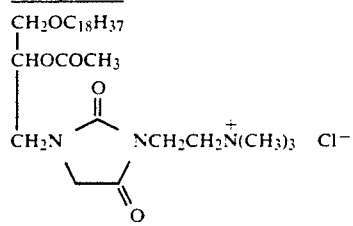
Example 92
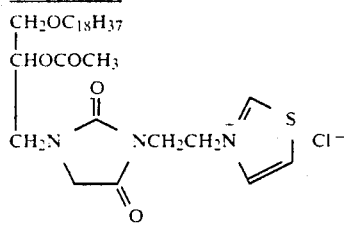
Example 93
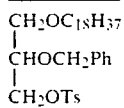
Example 94
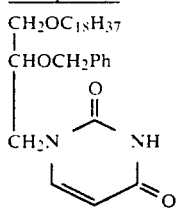
Example 95
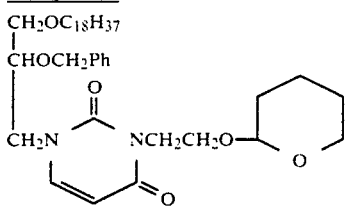
Example 96
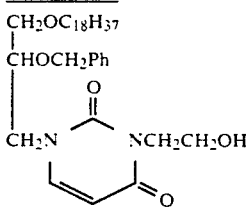
Example 97
-continued
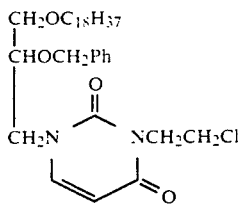
Example 98
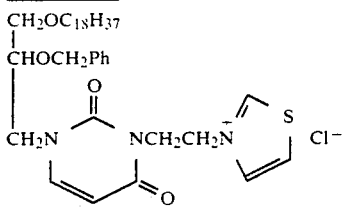
Example 99
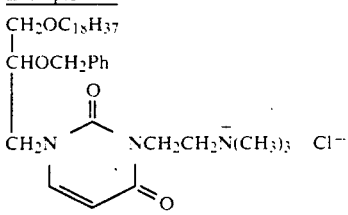
Example 100
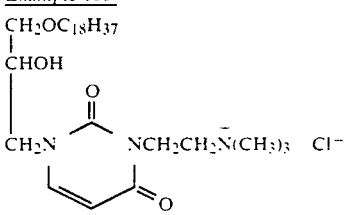
Example 101
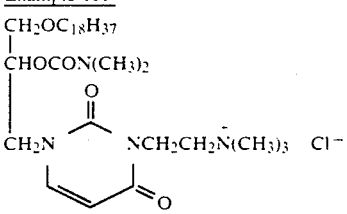
Example 102
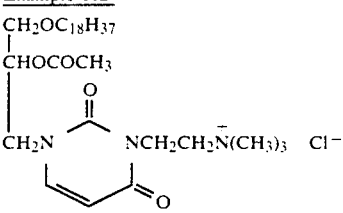
Example 103
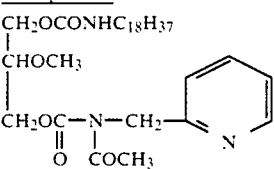
Example 104

Example 105
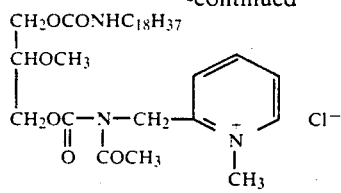
Example 106
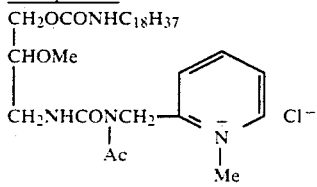
Example 107
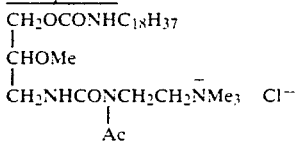
Example 108
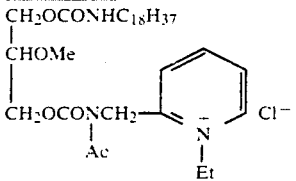
Example 109
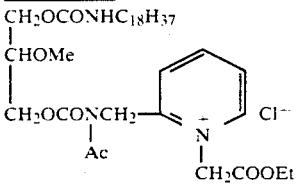
Example 110
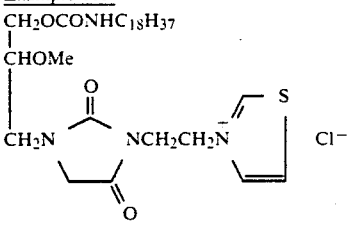
Example 111
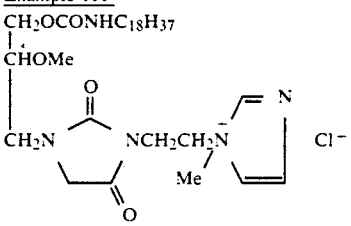
Example 112
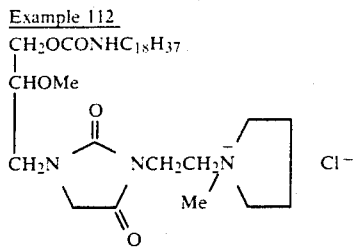
Example 113
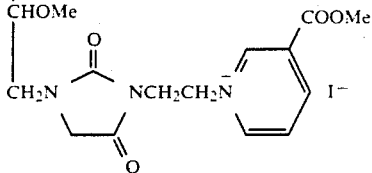
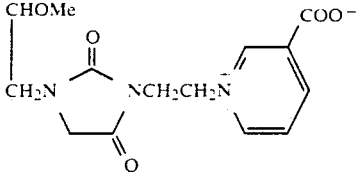
Example 114
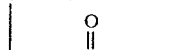
Example 115
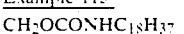
Example 116
Example 117
Example 118

-continued

CH₂OCONHC₁₈H₃₇
|
CHOMe
|
CH₂OCONH 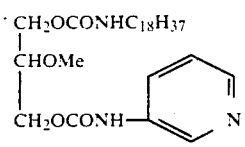

Example 119

CH₂OCONHC₁₈H₃₇
|
CHOMe
|
CH₂OCONH 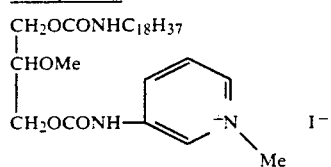   I⁻

Example 120

CH₂OCONHC₁₈H₃₇
|
CHOMe
|
CH₂OCON 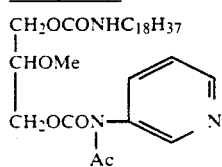
         |
         Ac

Example 121

CH₂OCONHC₁₈H₃₇
|
CHOMe
|
CH₂OCON 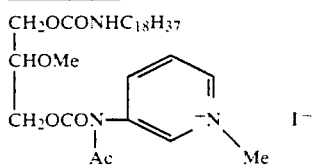   I⁻
         |
         Ac

Example 122

CH₂OCONHC₁₈H₃₇
|
CHOMe
|
CH₂OCONH 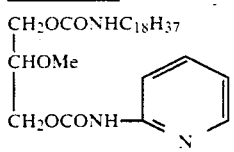

Example 123

CH₂OCONHC₁₈H₃₇
|
CHOMe        Me
|            |
CH₂OCONHCH₂CH₂—N⁺CH₂COOEt   Cl⁻
             |
             Me

Example 124

CH₂OCONHC₁₈H₃₇
|
CHOMe        Me
|            |
CH₂OCONHCH₂CH₂—N⁺CH₂COO⁻
             |
             Me

Example 125

CH₂O Trityl
|
CHOMe
| 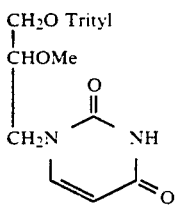

Example 126

-continued

CH₂O Trityl
|
CHOMe
| 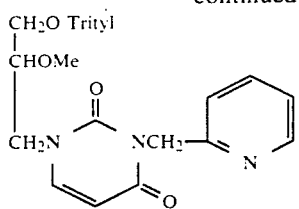

Example 127

CH₂OH
|
CHOMe
| 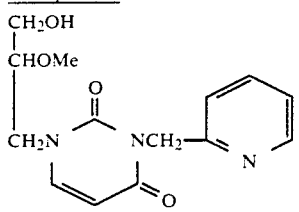

Example 128

CH₂OCONHC₁₈H₃₇
|
CHOMe
| 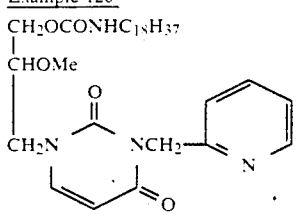

Example 129

CH₂OCONHC₁₈H₃₇
|
CHOMe
| 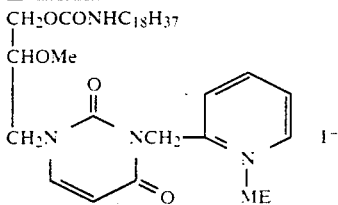   I⁻

Example 130

CH₂O Trityl
|
CHOMe
| 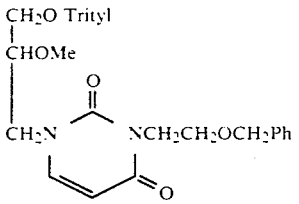

Example 131

CH₂OH
|
CHOMe
| 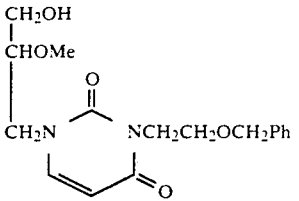

Example 132

CH₂OCONHC₁₈H₃₇
|
CHOMe
| 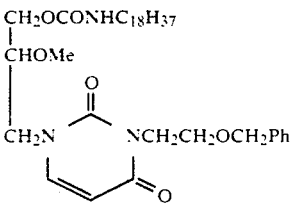

Example 133

-continued

Example 133 (continued)
CH₂OCONHC₁₈H₃₇
|
CHOMe
|
CH₂N(C(O)N(CH₂CH₂OH))CH=CH-C(O)

Example 134
CH₂OCONHC₁₈H₃₇
|
CHOMe
|
CH₂N(C(O)N(CH₂CH₂OTs))CH=CH-C(O)

Example 135
CH₂OCONHC₁₈H₃₇
|
CHOMe
|
CH₂N(C(O)N(CH₂CH₂N⁺=CH-S-CH=CH))CH=CH-C(O)    Cl⁻

Example 136
CH₂OCONHC₁₈H₃₇
|
CHOMe
|
CH₂N(C(O)N(CH₂CH₂NMe₃))CH=CH-C(O)    Cl⁻

Example 137
CH₂OCONHC₁₈H₃₇
|
CHOMe
|
CH₂N(C(O)N(CH₂CH₂N⁺(Me)(pyrrolidine)))CH=CH-C(O)    Cl⁻

Example 138
CH₂OCONHC₁₈H₃₇
|
CHOMe
|
CH₂OCONHCH₂—(thiazole)

Example 139
CH₂OCONHC₁₈H₃₇
|
CHOMe
|
CH₂OCONCH₂—(thiazole)
    |
    Ac

Example 140
CH₂OCONHC₁₈H₃₇
|
CHOMe
|
CH₂OCONHCH₂—(N-Me-thiazolium)    I⁻

Example 141
CH₂OCONHC₁₈H₃₇
|
CHOMe
|
CH₂OCONHCH₂—(N-Et-thiazolium)    I⁻

Example 142
CH₂OCONHC₁₈H₃₇
|
CHOMe
|
CH₂OCONCH₂—(N-Me-thiazolium)    I⁻
    |
    Ac Example 143
CH₂OCONHC₁₈H₃₇
|
CHOMe
|
CH₂OCONCH₂—(N-Et-thiazolium)    I⁻
    |
    Ac Example 144
CH₂OCONHC₁₈H₃₇
|
CHOMe
|
CH₂OCONCH₂—(N-Pr-thiazolium)    I⁻
    |
    Ac Example 145
CH₂OCONHC₁₈H₃₇
|
CHOMe
|
CH₂OCONCH₂—(N-Bu-thiazolium)    I⁻
    |
    Ac Example 146
CH₂OCONHC₁₈H₃₇
|
CHOMe
|
CH₂OCONHCH₂—(thiazole)

Example 147
CH₂OCONHC₁₈H₃₇
|
CHOMe
|
CH₂OCONCH₂—(thiazole)
    |
    Ac

Example 148
CH₂OCONHC₁₈H₃₇
|
CHOMe
|
CH₂OCONCH₂—(N-Me-thiazolium)    I⁻
    |
    Ac Example 149
CH₂OCONHC₁₈H₃₇
|
CHOMe
|
CH₂OCONCH₂—(N-Et-thiazolium)    I⁻
    |
    Ac -continued Example 150
CH₂OCONHC₁₈H₃₇
|
CHOMe
|
CH₂OCONHCH₂CH₂—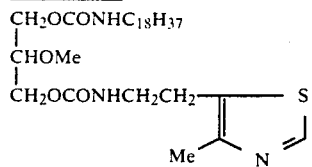

Example 151
CH₂OCONHC₁₈H₃₇
|
CHOMe
|
CH₂OCONHCH₂CH₂—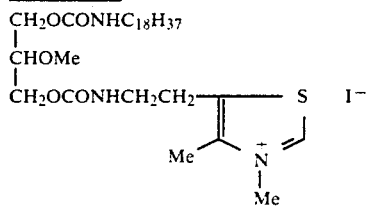 I⁻

Example 152
CH₂OCONHC₁₈H₃₇
|
CHOMe
|
CH₂OCONCH₂CH₂—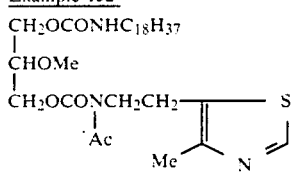
   |
   Ac

Example 153
CH₂OCONHC₁₈H₃₇
|
CHOMe
|
CH₂OCONCH₂CH₂—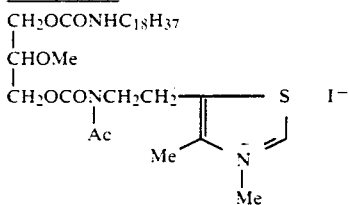 I⁻
   |
   Ac

Example 154
CH₂OCONHC₁₈H₃₇
|
CHOMe
|
CH₂OCON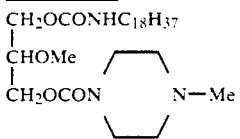N—Me

Example 155
CH₂OCONHC₁₈H₃₇
|
CHOMe
|
CH₂OCON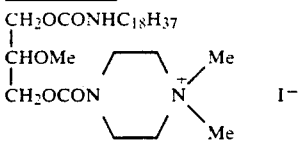 I⁻

Example 156
CH₂OCONHC₁₈H₃₇
|
CHOMe
|
CH₂OCON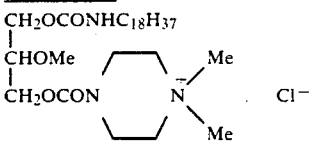 Cl⁻

Example 157
CH₂OCONHC₁₈H₃₇
|
CHOMe
|
CH₂OCONH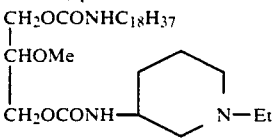N—Et

Example 158
-continued
CH₂OCONHC₁₈H₃₇
|
CHOMe
|
CH₂OCONH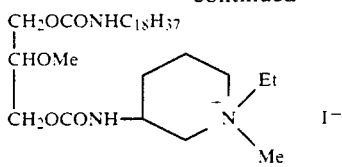 I⁻

Example 159
CH₂OCONHC₁₈H₃₇
|
CHOMe
|
CH₂OCON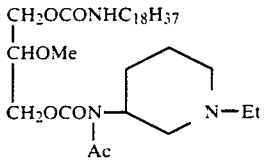N—Et
   |
   Ac

Example 160
CH₂OCONHC₁₈H₃₇
|
CHOMe
|
CH₂OCON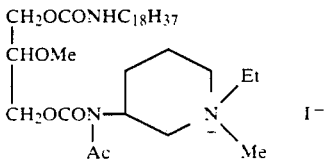 I⁻
   |
   Ac

Example 161
CH₂OCONHC₁₈H₃₇
|
CHOMe
|
CH₂OCON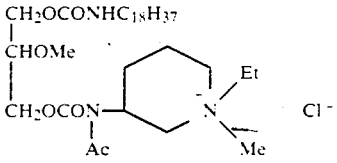 Cl⁻
   |
   Ac

Example 162
CH₂OCONHC₁₈H₃₇
|
CHOMe
|
CH₂OCOOCCl₃

Example 163
CH₂OCONHC₁₈H₃₇
|
CHOMe
|
CH₂OCONHCHCH₂OCH₂Ph
          |
          COOMe Example 164
CH₂OCONHC₁₈H₃₇
|
CHOMe
|
CH₂OCONHCHCH₂OH
          |
          COOMe Example 165
CH₂OCONHC₁₈H₃₇
|
CHOMe
|
CH₂OCONHC=CH₂
          |
          COOMe Example 166
CH₂OCONHC₁₈H₃₇
|
CHOMe
|
CH₂OCONHCHCH₂NMe₂
          |
          COOMe Example 167

-continued

```
CH₂OCONHC₁₈H₃₇
|
CHOMe
|
CH₂OCONHCHCH₂N⁺Me₃    I⁻
            |
            COOMe
```

Example 168
```
CH₂OCONHC₁₈H₃₇
|
CHOMe
|
CH₂OCONHCHCH₂N⁺Me₃
            |
            COO⁻
```

Example 169
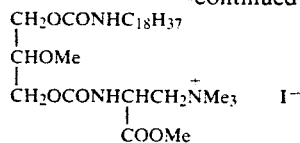
```
CH₂OCONHC₁₆H₃₃
|
CHOMe
|
CH₂OCONCH₂
        |
        Ac
```

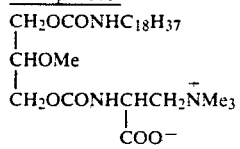
```
CH₂OCONHC₁₆H₃₃
|
CHOMe
|
CH₂OCONCH₂        Cl⁻
        |
        Ac
```

Example 170
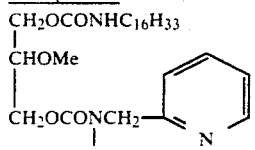
```
CH₂OCONHC₁₄H₂₉
|
CHOMe
|
CH₂OCONCH₂
        |
        Ac
```

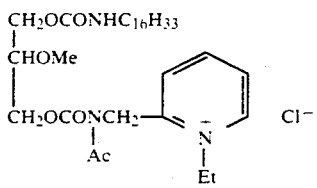
```
CH₂OCONHC₁₄H₂₉
|
CHOMe
|
CH₂OCONCH₂        Cl⁻
        |
        Ac
```

Example 171
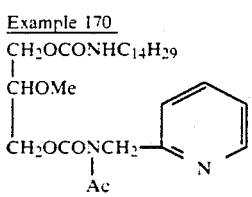
```
CH₂OCONHC₁₈H₃₇
|
CHOMe
|
CH₂OCONCH₂        Cl⁻
        |
        Ac
```

Example 172
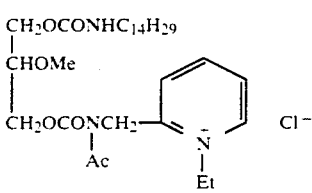
```
CH₂OCONHC₁₈H₃₇
|
CHOMe
|
CH₂OCONCH₂        CH₃COO⁻
        |
        Ac
```

Example 173
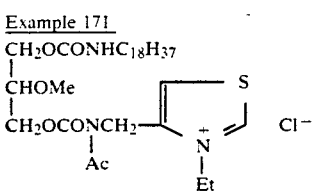
```
CH₂OCONHC₁₈H₃₇
|
CHOMe
|
CH₂OCONCH₂        Cl⁻
        |
        Ac
```

-continued

Example 174
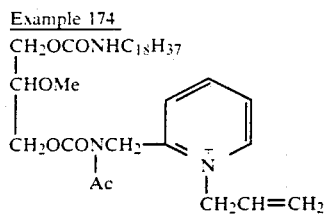
```
CH₂OCONHC₁₈H₃₇
|
CHOMe
|
CH₂OCONCH₂
        |
        Ac
```

Example 175
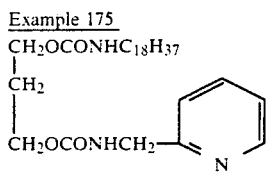
```
CH₂OCONHC₁₈H₃₇
|
CH₂
|
CH₂OCONHCH₂
```

Example 176
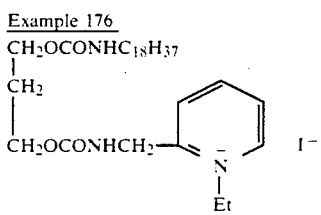
```
CH₂OCONHC₁₈H₃₇
|
CH₂
|
CH₂OCONHCH₂        I⁻
```

Example 177
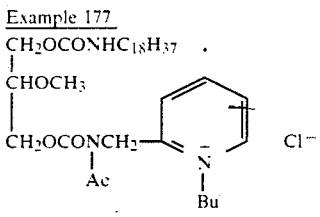
```
CH₂OCONHC₁₈H₃₇
|
CHOCH₃
|
CH₂OCONCH₂        Cl⁻
        |
        Ac
```

Example 178
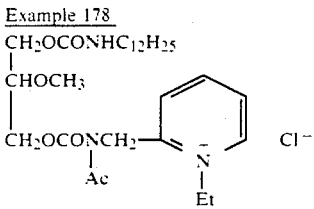
```
CH₂OCONHC₁₂H₂₅
|
CHOCH₃
|
CH₂OCONCH₂        Cl⁻
        |
        Ac
```

In the above-mentioned formulae, Ac is acetyl; Bu is butyl; Et is ethyl; Me is methyl; Ph is phenyl; Pr is propyl; Trityl is trityl; and Ts is tosyl.

EXPERIMENT EXAMPLE 1

Inhibitory activity on platelet aggregation

Method

With use of an injection syringe containing 3.15% citric acid (at a ratio of 1 part against 9 parts of blood) as an anticoagulant, blood was collected by cardiac puncture from a male rabbit. The blood was then centrifuged at room temperature at 800 r.p.m. for 10 minutes to prepare platelet rich plasma (PRP). The remaining blood was further centrifuged at 3000 r.p.m. for 10 minutes to separate platelet poor plasma (PPP) as a supernatant liquid. The PRP was diluted with the PPP to adjust the number of platelets to about $5 \times 10^5$ per $\mu l$. This PRP (250 $\mu l$) was stirred at 37° C. for 2 minutes, and a test drug was added. After the mixture was stirred for 2 minutes, $1 \times 10^{-8}$M of PAF was added to the mixture. Platelet aggregation was determined with an aggregometer (manufactured by Rika Denki K.K.). The inhibitory activity on platelet aggregation of the test drug was determined from the inhibition rate in relation to the maximum transmission (maximum aggregation ratio) of control PRP by PAF.

Results

The results are shown in Table 1.

TABLE 1

| Test compound (Example No.) | Inhibitory activity against rabbit platelet aggregation by PAF | | |
|---|---|---|---|
| | Test drug concentration and rate of inhibition (%) | | |
| | $1 \times 10^{-6}M$ | $3 \times 10^{-6}M$ | $3 \times 10^{-5}M$ |
| 3 | 86 | 100 | 100 |
| 8 | | | 100 |
| 10 | | | 82 |
| 14 | | 52 | 100 |
| 19 | | | 72 |
| 20 | | 100 | 100 |

EXPERIMENT EXAMPLE 2

Preventive activity against PAF-induced death in mice

Method

The test drug was investigated for the preventive activity against shock death to be brought about within 30 min. after 50 μg/kg of PAF in the form of 0.1 ml/kg physiological saline solution was given intravenously to a male Jcl-ICR mouse. The test drug was administered intravenously 5 min. before the injection of PAF.

Results

The results are shown in Table 2. In the case of administration of PAF, the survival rate in mice was 19%, whereas pretreatment through intravenous administration of 0.1 and 1 mg/kg each of the compound of Example 3 improved markedly the survival rate of 38 and 100%, respectively, leading to the conclusion that this command is a potent drug for prevention of PAF-induced death.

TABLE 2

| Test compound Example No. | Preventive activity against PAF-induced death in mice | | | |
|---|---|---|---|---|
| | Dose | | Group | Survival rate (%) |
| | Test drug mg/kg. i.v. | PAF ug/kg. i.v. | (Mice survived)/ (mice employed) | |
| Control | — | 50 | 3/16 | 19 |
| 3 | 0.1 | 50 | 3/8 | 38 |
| 3 | 1.0 | 50 | 8/8 | 100 |

EXPERIMENT EXAMPLE 3

In accordance with the same procedure as described in Experiment Example 1, the test compounds were investigated for the inhibitory activity against platelet aggregation by PAF. The results are shown in Table 3.

TABLE 3

| Test compound (Example No.) | Inhibitory activity against rabbit platelet aggregation by PAF | | | |
|---|---|---|---|---|
| | Test drug concentration and rate of inhibition (%) | | | |
| | $3 \times 10^{-7}M$ | $1 \times 10^{-6}M$ | $3 \times 10^{-6}M$ | $3 \times 10^{-5}M$ |
| 25 | | 40 | 100 | 100 |
| 35 | 45 | | 100 | 100 |
| 43 | | | 100 | 100 |
| 56 | | | 64 | 100 |
| 62 | | | 34 | 100 |
| 45 | 41 | | 100 | 100 |
| 91 | 78 | | 100 | 100 |
| 92 | | | 100 | 100 |
| 102 | | 72 | 100 | 100 |
| 104 | 100 | | 100 | 100 |

EXPERIMENT EXAMPLE 4

In accordance with the same procedure as described in Experiment Example 2, the test compounds were investigated for the preventive activity against PAF-induced death in mice. The results are shown in Table 4.

TABLE 4

| Test compound Example No. | Preventive activity against PAF-induced death in mice | |
|---|---|---|
| | Dose mg/kg i.v. | Survival rate (%) |
| (Control) | — | 24 |
| 25 | 1.0 | 94 |
| 35 | 1.0 | 80 |
| 43 | 1.0 | 100 |
| 45 | 1.0 | 100 |
| 45 | 0.3 | 77 |
| 91 | 1.0 | 100 |
| 92 | 1.0 | 100 |
| 92 | 0.3 | 77 |

EXPERIMENT EXAMPLE 5

Restoring activity against PAF-induced hypotension

Method

Male S. D. rats, aged 16 weeks, were employed.

Under anesthesia with pentobarbital, cannulas were inserted into the femoral artery and vein of rats for measurement of blood pressure and for administration of a drug, respectively. Three (3) minutes after intravenous administration of 1 μg/kg (0.25% BAS physiological saline solution; volume of 0.2 ml/kg) of PAF, a test drug (physiological saline solution; volume of 0.5 ml/kg) was administered intravenously, and blood pressure was measured for subsequent 1 hour.

The ratio of hypertension by the test drug to hypotension by PAF was taken as a restoration rate.

Restoration rate (%) = [(Blood pressure just before i.v. administration of a test drug) − (Blood pressure 1 min. after i.v. administration of a test drug)/(Blood pressure just before i.v. administration of PAF) − (Blood pressure just before i.v. administration of a test drug)] × 100

The results are shown in Table 5.

TABLE 5

| Test drug (Example No.) | Restoration from PAF-induced hypotension | |
|---|---|---|
| | Dose mg/kg i.v. | Restoration rate (%) |
| 3 | 0.5 | 48 |
| 25 | 1.0 | 69 |
| 35 | 0.5 | 73 |
| 43 | 0.5 | 83 |
| 91 | 0.5 | 77 |

TABLE 5-continued

| Restoration from PAF-induced hypotension | | |
|---|---|---|
| Test drug (Example No.) | Dose mg/kg i.v. | Restoration rate (%) |
| 92 | 0.5 | 77 |
| 104 | 0.1 | 94 |

EXPERIMENT EXAMPLE 6

In accordance with the same procedure as described in Experiment Example 1, the test compounds were investigated for the inhibitory activity against platelet aggregation by PAF. The results are shown in Table 6.

TABLE 6

| Test Compound (Example No.) | Inhibitory activity against rabbit platelet aggregation by PAF | | | |
|---|---|---|---|---|
| | Test drug concentration and rate of inhibition (%) | | | |
| | $3 \times 10^{-8}$M | $3 \times 10^{-7}$M | $3 \times 10^{-6}$M | $3 \times 10^{-5}$M |
| 108 | | 100 | 100 | 100 |
| 110 | | 34 | 100 | 100 |
| 115 | | 9 | 100 | 100 |
| 116 | | 100 | 100 | 100 |
| 117 | | 100 | 100 | |
| 136 | | 11 | 100 | 100 |
| 140 | 18 | 100 | 100 | 100 |
| 142 | 25 | 100 | 100 | 100 |
| 143 | | 100 | 100 | |
| 144 | 9 | 100 | 100 | |
| 145 | | 100 | 100 | |
| 148 | | 42 | 100 | |
| 149 | 78 | 100 | 100 | |
| 161 | | 6 | 100 | 100 |
| 169 | | 100 | 100 | 100 |
| 170 | | 100 | 100 | 100 |
| 173 | | 100 | 100 | 100 |
| 174 | | 100 | 100 | 100 |

EXPERIMENT EXAMPLE 7

Inhibitory activity against PAF-induced hypotension in rats

Method

Male Spraque-Dawley rats, with a body weight of about 400 g, were used under pentobarbital sodium (50 mg/kg, intravenous administration) anesthesia. A cannula was inserted into the femoral artery and secured in position for measurement of blood pressure and another cannula into the femoral vein for administration of a solution of the drug. The blood pressure was measured via a pressure transducer and recorded on a polygraph. First, 0.3 μg/kg of PAF was administered intravenously and the hypotensive response was recorded.

Results

The inhibitory activity against PAF-induced hypotension was estimated from the rate of PAF-induced hypotensive response (Δ mmHg) after the drug administration to hypotensive response (Δ mmHg) by PAF before the drug administration. The results are shown in Table 7.

TABLE 7

| Restoration activity against PAF-induced hypotension | | | |
|---|---|---|---|
| Test compound (Example No.) | Dose mg/kg, i.v. | Restoration rate (%) | |
| | | After 5 min. | After 60 min. |
| 116 | 1 | 100 | 77 |
| 108 | 1 | 100 | 100 |

TABLE 7-continued

| Restoration activity against PAF-induced hypotension | | | |
|---|---|---|---|
| Test compound (Example No.) | Dose mg/kg, i.v. | Restoration rate (%) | |
| | | After 5 min. | After 60 min. |
| 108 | 0.1 | 100 | 55 |
| 142 | 1 | 100 | 100 |
| 143 | 1 | 100 | 100 |
| 117 | 1 | 100 | 100 |
| 149 | 1 | 100 | 100 |
| 149 | 0.1 | 100 | 39 |

EXPERIMENT EXAMPLE 8

Anti-endotoxin shock activity in rats

Method

Male Spraque-Dawley rats weighing about 400 g were used under pentobarbital sodium (50 mg/kg, i.v.) anesthesia. A cannula was inserted into the femoral artery and secured in position for measurement of blood pressure and another cannula into femoral vein for administration of a solution of the drug. The blood pressure was measured via a pressure transducer and recorded on a polygraph. First, a suspension of endotoxin (15 mg/kg) [Lipopolysaccharide W. E. coli 0111: B4, Wako Pure Chemical] in physiological saline was administered intravenously and the maximum hypotensive response (Δ mmHg) occurring 3 to 5 minutes after administration was recorded. Simultaneously, the compound of Example 108 was dissolved in physiological saline and administered intravenously in a dose of 1 to 100 μg/kg. The restoration rate against endotoxin-induced hypotension one minute after the administration was calculated. The presence of preventive activity against endotoxin shock was judged from the strength of the restoration rate.

Results

The results are shown in Table 8.

TABLE 8

| Inhibition against endotoxin-induced hypotension in rats | | | |
|---|---|---|---|
| Compound (Example No.) | Dose mg/kg, i.v. | Number of rats | Restoration rate (%) against endotoxin-induced hypotension |
| 108 | 0.01 | 2 | 100 |
| | | | 59 |
| | 0.1 | 3 | 97 ± 1* |

*Mean ± standard error

EXPERIMENT EXAMPLE 9

Assay of the effects on inducing differentiation of HL-60 cells (human promyelocytic leukemia cells) and Neuro-2a cells (mouse neuroblastoma cells)

RPMI-1640 medium (Flow Laboratories, Inc.) supplemented with 20% fetal calf serum (M. A. Bio-Products) in a Petri dish of 35 mm diameter was seeded with 2 ml of an HL-60 cell suspension of a concentration of $1 \times 10^5$ cells/ml. To each of thus prepared medium was added 2.5–20 μl of a test compound solution of a given concentration. The culture was incubated at 37° C. in a 5% $CO_2$ incubator for 6 days.

For assay of the effect of each test compound, 100 μl of the cell suspension was taken and the number of cells which did not intake a Trypan Blue solution was counted.

To $1 \times 10^5$ cells taken and washed by means of centrifugation were added 100 µl of a 0.1% nitro blue tetrazolium (NBT) solution and a solution of 12-O-tetradecanoylphorbol-13-acetate (TPA) to make the final concentration 100 ng/ml. The reaction was allowed to proceed at 37° C. for 20 minutes. The reaction was stopped by cooling with ice, and the cells were washed by means of centrifugation, followed by collecting $3-5 \times 10^4$ cells and by subjecting to centrifugation using Cytospin centrifuge to prepare a cell smear, which was fixed with methanol and stained with Kernechtrot solution. On each cell smear, the percentage of NBT-positive cells relative to live cells, determined by examination of a minimum of 200 cells, was expressed as the differentiation extent.

The maximum differentiation extent determined by the above method is shown in Table 9 below.

TABLE 9

| Test compound (Example No.) | Cell differentiation Maximum differentiation extent | |
|---|---|---|
| | Optimal conc. (µg/ml) | Differentiation (%) |
| 45 | 0.48 | 72 |
| 106 | 1.88 | 78 |
| 108 | 0.63 | 83 |
| 115 | 1.25 | 61 |
| 169 (Cl$^-$) | 0.32 | 59 |
| 170 (Cl$^-$) | 0.32 | 77 |
| 177 | 0.48 | 91 |

For Neuro-2a cells, $1 \times 10^4$ cells were inoculated into GIT medium (Daigo-eiyo Chemicals, Japan) and one day later various amounts of the compound of Example 108 were added. The cells were incubated for following three days at 37° C. in a 5% $CO_2$ incubator.

The percentage of cells that were morphologically similar to neurocyte with extended neurite was determined by microscopical examination of cells more than 200.

The results are shown in Table 10.

TABLE 10

| Effect on morphological differentiation of neuroblastoma Neuro-2a | |
|---|---|
| Concentration (µg/ml) | % of cells with neurite |
| 0 | 22 |
| 2.5 | 26 |
| 5 | 33 |
| 10 | 35 |
| 15 | 44 |
| 20 | 74 |

EXPERIMENT EXAMPLE 10

Cell growth inhibition assay $2 \times 10^4$ cells per well charged with GIT medium for KB cells (human epidermoid carcinoma cells), A549 cells (human lung carcinoma cells) and HSC-1 cells (human skin squamous carcinoma cells), and $4 \times 10^4$ cells for B16-BL6 cells (mouse melanoma cells) and $5 \times 10^3$ cells for Neuro-2a cells were inoculated. On day 1 (next day), various concentrations of the compound of Example 108 were added. On day 4, cells were suspended in a solution of trypsin-EDTA and the number of cells was counted. The ratio of cell number in treated culture to that in control culture was estimated as T/C (%) value. The concentration of the compound of Example 108 giving a value of T/C, 50% was defined as $ED_{50}$.

The results are shown in Table 11.

TABLE 11

| Effect on inhibition of cell growth | |
|---|---|
| Cell line | $ED_{50}$ (µg/ml) |
| KB | 0.16 |
| B16-BL6 | 2.5 |
| HSC-1 | 0.63 |
| A549 | 0.63 |
| Neuro-2a | 5.0 |

PREPARATION EXAMPLE 1

In 1.0 l of distilled water is dissolved 10 g of 2-O-acetyl-3-O-[N-acetyl-N-(2'-trimethylammonioethyl)]carbamoyl-1-O-octadecylglycerol iodide, and after strile filtration, the solution is distributed and filled in 1 ml portions into 1000 vials and lyophilized, followed by tightly closing.

On the other hand, 2 l of distilled water for injection containing 100 g of mannitol is distiributed and filled in 2 ml portions into 1000 ampoules for injection, followed by sealing for tightly closing to prepare 1000 injectable solutions.

On the occassion of use, the powder contained in the former one vial is dissolved in the mannitol solution for injection, and is to be put in use.

PREPARATION EXAMPLE 2

Referring to the amounts to be used per tablet:

| | | |
|---|---|---|
| (1) | 2-O-Acetyl-3-O—[N-acetyl-N-(2'-trimethylammonioethyl)]carbamoyl-1-O-octadecylglycerol.iodide | 100 mg |
| (2) | Lactose | 200 mg |
| (3) | Corn starch | 51 mg |
| (4) | Hydroxypropylcellulose | 9 mg | are mixed and granulated by the conventional method, and the granules are incorporated with corn starch (8 mg) and magnesium stearate (2 mg) and compressed to prepare a tablet weighing 370 mg and measuring 9.5 mm in diameter.

PREPARATION EXAMPLE 3

The tablet of Preparation Example 2 is coated with an acetone-ethanol (4:6) mixed solution having hydroxypropylmethylcellulose phthalate (14 mg) and castor oil (1 mg) dissolved to a concentration of 7% to prepare an entericcoated tablet.

PREPARATION EXAMPLE 4

In 1.0 l of distilled water is dissolved 10 g of 3-[N-acetyl-N-(N'-ethylpyridinio-2-yl)methyl]carbamoyl-2-methyl-1-octadecylcarbamoylglycerol chloride, and after sterile filtration, the solution is distributed and filled in 1 ml portions into 1000 vials and lyophilized, followed by tightly closing under aseptic conditions.

On the other hans, 2 l of distilled water for injection containing 100 g of mannitol is distributed and filled in 2 ml portions into 1000 ampoules for injection, followed by sealing for tightly closing to prepare 1000 injectable solutions aseptically.

On the occasion of use, the powder contained in the former one vial is dissolved in the mannitol solution for injection, and is to be put in use.

We claim:

1. A compound of the formula:

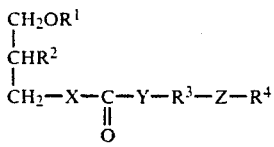

wherein $R^1$ is $C_{10-30}$ alkyl or a group of the formula $R^5NHCO-$ in which $R^5$ is $C_{10-30}$ alkyl;
$R^2$ is hydrogen, hydroxy, $C_{1-5}$ alkoxy, phenyl-$C_{1-5}$ alkoxy, $C_{1-5}$ alkanoyloxy, benzoyloxy, phenoxycarbonyloxy, $C_{1-5}$ alkoxycarbonyloxy, a group of the formula

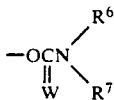

(in which W is oxygen or sulfur, and $R^6$ and $R^7$ are independently hydrogen or $C_{1-5}$ alkyl or both, taken together with the adjacent nitrogen atom, form a 3- to 7-membered hetero ring selected from the class consisting of 1-aziridinyl, 1-azetidinyl, 1-pyrrolidinyl, piperidino, 1-perhydroazepinyl, 1-piperazinyl, morpholino, thiomorpholino, 1-perhydrodiazepinyl, 4-perhydrooxazepinyl and 4-perhydrothiazepinyl), amino, $C_{1-5}$ alkanoylamino, benzoylamino, optionally oxo-substituted 3- to 7-membered monocyclic amino selected from the class consisting of 1-aziridinyl, 1-azetidinyl, 1-pyrrolidinyl, piperidino, 1-perhydroazepinyl, 1-piperazinyl, morpholino, thiomorpholino, 1-perhydroazepinyl, 1-piperazinyl, morpholino, thiomorpholino, 1-perhydrodiazepinyl, 4-perhydrooxazepinyl and 4-perhydrothiazepinyl, or optionally oxo-substituted 2-isoindolinyl;
$R^3$ is $C_{1-8}$ alkylene;
$R^4$ is hydrogen, $C_{1-6}$ alkyl or phenyl-$C_{1-6}$ alkyl;
X is O, S or a group of the formula:

(in which $R^8$ is hydrogen, optionally carboxy or $C_{1-5}$ alkoxycarbonyl substituted $C_{1-5}$ alkyl, $C_{1-5}$ alkanoyl, benzoyl, phenoxycarbonyl, $C_{1-5}$ alkoxycarbonyl, carbamoyl, mono- or di-$C_{1-5}$ alkylcarbamoyl or 3- or 7-membered cyclic aminocarbonyl selected from the class consisting of (aziridin-1-yl)carbonyl, (azetidin-1-yl)carbonyl, (pyrrolidin-1-yl)carbonyl, piperidino-carbonyl, (perhydroazepin-1-yl)carbonyl, (piperazin-1-yl)carbonyl, morpholinocarbonyl and thiomorpholinocarbonyl);
Y is O, S or a group of the formula

(in which $R^9$ is hydrogen, optionally carboxy or $C_{1-5}$ alkoxycarbonyl substituted $C_{1-5}$ alkyl, $C_{1-5}$ alkanoyl, benzoyl, phenoxycarbonyl, $C_{1-5}$ alkoxycarbonyl, carbamoyl, mono- or di-$C_{1-5}$ alkylcarbamoyl or 3- to 7-membered cyclic aminocarbonyl selected from the class consisting of (aziridin-1-yl)carbonyl, (azetidin-1-yl)carbonyl, (pyrrolidin-1-yl)carbonyl, piperidino-carbonyl, (perhydroazepin-1-yl)carbonyl, (piperazin-1-yl)-carbonyl, morpholinocarbonyl and thiomorpholinocarbonyl); and $R^8$ and $R^9$ or $R^4$ and $R^9$ may form $C_{1-4}$ alkenylene or alkylene unsubstituted or substituted by oxo; and Z is a nitrogen-containing heterocyclic group selected from the class consisting of azetidinyl, pyrrolidinyl, piperidinyl, perhydroazepinyl, pyrrolinyl, pyrazolinyl, pyrrolyl, pyridyl, oxazolyl, thiazolyl, pyridazinyl, pyrimidyl, pyrazinyl, imidazolyl, morpholinyl, thiomorpholinyl, piperazinyl, pyrazolidinyl, indolyl, isoindolyl, 1H-indazolyl, purinyl, quinolinyl, isoquinolinyl, 1,2,3,4-tetrahydroquinolinyl, perhydroindolyl and perhydroisoquinolinyl, each of said groups being unsubstituted or substituted by optionally hydroxy- or amino-substituted $C_{1-4}$ alkyl, hydroxy, amino, imino, mono-or di-$C_{1-4}$ alkylamino, carbamoyl, ureido, carboxy, carboxylato or $C_{1-4}$ alkoxycarbonyl, wherein a nitrogen atom in said nitrogen-containing heterocyclic group may be converted into a quaternary salt with $R^4$, wherein $R^3$ is bound to Z at a position adjacent to the nitrogen atom contained in said nitrogen-containing heterocyclic group represented by Z or a pharmaceutically acceptable salt thereof.

2. A compound according to claim 1, wherein $R^1$ is $C_{14-20}$ alkyl or $C_{14-20}$ alkyl—NHCO—.

3. A compound according to claim 1, wherein $R^1$ is $C_{14-18}$ alkyl or $C_{14-18}$ alkyl—NHCO—.

4. A compound according to claim 1, wherein $R^1$ is $C_{15-18}$ alkyl or $C_{15-18}$ alkyl—NHCO—.

5. A compound according to claim 1, wherein $R^1$ is $C_{16-18}$ alkyl or $C_{16-18}$ alkyl—NHCO—.

6. A compound according to claim 1, wherein $R^1$ is octadecyl or octadecylcarbamoyl.

7. A compound according to claim 1, wherein $R^1$ is octadecylcarbamoyl.

8. A compound according to claim 1, wherein $R^2$ is $C_{1-5}$ alkoxy.

9. A compound according to claim 1, wherein $R^2$ is methoxy.

10. A compound according to claim 1, wherein $R^3$ is methylene, ethylene or trimethylene.

11. A compound according to claim 1, wherein $R^3$ is methylene or ethylene.

12. A compound according to claim 1, wherein $R^4$ is hydrogen or $C_{1-6}$ alkyl.

13. A compound according to claim 1, wherein $R^4$ is hydrogen, methyl or ethyl.

14. A compound according to claim 1, wherein X is O, imino or $C_{1-5}$ alkanoylimino.

15. A compound according to claim 1, wherein X is O.

16. A compound according to claim 1, wherein Y is $C_{1-5}$ alkanoylimino.

17. A compound according to claim 1, wherein Y is acetylimino.

18. A compound according to claim 1, wherein

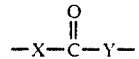

is a group of the formula:

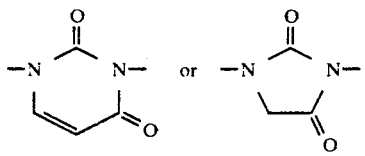

19. A compound according to claim 1, wherein Z—R$^4$ is an optionally C$_{1-6}$ alkyl, C$_{1-4}$ alkoxycarbonyl-C$_{1-6}$ alkyl, carboxylato-C$_{1-6}$ alkyl or phenyl-C$_{1-6}$ alkyl substituted azetidinyl, pyrrolidinyl, piperidinyl, perhydroazepinyl, pyrrolinyl, pyrazolinyl, pyrrolyl, pyridyl, oxazolyl, thiazolyl, pyridazinyl, pyrimidyl, pyradinyl, imidazolyl, morpholinyl, thiomorpholinyl, piperazinyl, pyrazolidinyl, indolyl, isoindolyl, 1H-indazolyl, purinyl, quinolinyl, isoquinolinyl, perhydroindolyl or perhydroisoquinolinyl group being unsubstituted or substituted by optionally hydroxy or amino substituted C$_{1-4}$ alkyl, hydroxy, amino, imino, mono- or di-C$_{1-4}$ alkylamino, carbamoyl, ureido, carboxy, carboxylato or C$_{1-4}$ alkoxycarbonyl.

20. A compound according to claim 1, wherein Z—R$^4$ is an optionally C$_{1-6}$ alkyl, C$_{1-4}$ alkoxycarbonyl-C$_{1-6}$ alkyl, carboxylato-C$_{1-6}$ alkyl or phenyl-C$_{1-6}$ alkyl substituted morpholinyl, pyrrolidinyl, piperidinyl, imidazolyl, pyridyl or thiazolyl group being unsubstituted or substituted by optionally hydroxy or amino substituted C$_{1-4}$ alkyl, hydroxy, amino, imino, mono- or di-C$_{1-4}$ alkylamino, carbamoyl, ureido, carboxy, carboxylato or C$_{1-4}$ alkoxycarbonyl.

21. A compound according to claim 1, wherein Z—R$^4$ is an optionally C$_{1-6}$ alkyl, C$_{1-4}$ alkoxycarbonyl-C$_{1-6}$ alkyl, carboxylato-C$_{1-6}$ alkyl or phenyl-C$_{1-6}$ alkyl substituted pyridyl or thiazolyl group being unsubstituted or substituted by optionally hydroxy or amino substituted C$_{1-4}$ alkyl, hydroxy, amino, imino, mono- or di-C$_{1-4}$ alkylamino, carbamoyl, ureido, carboxyl, carboxylato or C$_{1-4}$ alkoxycarbonyl.

22. A compound according to claim 1, wherein Z—R$^4$ is pyridyl or thiazolyl.

23. A compound according to claim 1, wherein Z—R$^4$ is 2-pyridyl, thiazol-2-yl or thiazol-4-yl.

24. A compound according to claim 1, wherein Z—R$^4$ is an optionally C$_{1-6}$ alkyl, C$_{1-4}$ alkoxycarbonyl-C$_{1-6}$ alkyl, carboxylato-C$_{1-6}$ alkyl or phenyl-C$_{1-6}$ alkyl substituted imidazolio, pyridinio, oxazolio, thiazolio, pyridazinio, pyrimidinio, pyradinio, quinolinio, isoquinolinio, morpholinio, piperidinio, piperazinio or pyrrolidinio group being unsubstituted or substituted by optionally hydroxy or amino substituted C$_{1-4}$ alkyl, hydroxy, amino, imino, mono- or di-C$_{1-4}$ alkylamino, carbamoyl, ureido, carboxy, carboxylato or C$_{1-4}$ alkoxycarbonyl.

25. A compound according to claim 1, wherein Z—R$^4$ is an optionally C$_{1-6}$ alkyl, C$_{1-4}$ alkoxycarbonyl-C$_{1-6}$ alkyl, carboxylato-C$_{1-6}$ alkyl or phenyl-C$_{1-6}$ alkyl substituted morpholinio, pyrrolidinio, piperidinio, imidazolio, pyridinio or thiazolio group being unsubstituted or substituted by optionally hydroxy or amino substituted C$_{1-4}$ alkyl, hydroxy, amino, imino, mono- or di-C$_{1-4}$ alkylamino, carbamoyl, ureido, carboxy, carboxylato or C$_{1-4}$ alkoxycarbonyl.

26. A compound according to claim 1, wherein Z—R$^4$ is an optionally, C$_{1-6}$ alkyl, C$_{1-4}$ alkoxycarbonyl-C$_{1-6}$ alkyl, carboxylato-C$_{1-6}$ alkyl or phenyl-C$_{1-6}$ alkyl substituted pyridinio or thiazolio group being unsubstituted or substituted by optionally hydroxy or amino substituted C$_{1-4}$ alkyl, hydroxy, amino, imino, mono- or di-C$_{1-4}$ alkylamino, carbamoyl, ureido, carboxy, carboxylato or C$_{1-4}$ alkoxycarbonyl.

27. A compound according to claim 1, wherein Z—R$^4$ is 1-(C$_{1-6}$ alkyl)pyridinio-2-yl.

28. A compound according to claim 1, wherein Z—R$^4$ is 1-ethylpyridinio-2-yl.

29. A compound according to claim 1, wherein Z—R$^4$ is 3-(C$_{1-6}$ alkyl)thiazolio-2-yl.

30. A compound according to claim 1, wherein Z—R$^4$ is 3-ethylthiazolio-2-yl.

31. A compound according to claim 1, wherein Z—R$^4$ is 3-(C$_{1-6}$ alkyl)thiazolio-4-yl.

32. A compound according to claim 1, wherein Z—R$^4$ is 3-ethylthiazolio-4-yl.

33. A compound according to claim 1, wherein R$^2$ is C$_{1-5}$ alkoxy, phenyl-C$_{1-5}$ alkoxy, C$_{1-5}$ alkanoyloxy, C$_{1-5}$ alkoxycarbonyloxy, mono- to di-C$_{1-5}$ alkylcarbamoyloxy, C$_{1-5}$ alkanoylamino, 1-aziridinyl, 1-azetidinyl, 1-pyrrolidinyl, piperidino, 1-perhydroazepinyl, 1-piperazinyl, morpholino, thiomorpholino, 1-perhydrodiazepinyl, 4-perhydrooxazepinyl, 4-perhydrothiazepinyl or phthalimido.

34. A compound according to claim 1, wherein Y is O or a group of the formula:

in which R$^9$ is hydrogen, C$_{1-5}$ alkyl, C$_{1-5}$ alkanoyl, C$_{1-5}$ alkoxycarbonyl, carbamoyl, mono- or di-C$_{1-5}$ alkylcarbamoyl, (aziridin-1-yl)carbonyl, (azetidin-1-yl)carbonyl, (pyrrolidin-1-yl)carbonyl, piperidinocarbonyl, (perhydroazepin-1-yl)-carbonyl, (piperazin-1-yl)carbonyl, morpholinocarbonyl or thiomorpholinocarbonyl.

35. A pharmaceutical composition suitable for inhibiting activities of platelet activating factor which comprises as an active ingredient, an effective amount of a compound as claimed in claim 1 or a pharmaceutically acceptable salt thereof, and a pharmaceutically acceptable carrier, excipient or diluent therefor.

36. A pharmaceutically acceptable salt according to claim 1 of 3-O-[N-acetyl-N-(N-methylpyridinio-2-yl)methyl]-carbamoyl-2-O-methyl-1-O-octadecylcarbamoylglycerol with an anion.

37. A pharmaceutically acceptable salt according to claim 1 of 1-ethyl-2-[N-acetyl-N-(3-octadecylcarbamoyloxy-2-methoxypropyloxy)carbonylamino]methylpyridinium with an anion.

38. A pharmaceutically acceptable salt according to claim 1 of 2-[N-acetyl-N-(3-octadecylcarbamoyloxy-2-methoxypropoxycarbonyl)amino]methyl-3-methylthiazolium with an anion.

39. A pharmaceutically acceptable salt according to claim 1 of 2-[N-acetyl-N-(3-octadecylcarbamoyloxy-2-methoxypropoxycarbonyl)amino]methyl-3-ethylthiazolium with an anion.

40. A pharmaceutically acceptable salt according to claim 1 of 2-[N-(3-octadecylcarbamoyloxy-2-ethoxypropyloxycarbonyl)amino]methyl-N-ethylpyridinium with an anion.

41. A pharmaceutically acceptable salt according to claim 1 of 4-[N-acetyl-N-(3-octadecylcarbamoyloxy-2-methoxypropoxycarbonyl)amino]methyl-3-ethylthiazolium with an anion.

* * * * *